United States Patent
Shaviv et al.

(10) Patent No.: US 12,405,222 B2
(45) Date of Patent: Sep. 2, 2025

(54) MEANS AND METHODS FOR DETECTION AND CHARACTERIZATION OF SPECTRALLY STRUCTURED, CONTINUOUSLY CHANGING, DIFFUSE RADIATION SOURCES

(71) Applicant: TECHNION RESEARCH & DEVELOPMENT FOUNDATION LIMITED, Haifa (IL)

(72) Inventors: Giora Shaviv, Haifa (IL); Smadar Bressler, Netanya (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 679 days.

(21) Appl. No.: 17/239,214

(22) Filed: Apr. 23, 2021

(65) Prior Publication Data
US 2021/0310959 A1    Oct. 7, 2021

Related U.S. Application Data

(63) Continuation-in-part of application No. PCT/IL2019/051152, filed on Oct. 24, 2019.
(Continued)

(51) Int. Cl.
*G01N 21/84*   (2006.01)
*G01N 21/31*   (2006.01)
*G16C 60/00*   (2019.01)

(52) U.S. Cl.
CPC ......... *G01N 21/84* (2013.01); *G01N 21/3103* (2013.01); *G16C 60/00* (2019.02)

(58) Field of Classification Search
CPC .... G01N 21/84; G01N 21/3103; G01N 21/31; G01N 21/17; G01N 21/3504;
(Continued)

(56) References Cited

U.S. PATENT DOCUMENTS

| | | | |
|---|---|---|---|
| 6,422,508 B1 * | 7/2002 | Barnes | G01J 3/06 342/63 |
| 2003/0123056 A1 * | 7/2003 | Barnes | G01J 3/2823 356/51 |

OTHER PUBLICATIONS

Shaviv,G. et al (2013) The habitable zone and the generalized greenhouse effect in Habitability of Other Planets and Satellites, de Vera J-P and Seckbach J., eds. in Cellular Origin, Life in Extreme Habitats and Astrobiology, vol. 28, p. 33-46; Retrieved Jul. 22, 2021; DOI:10.1007/978-94-007-6546-7_3.
(Continued)

*Primary Examiner* — Alexander Satanovsky
(74) *Attorney, Agent, or Firm* — The Roy Gross Law Firm, LLC; Roy D. Gross

(57) ABSTRACT

The present invention discloses, inter alia, a method for measuring and analyzing semi-transparent transient sources by remote sensing, comprising the steps of bore-sighting at least one spectrometer and at least one optic device selected from a group consisting of one or more spectrometers, one or more imagers, and at least one spectrometer and at least one imager; mounting at least one bore-sighted pair on at least one platform; and pointing simultaneously all platforms towards at least one field of view. The invention also discloses a platform for remote sensing of semi-transparent transient source comprising at least one first spectrometer in a first wavelength range; at least one second optic device selected from a group consisting of one or more spectrometers, one or more imagers, and at least one spectrometer and at least one imager; each of which is sensitive either in said first wavelength range or in any second wavelength range; at least one platform; wherein said at least one first spectrometer and said at least one second spectrometer are mounted on said platform and bore-sighted to observe the same or at least overlapping field of view.

18 Claims, 26 Drawing Sheets

Related U.S. Application Data

(60) Provisional application No. 62/749,731, filed on Oct. 24, 2018, provisional application No. 62/749,727, filed on Oct. 24, 2018, provisional application No. 62/749,742, filed on Oct. 24, 2018, provisional application No. 62/749,726, filed on Oct. 24, 2018.

(58) Field of Classification Search
CPC ... G01N 2021/1785; G01N 2021/1789; G01N 2021/1795; G01N 2021/17; G16C 60/00; G01J 3/0202; G01J 3/02; G01J 3/0248; G01J 3/0289; G01J 3/28; G01J 3/2889; G01J 3/42; G01J 3/457
See application file for complete search history.

(56) References Cited

OTHER PUBLICATIONS

Hagolle et al.(2010). The Venµs mission and products: A multi-temporal method for cloud detection, applied to Formosat-2, Venµ63 s, Landsat and Sentinel-2 images. Remote Sensing of Environment; Elsevier, 2010,114(8), pp. 1747-1755. Retrieved Jul. 22, 2021 from: http://smsc.cnes.fr/VENUS/index.htm. DOI:10.1016/j.rse.2010.03.002.

Mihalas, D. (1970) Stellar atmospheres, p. 332-337, W.H. Freeman and Co., San Francisco.

Gordon, I.E. et al. (2017) The HITRAN2016 molecular spectroscopic database, Journal of quantitative spectroscopy and radiative transfer. Retrieved Jul. 22, 2021 from https://www.sciencedirect.com/science/article/pii/S0022407317301073.

Madhusudhan & Seager (2009), A Temperature and abundance retrieval method for exoplanet atmospheres. The Astrophysical Journal, 707:24-39, Dec. 10, 2009. Retrieved Jul. 22, 2021; doi: 10.1088/0004-637X/707/1/24.

Kopparapu et al.(2013). Erratum: "Habital zones around main sequence stars: New estimates".The Astrophysical Journal, 770:82 (3pp), Jun. 10, 2013. Retrieved Jul. 22, 2021 from http://dx.doi.org/10.1088/0004-637X/770/1/82.

Rutily, B. et al (2008). Exact results in modeling planetary atmospheres—II. Semi-gray atmospheres. Journal of quantitative spectroscopy and radiative transfer, 109, 28-42. Retrieved Jul. 22, 2021 from https://doi.org/10.1016/j.jqsrt.2007.07.004.

Bressler & Shaviv (2015). Modeling the radiation field in the Greenhouse effect-history and evolution., Astronomical Review, 11:3-4, 41. Retrieved Jul. 22, 2021 from:https://doi.org/10.1080/21672857.2015.1085161.

Rothman et al. (2013). The HITRAN2012 molecular spectroscopic database. Journal of Quantitative Spectroscopy and Radiative Transfer, vol. 130, p. 4-50. Retrieved Jul. 22, 2021 from: http://dx.doi.org/10.1016/j.jqsrt.2013.07.002.

Van Damme et al. (2021). "Global, regional and national trends of atmospheric ammonia derived from a decadal (2008-2018) satellite record." IASI METOP satellite, CNES (2018) Environmental Research Letters 16.5 (2021): 055017. Retrieved Jun. 27, 2021 from https://doi.org/10.1088/1748-9326/abd5e0.

Ribak & Schwartz (2018) "Stationary Fourier Transform Spectrometer," in Frontiers in Optics / Laser Science, OSA Technical Digest (Optical Society of America, 2018), paper JTu2A.142. Retrieved Jul. 22, 2021 from: http://physics.technion.ac.il/~eribak/SPIE11447-250manuscript.pdf.

Shaviv et al, (1972) Statistical Analysis of Multiple Absorption Spectra in QSO, Astrophysics and Space Science, 19(1), pp. 159-163. Retrieved Jul. 22, 2021 from: https://doi.org/10.1007/BF00643173.

Burch et al. & Philco Newport Beach, CA Aeronutronic Div. (1965). Absorption by co2 between 6600 and 7125/cm (1.4 micron region). Defense Technical Information Center. Retrieved Jul. 22, 2021 from https://apps.dtic.mil/sti/citations/AD0624568.

Rudich (2003) Laboratory Perspectives on the Chemical Transformations of Organic Matter in Atmospheric Particles. Chem. Rev. 103 5097-5124. Retrieved Jul. 22, 2021 from: https://doi.org/10.1021/cr020508f.

Teanby et al. (2006). Latitudinal variations of HCN, HC"3N, and C"2N"2 in Titan's stratosphere derived from Cassini CIRS data. Icarus, 181, 243-255. Retrieved Jul. 22, 2021 from: http://dx.doi.org/10.1016/j.icarus.2005.11.008.

Irwin et al. (2008). The Nemesis planetary atmosphere radiative transfer and retrieval tool. Journal of Quantitative Spectroscopy and Radiative Transfer, 109, 1136-1150. Retrieved Jul. 22, 2021 from: dx.doi.org/10.1016/j.jqsrt.2007.11.006.

Jones et al. (2009). Long-term tropospheric formaldehyde concentrations deduced from ground-based fourier transform solar infrared measurements, Atmospheric Chemistry and Physics, 9, 7131-7142, https://doi.org/10.5194/acp-9-7131-2009, 2009.

Brumfield et al. (2015).Characterization of a swept external cavity quantum cascade laser for rapid broadband spectroscopy and sensing, Optics Express, vol. 23, No. 20, pp. 25553-25569. Retrieved Jul. 22, 2021 from: DOI:10.1364/OE.23.025553.

Fu et al. (1992): "On the Correlated κ-Distribution Method for Radiative Transfer in Nonhomogeneous Atmospheres", Journal of the Atmospheric Sciences, vol. 49, No. 22, Nov. 15, 1992 (Nov. 15, 1992), pp. 2139-2156, downloaded Jun. 28, 2021 from: https://doi.org/10.1175/1520-0469(1992)049<2139:OTCDMF>2.0.CO;2.

Frankenberg et al. (2005). Iterative maximum a posteriori (IMAP)-DOAS for retrieval of strongly absorbing trace gases: Model studies for CH 4 and C02 retrieval from near infrared spectra of Sciamachy onboard Envisat, Atmos. Chem. Phys., 5, 9-22, 2005. Retrieved Jul. 22, 2021 from: www.atmos-chem-phys.org/acp/5/9/.

Fink et al. (1969). Collision-Narrowed Curves of Growth for H2 Applied to New Photoelectric Observations of Jupiter., Journal of the Atmospheric Sciences, vol. 26, Sep. 1, 1969 (Sep. 1, 1969), pp. 952-962.

PCT International Search Report for International Application PCT/IL2019/051152, mailed Feb. 23, 2020, 5pp.

PCT Written Opinion for International Application PCT/IL2019/051152, mailed Feb. 23, 2020, 6pp.

PCT International Preliminary Report on Patentability for International Application PCT/IL2019/051152, issued Apr. 27, 2021, 7pp.

"Cellular Origin, Life in Extreme Habitats and Astrobiology", Joseph Seckbach (Ed.), Springer Dordrecht Heidelberg (New York and London), Springer Science + Business Media Dordrecht, ISBN 978-94-007-5109-5. DOI 10.1007/978-94-007-5110-1 , 2012.

Philco (1965). "Scientific Report: Absorption by CO2 Between 660 and 7125 cm (1.4 Micron Region)". Prepared by Burch et al. for Advanced Research Projects Agency, Washington 25, DC, 72pp.

Le Quéré et al. (2016). "Global Carbon Budget 2016", Earth System Science Data 8(2), 605-694.

Robock, Alan, "Volcanic Eruptions and Climate", Review of Geophysics 38 (2), 191-219 , 2000.

Centre National d'Etudes Spatiales—France; Israeli Space Agency—Israel; Cesbio, Toulouse University—France; The Remote Sensing Laboratory, Ben Gurion University of the Negev—Israel; The Venµs mission and products, currently available at http://smsc.cnes.fr/VENUS/index.htm, 2023.

\* cited by examiner

```
c
c This loop sums up n spectra with random noise do 223 j = 1 , n
c
c This loop generates random noise over a simulated spectrum do 222 I = 1 , m err(I) = rand(0)

read(50,*) Wnum(I), Rad cRad    = Rad*err(I)

RadSum(I) = Radsum(I) + cRad
         crrsum(I) = errSum(I) + err(I)

if(j.eq.n) then write(500,*)Wnum(I), Rad, cRad, err(I)
         write(51,*) Wnum(I), RadSum(I)/j
         write(54,*) Wnum(I), errSum(I)/j
         write(501,*)Wnum(I), Rad, RadSum(I)/j endif 222    continue rewind(50)

c
223    continue return end
```

Figure 16a

MEANS AND METHODS FOR DETECTION AND CHARACTERIZATION OF SPECTRALLY STRUCTURED, CONTINUOUSLY CHANGING, DIFFUSE RADIATION SOURCES

CROSS REFERENCE TO RELATED APPLICATIONS

This application is a Continuation in Part of PCT Patent Application No. PCT/IL2019/051152 having a filing date of Oct. 24, 2019, which claims the benefit of priority of U.S. Provisional Patent Application No. 62/749,726, filed Oct. 24, 2018, and U.S. Provisional Patent Application No. 62/749,727, filed Oct. 24, 2018 and U.S. Provisional Patent Application No. 62/749,731, filed Oct. 24, 2018 and U.S. Provisional Patent Application No. 62/749,742, filed Oct. 24, 2018, the contents of which are all incorporated herein by reference in their entirety.

FIELD OF THE INVENTION

The current invention generally pertains to means for remote sensing of spectrally structured, rapidly changing diffuse radiation sources, by simultaneous measurement of a designated field-of-view by means of an array of detectors, on fixed or on moving platforms. The invention further relates to methods for accurate temporal, spatial and spectral mapping of rapidly changing diffuse radiation sources with distinct spectral structure, in at least one spectral domain by exact spatial and temporal overlap of spectral and imaging methods from remote sensing on either fixed or on moving platforms. The current invention further pertains to method for spectral analysis of semi-transparent transient sources, as defined in this invention, to reveal weak spectral absorption lines of chemical species, within measured spectra. First, it describes a method for extracting absorption coefficients from molecular absorption databases at user-defined distinct wavelengths, to create a list of the user defined distinct wavelengths and respective absorption coefficients, which may be used to identify the spectral data in spectra as required for radiative transfer calculations or any other use. Then, it describes a method for data-folding, as defined in this invention, which allows to separate the source from its background, especially important for remote sensing where source and background are measured on the same line of sight. This is also very important for radiative transfer calculations where the line-shape directly determines the influence of the species on its contribution. The invention further relates to a new method for determining the vertical temperature profile and the 3D distribution of atmospheric components within a given planetary atmosphere, using a novel curve of growth calculation to be based on data retrieved from remote sensing. The curve of growth method is adapted from stellar atmospheres and is adjusted to homogeneous and also to non-homogeneous planetary atmospheres, especially for weak spectral lines. This complements the spectral analysis for high resolution measurements, where the spectral line profile can be detected and analyzed by this method.

BACKGROUND OF THE INVENTION

Semi-transparent transient sources, as defined in this invention, are atmospheric volumes, or patches in the marine environment or over ground, which have no definite geometrical shape, but defined chemical structure and physical properties. They are transparent in part of their spatial appearance (optical depth of about 1), they may change in shape continuously, may be homogeneous or non-homogeneous in phase, etc. The uniqueness of the observation by remote sensing of such sources is: (a) that there is no point of reference in their structure to identify where they are observed; (b) their partial transparency leads to emission of radiation from different layers inside them; (c) the spectral detail may be very weak and narrow and require special attention in both measurement and analysis; (d) there may be vertical and/or horizontal gradation in the structure of the observed volume due to specific gravity, diffusion; and, (e) They may be or maybe not in thermodynamic and radiative equilibrium with their surroundings, thus, the measurements are influenced by additional parameters from their surroundings, which should be considered in the analysis. These factors influence the way that these radiation sources are treated.

The importance of studying rapidly changing atmospheric weak radiation sources cannot be underestimated for the study of climate control—for example, clouds are the greatest uncertainty factor in climate studies (IPCC Fifth Assessment Report, 2014); Volcanic eruptions are responsible for cold periods around the globe due to their plumes, see Alan Robock, 2000, Volcanic eruptions and climate, Reviews of geophysics 38 (2) 191-219, incorporated herein as a reference; and winds carry with them different atmospheric chemical species, which influence geographical regions far off from where the chemicals are produced; see Corinne Le Quere et al, 2016, Global carbon budget, Earth system science data 8 (2) 605-649) incorporated herein as a reference.

The graded density of the chemical components of the semi-transparent transient sources in the different layers, requires a radiative transfer model to retrieve its P, T, C (Pressure, Temperature, Concentration) properties including the transmitted and reflected radiation in each layer. A coherent radiative transfer model of the source requires the calculation of energy conservation throughout the spectrum, which is essential for the understanding of the radiative parameters associated with the radiation source. In order to calculate the radiative properties from the measured spectra (e.g. with our home-made radiative transfer code), the total incoming and outgoing radiative energy associated with this transient source should be available. Also, a reference of the background spectra, especially on the same line of sight, should be subtracted from the source spectra, to reveal its accurate spectral structure.

The basics of our home-made energy conserving radiative model are brought here from Shaviv G. et al (2013) The habitable zone and the generalized greenhouse effect in Habitability of Other Planets and Satellites, de Vera J-P and Seckbach J., eds. in Cellular Origin, Life in Extreme Habitats and Astrobiology, vol 28, p: 33-46 incorporated herein as a reference.

The hereto described radiative transfer code for radiative transfer in planetary atmospheres calculates from first principles the inner structure of planetary atmospheres, done by the following steps: Determining an astronomical configuration of a planet, star, and star class; Dividing the planetary atmosphere into layers; Guessing an initial temperature structure for the planetary atmosphere and surface temperature; Reading the composition and chemical structure of the atmosphere (humidity, scale height, pressure, mixing factors); Reading the spectral line data from a data-base;

Determining line profiles using partition functions of the chemical species, from data and P, T, C information; Defining the boundary conditions:
  (i) at the top of the atmosphere-all incoming stellar radiation denoted by $I^-(Z)$, the downward specific intensity impinging at the top of the atmosphere:

$$I^-(Z) = \frac{1}{4}\frac{R_*^2}{d^2}B(T_*, \lambda)$$

(ii) at the surface—the planetary surface does not store or lose any energy—$a(\lambda)$ is the albedo of the planetary surface and $T_{surf}$ is the unknown surface temperature, which is iterated for:

$$\int_0^\infty (1-a(\lambda))I^-(0,\lambda)d\lambda = \sigma T_{surf}^4$$

(iii) the top boundary condition, that is:

$$\frac{R_*^2}{d^2}\int_0^\infty B(T_*,\lambda) = \frac{R_*^2}{d^2}\sigma T_*^4 = \int_0^\infty I^+(z,\lambda)d\lambda$$

is not imposed, and is a result of the energy conserving calculation. It serves only as a consistency check of the calculation.
  (iv) For semi-transparent sources with no rigid surface, additional conditions for the semi-transparent transient source, as defined in this invention, are added (see claims below).

Further step is imposing the energy conservation equation at each point in the atmosphere. Thus for every layer:

$$\int_0^\infty [B(T(z),\lambda) - J(z,\lambda)]\kappa(z,\lambda)d\lambda = 0$$

The integration is carried over all spectral lines including the shape of the lines and there are order of 100 million spectral lines involved.

In the two-stream approximation $$J(z,\lambda) = \frac{I^+(z,\lambda) + I^-(z,\lambda)}{2}$$

$B(T(z), \lambda)$ is the Planck function for every layer and wavelength, and $\kappa(z, \lambda)$ is the absorption coefficient for the same. Then, activating a double iteration scheme on the radiative transfer equation, where the first iteration settles the new P, T profile for the atmosphere and the second iteration settles the surface temperature in equilibrium with the temperature profile.

The measurement of the spectrum and its analysis allows the collection of the data, which is crucial for the understanding of the physics and chemistry of spectrally structured radiative sources. The separation of the rapidly changing weak absorption from its surroundings is both a technological and computational challenge, requiring a high resolution spectrometer in the spectral domain where the studied species absorbs, but also a delicate spectral analysis which allows for uplifting the weak signal from its noisy background, in order to study about its composition and time resolved change. Technically, also short integration times of detectors and rapid repeatability of spectral measurements in short timescales, are essential.

If the change occurs rapidly, it is crucial to measure the phenomena simultaneously and within the same field-of-view, such that the changing phenomena can be analyzed at one shot. An addition of obtaining a simultaneous image, allows to complement the measured spectral properties with the appearance of the source at the same or at a different wavelength range at the specific location where the spectrum is taken, and thus to create a reference within the diffuse source for the spectral measurement.

A common solution to this problem is multispectral and hyperspectral methods which are in use today, by which spectral data and images of the same field of view are collected simultaneously, see Centre National d'Etudes Spatiales—France; Israeli Space Agency—Israel; CESBIO, Toulouse University—France; The Remote Sensing Laboratory, Ben Gurion University of the Negev—Israel; *The Venus mission and products*, currently available at http://smsc.cnes.fr/VENUS/index.htm, etc., all are incorporated herein as a reference. Both methods, however, suffer from difficulties related with the study of radiative transfer of semi-transparent transient sources. The multi-spectral method measures only a small number of bands within the source's full spectrum, which makes it impossible to conduct a full energy transfer solution; whereas high resolution hyperspectral measurements yield continuous spectral ranges but are limited to small amounts of data that can be obtained and calculated. For example, in the push-broom method, the spectral range maybe widened, but the measurements and analysis may take longer than the transient phenomena's timescale.

The exact spectral line profiles as obtained from hyperspectral measurements, and not the spectral bands obtained from band spectroscopy, are the tools to study the physical environment inside the semi-transparent transient source as described above. The shape of the spectral lines is sensitive to the temperature and pressure at different layers of the source, and these may be extracted from a high-resolution spectrum. A well-known tool in stellar astrophysics to learn about the depth of a stellar atmosphere from its spectrum is called the curve of growth (herein after "COG"). In stars this procedure is relatively easy because atomic lines in stellar atmospheres are well separated from each other. In planetary atmospheres, however, where rotation/vibration lines prevail, the situation requires more complex tools. Also, in planets, in contrast to stars, different layers may be non-homogeneous in composition relative to others.

A standard method for evaluating the abundances of chemical species in stellar atmospheres is the COG, see e.g., Mihalas, D. (1970) Stellar atmospheres, p: 332-337, W.H. Freeman and Co., San Francisco, incorporated herein as a reference. Assuming a species concentration fixed with depth, the theory of the COG evaluates the equivalent width of a spectral line as a function of the concentration times the transition probability of the line. The methods take into account the Doppler and the pressure broadening, as it is based on the Voigt function.

The classical method is based on a single line, which is far from being the case in when multiple molecular lines are present. Hence a substantial modification is called for.

Moreover, the commonly used COG method does not take into account a variable concentration with height, as trace gases may show. Hence, it is generalized hereto after the method to include molecular lines, with the unique continuum they pose, as well as a height dependent concentration in non-homogeneous atmospheres. The standard remote sensing method relies on the high optical depth lines, while this invention looks inter alia for the small optical depth lines. By considering lines with different widths, one can detect the lines originating at different heights, including those formed near the surface, in contrast to strong lines only.

The technology disclosed below considers narrow lines having a low equivalent width found in the midst of heavy absorption lines. The lines under discussion are a few tens of angstroms wide and are found within absorption windows of other chemical species, especially water vapors.

It is obvious that the result depends critically on how accurate the absorption of the, e.g. water vapors are evaluated. One should also note that our evaluation includes an iteration for the temperature profile. No assumption of a standard atmosphere is made herein after.

The weak nature of the lines requires intervention in both data collection and analysis. In the data collection stage, it is necessary to: (a) optimize the measuring conditions so as to measure at best conditions to get the best results possible; (b) reduce the noise ($1/\sqrt{N}$) as much as possible by measuring many data points for which "$\tau_{spectro} < \tau_{source}$", as defined in this invention; (c) to obtain measurements from different angles; (d) to obtain measurements of the widest spectral base as possible.

In the data analysis stage, folding many measurements, as defined in this invention for averaging them and then comparison with the spectral parameters in existing databases is required. As the number of known spectral lines of common and trace atmospheric chemical species is constantly rising, "with the recent advances in both laboratory spectrometers and the power of theoretical treatments such as ab initio calculations", see in the discussion of the HITRAN2016 database, see Gordon, I. E et al (2017) The HITRAN2016 molecular spectroscopic database, *Journal of quantitative spectroscopy and radiative transfer* July 2017, incorporated herein as a reference, it is becoming more difficult to conduct RT calculations which are energy conserving. Even with the introduction of parallelization, complete radiative transfer calculations require a lot of computing power, and is thus compensated for by suggesting short-cut methods which include analytic calculations instead of full numerical solutions, numerical methods with k-distribution coefficients assuming a given temperature profile, extrapolation from short spectral ranges choosing only part of the spectrum for the calculation, thus not accounting for full energy conservation, etc., which compromise on the quality of the data by neglecting the absorption in some wavelength domains, Madhusudhan and Seager (2009), ApJ, 707, 24; Kopparapu R. K., et al (2013) ApJ765, 131; Rutily, B. et al (2008) Journal of quantitative spectroscopy and radiative transfer, 109, 28; Bressler & Shaviv 2015, Astronomical Review, 11:3-4, 41 for a full review of radiative transfer models and calculation methods, all are incorporated herein as a reference.

Databases such as HITRAN2016 reach a very large number of spectral lines, 2-200 Mega lines, for each chemical substance. In a fully energy conserving radiative transfer analysis, this requires long computing times and makes it very time consuming.

This calls for a method for data reduction from spectral databases; such as HITRAN in its updated version, e.g. Gordon, I. E et al (2017) The HITRAN2016 molecular spectroscopic database, *Journal of quantitative spectroscopy and radiative transfer* July 2017, incorporated herein as a reference; whose advantage is that it can be done without losing information.

Additionally, the study of remote sensing of semi-transparent transient radiation sources, as defined in this invention, which differ in their spectral structure from their outside environment, poses challenges, due to their unique chemical structure, and different temperature and/or pressure values. This is relevant to the study of semi-transparent transient sources such as e.g., clouds, marine algae patches, chimney, fire and volcano plumes, etc.

Real-time observations of continuous, wide spectral ranges simultaneous with imaging of spectrally structured semi-transparent transient sources, and also a measuring and analysis method which allows to characterize their radiative properties, is a long felt need for radiative transfer characterization of semi-transparent transient sources.

BRIEF DESCRIPTION OF THE FIGURES

In order to understand the invention and to see how it may be implemented in practice, a plurality of embodiments is adapted to now be described, by way of non-limiting example only, with reference to the accompanying drawing, in which:

FIG. 1*a*—a schematic diagram; FIG. 1*b*—a photograph of the same; FIG. 1*c*—a close-up photo; FIG. 1*d*—a unique adaptor for holding the optic fiber in place, according to an embodiment of the invention;

FIGS. 16a-b shows the method for data folding and the calculation results for a real spectrum with the addition of random noise according to an embodiment of the invention;

SUMMARY OF THE INVENTION

Figure 1A:
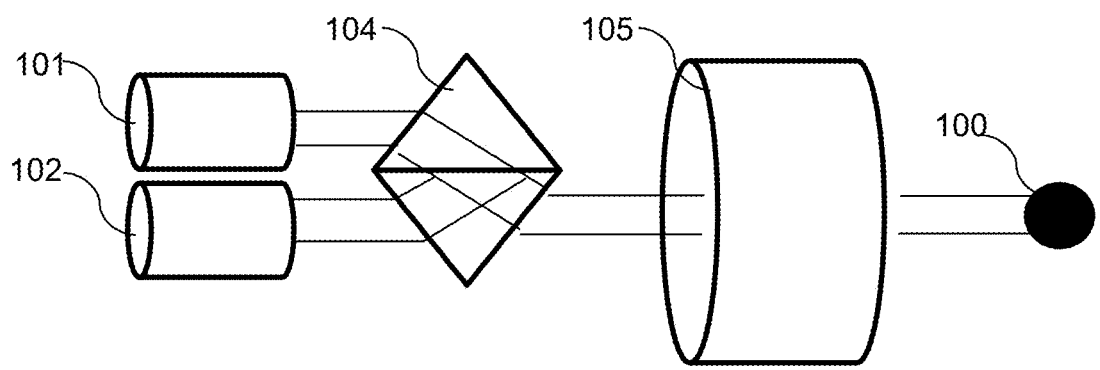
FIG. 1*a-d* is a schematic diagram and pictures of a telescope with an attached beam-splitter on which a spectrometer's optic fiber and a camera are pointed at the same field of view.
Figure 1B:
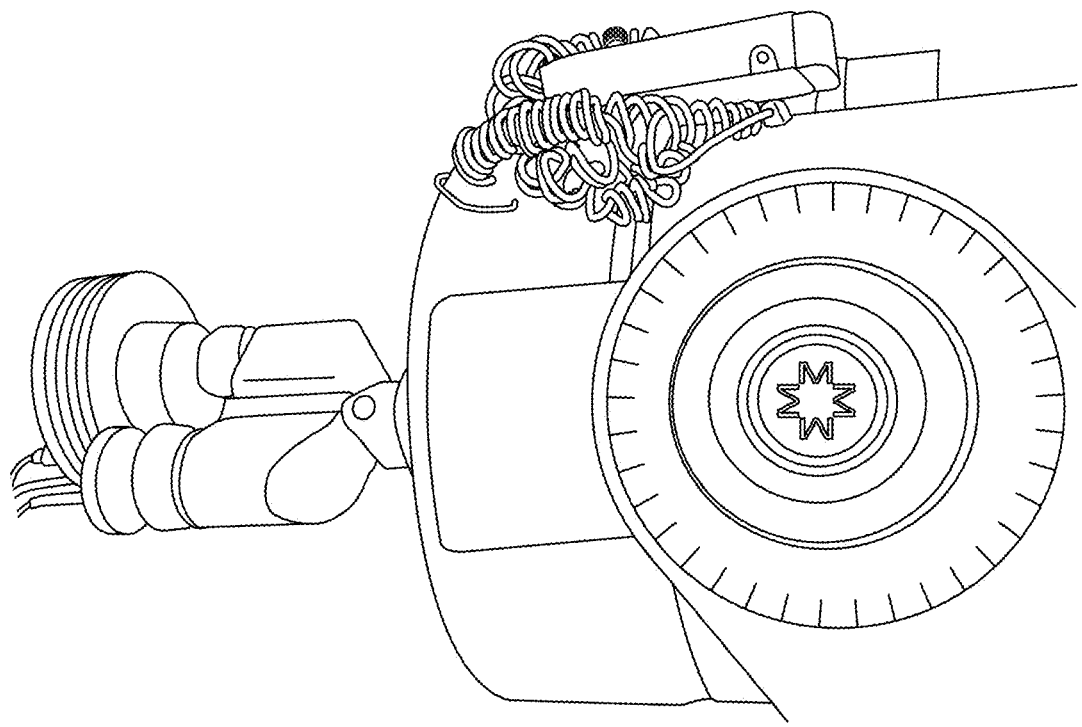
Figure 1C:
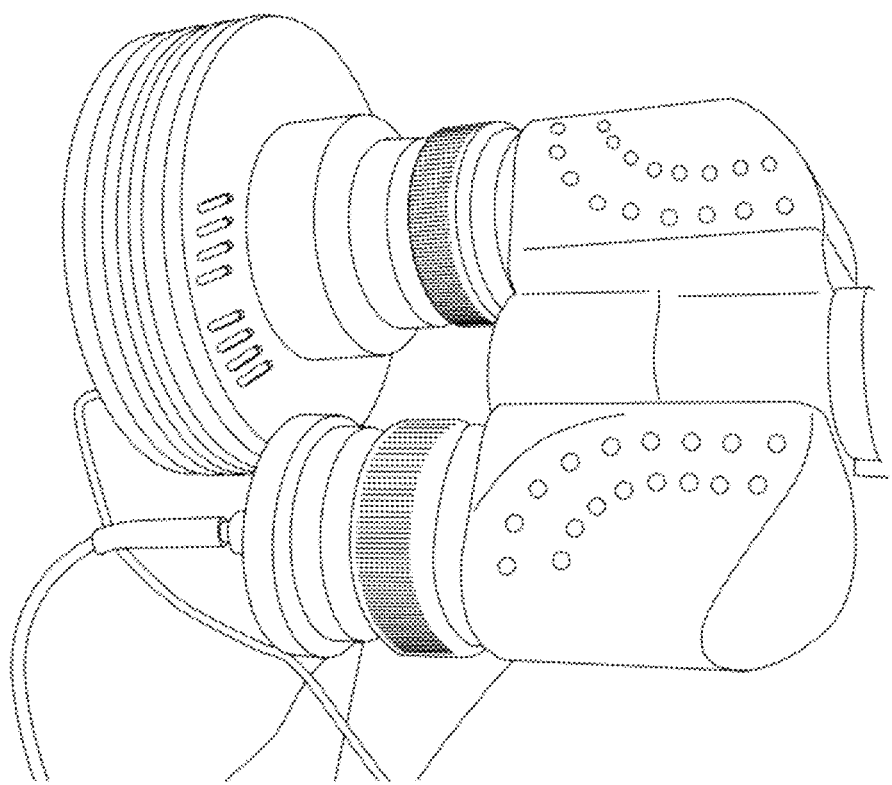
Figure 1D:
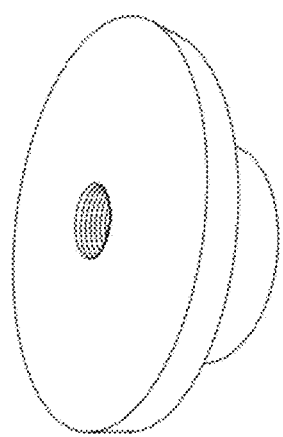

It is thus an object of the invention to disclose a method for measuring and analyzing semi-transparent transient sources by remote sensing, comprising the steps of bore-sighting at least one spectrometer and at least one optic device selected from a group consisting of one or more spectrometers; one or more imagers; and at least one spectrometer and at least one imager; mounting at least one bore-sighted pair on at least one platform; and pointing simultaneously all platforms towards at least one field of view.

It is yet another object of the invention to disclose a method as defined above, wherein the method comprises steps of providing one two or more platforms for remote sensing of semi-transparent transient source, each of which comprising at least one first spectrometer in a first wavelength range; at least one second optic device selected from a group consisting of (i) one or more spectrometers, (ii) one or more imagers, and (iii) at least one spectrometer and at least one imager; each of which is sensitive either in the first wavelength range or in any second wavelength range; at least one platform; wherein the at least one first spectrometer and the at least one second optic device are mounted on the platform and bore-sighted to observe the same or at least overlapping field of view; bore sighting the pair of (i) the at least one first spectrometer and (ii) the second optic device; pointing the bore-sighted pair towards a semi-transparent transient source; taking at least one measurement of the source from the bore-sighted pair within a timescale $\tau_{spectro}$ shorter than $\tau_{source}$, and at least one measurement of a reference field-of-view; online or offline processing the same; subtracting the reference from folded data of measurement(s) of the source; calculating radiative transfer of the semi-transparent transient source; and by overlapping of the spectral and other spectral or imaging data in the processing unit, studying the radiative transfer through the source, and comparing it to its spatial arrangement.

It is another object of the invention to disclose a method as defined above, wherein the method comprises steps of by using window, extracting absorption coefficients from database without losing spectral data information;

(a) bore-sighting at least one spectrometer with at least one spectrometer or imager;
(b) mounting at least one bore-sighted pair on at least one platform;
(c) pointing simultaneously all platforms towards at least one field of view;
(d) acquiring data simultaneously by spectrometer, and second optic device, from at least one platform of semi-transparent transient source;
(e) acquiring data simultaneously or alternately by spectrometer, and by spectrometer or imager from at least one platform of semi-transparent transient source; and reference field of view for semi-transparent transient source;
(f) acquiring data simultaneously or alternately by spectrometer, and by second optic device from at least one platform of at least two complementary fields of view of the source if required;
(g) repeating at least one of step (e) to (g), from at least one platform, for a total timescale which is shorter than the source timescale;
(h) adjusting data measured for different solid angles of different platforms;
(i) relating spectral data from first spectrometer with data from second optic device as a reference point for spatial resolution in observed properties of the semi-transparent transient source, by corresponding the overlapping field of views;
(j) folding data acquired for each measurement period;
(k) subtracting reference measurement from the measurement of semi-transparent transient sources for each measuring method
(l) building a COG from the spectral line-widths to obtain the concentration profile through the layers; and
(m) using the concentration profile obtained by the COG and an energy conserving radiative code to conclude the structure of the inner radiative field of the semi-transparent transient source for different time resolved stages, thus to follow its change with time.

It is another object of the invention to disclose a method as defined above, wherein at least one of the following is held true: (a) the method further comprising step(s) of tilting the platform towards the source and the reference fields of view; (b) the method is provided useful for enhancing SNR by observing through the source via a longer path, resulting in a larger optical depth of a weakly absorbing species; the method comprising step(s) of tilting the either platform or the bore sighted pair towards an optical path being longer than the vertical line; (c) the method is provided useful for enhancing SNR by observing through a planetary atmosphere via a longer path than the vertical; comprising step(s) of tilting the either platform or the bore sighted pair towards the limb off the Nadir; (d) the method further comprising step of measuring a plurality of tilt angles thereby yielding a vertical profile of the species' concentration in planetary atmospheres; (e) the method is provided useful for enhancing SNR by observing through a source illuminated from the background by an external radiation source in the visible and/or other spectral domain, resulting in direct spectroscopy of a weakly absorbing species; the method comprising step(s) of tilting the either platform or the bore sighted pair towards an external radiation source occulted by the semi-transparent transient source; (f) the method is provided useful for enhancing SNR by observing the semi-transparent transient source through a planetary atmosphere illuminated from the background by an external radiation source in the visible and/or other spectral domain, resulting in direct spectroscopy of the weakly absorbing species in the semi-transparent transient source; the method comprising step(s) of tilting the either platform or the bore sighted pair towards the limb of the planetary surface in angle to the Nadir; (g) the method is provided useful for comprising step of providing a background reference measurement with no source from bore-sighted pair; (h) the method further comprising step of providing a reference measurement of the external radiation source from bore-sighted pair, providing for isolating the semi-transparent transient source's spectrum and from that of the external source and to provide for reference point for spatial resolution of the spectral measurement with the other optic device; (i) the method further comprising step of obtaining pointing knowledge from two or more platforms and providing for overlapping the spectral and the imaging data of the platforms; (j) the method further comprising step of characterizing extremal/internal fluid motion of a rapidly changing diffused radiation source by providing one member of a group consisting the followings: combining spectroscopy and visible imaging, when emission is characterizable by a defined visible spectral range; combining of spectroscopic and either IR or SAR imaging, when emission can be characterized by no visible components; and providing a Doppler shift of spectral lines; (k) the method further comprising step of characterizing extremal/internal fluid motion of a rapidly changing diffused radiation source by providing a Doppler shift of spectral lines in the same or different spectral domains, comprising steps of studying the line shape selected from a members of a group consisting of single non-shifted spectral line; sum of blue-shifted and redshifted lines indicative of motion in both directions, at low spectral resolution; resolved absorption spectra of separate blue shifted and/or red shifted lines if there are any; any combination of absorption and emission lines of the same spectral feature; any combination of absorption and emission lines interconnected with flow of material within semi-transparent transient source; determining extremal/internal fluid motion of a rapidly changing diffused radiation source on one or more axes of observation; and comparing with data from bore-sighted optic device to obtain a point of reference of spatial resolution for the motion in the semi-transparent transient source; (l) the method further comprising step of pointing either the platform and/or the bore sighted pair towards an external radiation source occulted by the semi-transparent transient source; thereby providing for illumination of the semi-transparent transient source by radiation originating in the external radiation source as to allow for direct spectroscopy of the source in wavelength range of external radiation source; (n) the method further comprising step of providing for measuring chemical gradients in the environment of the semi-transparent transient source by observing the semi-transparent transient source from at least two opposite directions; (o) spectral resolution together with spatial resolution allows for tracking down of fast chemical/physical changes within inner layers of semi-transparent transient sources; (q) inside details of semi-transparent transient source with optical depth of about 1 can be characterized; (r) spectral resolution of weak signals is optimized, especially by observations to the horizon; (s) spectral resolution of weak signals is optimized, especially observations towards external light sources selected from moon, stars including sun and artificial light sources, which radiate through the semi-transparent transient source, to allow for direct spectroscopy of its contents; (t) temporal resolution is real time ($\tau_{spectro} < \tau_{source}$); and (u) bore-sighted pairs mounted on multiple platforms provide for improving SNR by acquiring many repeated measurements within timescale of the measurement shorter than source timescale ($\tau_{spectro} < \tau_{source}$).

It is another object of the invention to disclose a platform for remote sensing of semi-transparent transient source comprising at least one first spectrometer in a first wavelength range; at least one second optic device selected from a group consisting of (i) one or more spectrometers; (ii) one or more imagers; and (iii) at least one spectrometer and at least one imager; each of which is sensitive either in the first wavelength range or in any second wavelength range; at least one platform; wherein the at least one first spectrometer and the at least one second spectrometer are mounted on the platform and bore-sighted to observe the same or at least overlapping field of view.

It is another object of the invention to disclose the platform as defined above, wherein the at least one of the following is held true: (a) at least one bore-sighted pair of the first spectrometer and second optic device are mounted on at least one first platform and on at least one second platform; the spectrometer and optic device are pointed simultaneously at the same or at least one overlapping field of view; (b) the at least one first spectrometer is mounted on at least a first platform and the at least one optic device is mounted on at least a second platform; all bore-sighted pairs of the spectrometers on all platforms pointing at the same or at least at overlapping field of view; (c) at least one first spectrometer and the at least one optic device on the same or on different platforms are pointed at the same or at least one overlapping field of view; (d) at least one platform is configured to be tilted to any solid angle for measuring from the bore-sighted pair; (e) at least one platform is configured to be tilted to any solid angle for measuring a plurality of measurements from the bore-sighted pair; and wherein at least one datum and at least one reference fields of view are measured alternately; (f) the reference field of view comprises a field of view other than the measured field of view; (g) the reference field comprises a field of view (FOV) other than the measured field of view; the FOV is selected from a group consisting of clear skies; clear aqueous or marine environment; FOV provided by measuring a same semi-transparent transient source from a different angle; and FOV provided by measuring a same field of view at a different solar angle or at night; (h) a first platform is configured to be tilted to any solid angle, in correlation with a second platform, thereby is provided useful for measuring reference field of view away from a source; (i) a first platform is configured to be tilted to any solid angle, in correlation with a second platform, thereby is provided useful for measuring a same or at least overlapping field of view, from at least two different solid angles; (j) a first platform is configured to be tilted to any solid angle, in correlation with a second platform, thereby is provided useful for measuring complementary fields of view; (k) the platform is operatable in a method of providing the measurement timescale to be shorter than source timescale for change $\tau_{spectro} < \tau_{source}$; (l) the platform is operatable in a method comprising step of conducting a series of measurements from at least one platform within a measuring timescale shorter than the source timescale $\tau_{spectro} < \tau_{source}$; (m) the platform is operatable in a method comprising step of operating both the first spectrometer and an optic device simultaneously; (n) the platform is utilizable in a method where both the first spectrometer and second optic device are operatable in an alternate manner and the operation timescale is shorter than source timescale for change; (o) the platform is operatable in a method comprising a step being a member of a group consisting of (a) correlating data from the first spectrometer and from the second spectrometer or imager; (b) overlapping data for all instruments for measuring timescale shorter than source timescale; (c) correcting for measuring solid angle; and (d) correcting for solar angle; (q) the platform is comprising at least one third backup spectrometer configurable to any of the first and/or second wavelength domains; the backup spectrometer is positioned off the optic axis and is optionally interconnected with a backup motor configured to move the spectrometer out of the optic axis in case of failure of either the first or second spectrometer, thereby providing a continuous platform's operation; (r) the platform is further comprising at least one remote sensor useful for accurate temporal, spatial and/or spectral mapping of spectrally structured rapidly changing radiation sources; (s) the platform is a member of a cluster of three or more platforms; and (t) the platform is operatable in a manner that at least one platform is configured for simultaneous or alternating measurement of source and of reference spectra useful for deducing the net spectrum of the semi-transparent transient source.

It is another object of the invention to disclose a method for measuring and analyzing semi-transparent transient sources by remote sensing comprising steps of: (a) providing absorption coefficients of at least one molecular species from an up-to-date database list of all molecular absorption parameters of the species, as a function of wavelength; (b) creating a user defined list of distinct equally-spaced or arbitrarily chosen wavelengths to provide for which the absorption coefficients are used for the radiative transfer analysis so that their periodicity is chosen as a function (1) of the total wavelength range for which the RT is done, including range of $10^3$ to $10^6$ Å for Earth; (2) of the required resolution of the calculation vis-a-vis the wavelength range of the window; and (3) of the density of the spectral lines with that wavelength range; (c) defining a chosen window wavelength range symmetrically, or non-symmetrically, about the defined wavelengths of the list, chosen so as to include the contribution of adjacent lines to the calculation wavelengths, such that widening the window additionally, does not change significantly the absorption at the chosen calculation points; (d) reading the molecular absorption parameters of the at least one molecular substance at a first data wavelength in the database list; (e) if first database wavelength does not fall within the chosen wavelength range of at least one distinct user-defined wavelength, reading the next database wavelength until it overlaps with the chosen wavelength window range of the first user defined distinct wavelength; (f) calculating from the molecular absorption data a line profile for the database wavelength, given the pressure, temperature, concentration (P,T,C) conditions for the chemical species and atmospheric layer such that the contribution of each line of every species is a function of the species' concentration in the atmosphere, its statistical weight and its calculated profile at high or at low pressure by steps of: (1) preparing the partition function; (2) calculating the Voigt function; (3) choosing, according to the pressure shift, the function for the line shape; at low pressures, pressure shift <200 cm$^{-1}$, use Van-Vleck Weisskopf line shape; at higher pressures, taper the wing effect by reducing the distant effect; and, (4) calculating the statistical weight of the lower level times the transition probability; (g) extracting the contribution from the line profile to the absorption coefficients at each wavelength in the wavelength window range about the user-defined distinct wavelength, as the line profile extends throughout many wavelengths, their contribution to the different calculation points is collected throughout the window range; (h) repeating steps (d) to (g) for each database wavelength until it exceeds the wavelength window range about the last user-defined distinct wavelength; for each calculation point, the window is moved one calculation unit further, thus the initial window wavelength is adjusted accordingly; and (i) obtaining a list of the user defined distinct wavelengths and the respective absorption coefficients which may be stored in the computer for further use for radiative transfer or other calculations or any other use.

It is another object of the invention to disclose a method as defined above, wherein at least one of the following is held true: (1) the single chemical substance is replaceable by a mixture of a plurality of substances; (2) steps (d) to (g) are repeated for every chemical substance, for the same user-defined distinct wavelengths; (3) the absorption coefficients of each chosen chemical substance are added at every user-defined distinct wavelength, thereby creating an additive absorption coefficient wavelength dependency for all substances; (4) the single layer is replaceable by a plurality of adjacent layers of either similar or different chemical composition at either similar or different P, T profiles; (5) steps (d) to (h) are repeated for every chemical substance for the same user defined distinct wavelength list and steps (h) and (i) are repeated for every layer and saved in a separated dimension; (6) an array of computerized processing units are used for processing individual data streams in parallel during the extraction of absorption coefficients of at least one molecular species, in at least one atmospheric layer, defined by given P,T,C parameters, at user-defined distinct wavelengths from molecular absorption databases, thereby obtaining a list of the user defined distinct wavelengths and (7), the respective absorption coefficients which may be stored in the computer for further use for radiative transfer or for other calculations.

It is another object of the invention to disclose a method for deducing the vertical temperature and concentration profiles of chemical species in planetary atmospheres from the curve of growth based on an analysis of remote-sensing spectral data, comprising steps of: (a) obtaining an average temperature value for the planetary surface and/or atmosphere; (b) obtaining a vertical temperature profile, if available; (c) conducting an analysis of the absorption spectrum to identify atmospheric chemical species from comparison of data with spectral line database; (d) identifying a series of narrow lines of the chemical species of several angstroms wide each $\{\lambda^o_1, \ldots, \lambda^o_n\}$ where $\lambda^o$ denotes the central wavelength of the line; (e) calculating the equivalent width $W_k$ for each line k, from the integral of the area under the absorption line, for $\lambda^{0-j}{}_k$ to $\lambda^{0+l}{}_k$, j and l are the extremal wavelengths of the line; (f) dividing the atmosphere arbitrarily into i layers of vertical height (z) denoted by $\Delta i$; (g) obtaining from a given line database the absorption coefficient, $\kappa_i(\lambda)$, for each wavelength of each line; (h) plugging the measured width $W_k$, the given absorption coefficient, $\kappa_i(\lambda)$ and the arbitrary width $\Delta i$ of the given layers for each lambda within the line and for each layer, into the effective line-width equation, adjusted by us for the general case of non-homogenous planetary atmospheres having a vertical distribution of chemical species such that:

$$W_k = 2\sum_j \left(1 - e^{-\Sigma_0^i \kappa_i(\lambda) N_i \Delta_i}\right)$$

where j is the running index over all wavelengths in line k and i is the running index on all atmospheric layers; the sum in the exponent is an approximation valid for thin lines only (i) calculating simultaneously the values of $W_k$ for all lines, by parameterizing an array of values for the concentrations of the chemical species $N_{i,j}$ for all wavelengths and atmospheric layers involved in the calculation of each line, and by iterating to convergence with a very high degree of accuracy, including about $10^{-9}$, to avoid local minima in the calculation; (j) defining curve of growth for all lines k, as described from the relationship log $(W_k/\Delta v_D)$ vs log $(\Sigma_j \Sigma_i N_{i,j})$; $\Delta v_D$ is the Doppler broadening of the line and is a function of T(z), thus requiring the input of vertical temperature profile by obtaining the same from: (1) given measured vertical temperature profile T(z); or, (2) as a first approximation deduced from an assumption of exponential decay of the pressure with height; or (3) calculated from the hydrostatic equation for the planet; or, (4) fully or partially parameterized during calculation of $W_k$ as a separate or a simultaneous iteration scheme, validated by the measured average temperature obtained from remote sensing data; (k) drawing the curve of growth from the $W_k$ and the $N_{i,j}$ array values for each line and from it, and obtaining a best fit curve; (l) obtaining from the curve of growth the profile of the line effective width, representative of the absorption vs chemical species concentration in line of sight, for any spectral line of the chemical species at any height z provided it is only several angstroms wide; and (m) providing the real vertical chemical species distribution consistent with the vertical layer widths $\Delta_i$, by using appropriate T, P values.

It is another object of the invention to disclose a method for deducing the vertical temperature and concentration profiles of chemical species in planetary atmospheres from the curve of growth based on an analysis of remote-sensing spectral data as defined above, wherein the method is formalized by processing by the following equations:

(a) if planetary atmosphere is homogeneous, then $\tau$, the optical depth is uniform in volume and the standard equivalent width $W_k$ of a spectral line k is calculated according to the following formula:

$$W_k = 2\int_0^\infty \left(1 - e^{-\tau(z,\lambda)}\right)d\lambda$$

(b) if the planetary atmosphere is not homogeneous and the gas concentration N(z) depends on height z, then $\tau$ is not uniform with height and is given by:

$$\tau(z, \lambda) = \int_{z=0}^z \kappa(\lambda) N(z) dz$$

were $\kappa(\lambda)$ is the wavelength dependent absorption coefficient; the equivalent width is given by $$W_k = 2\int_0^\infty \left(1 - e^{-\tau(z,\lambda)}\right)d\lambda = 2\int_0^\infty \left(1 - e^{-\int_{z=0}^z \kappa(\lambda)N(z)dz}\right)d\lambda$$

(c) for a finite planetary atmosphere, each layer is denoted with the index i, and the integrals is written as finite sums so that:

$$\tau(z, \lambda) = \sum_0^i \kappa_i(\lambda) N_i \Delta_i$$

is the physical width of the atmospheric layer, $\kappa_i(\lambda)$ and $N_i$ are the wavelength dependent absorption coefficient and species' concentration for the i'th layer, respectively, then, the equivalent width W of a certain line k, where j is the index for the wavelengths, becomes:

$$W_k = 2\sum_j \left(1 - e^{-\Sigma_0^i \kappa_i(\lambda) N_i \Delta_i}\right)$$

the unknown is $N_i$, which appears in k equations for k parameters, and thus can be solved for; and (d) if the expression in the exponent is large, due to heavy absorption, high concentration or large layer height, $W_k$ will vanish and no contribution will be gained from this line, chosen lines should thus satisfy the condition $\kappa_i(\lambda) N_i \sim 1$ in narrow layers, for $W_k$ to be valuable.

It is another object of the invention to disclose a method for deducing the vertical temperature and concentration profiles of chemical species in planetary atmospheres from the curve of growth based on an analysis of remote-sensing spectral data as defined above, wherein the method additionally comprising steps of: (a) conducting an analysis of the absorption spectrum to identify atmospheric chemical species from comparison of data with spectral line database; (b) identifying a series of narrow lines of the chemical species of several angstroms wide each $\{\lambda^0_1, \ldots, \lambda^0_n\}$ where $\lambda^0$ denotes the central wavelength of the line; (c) calculating the equivalent width $W_k$ for each line k, from the integral of the area under the absorption line, for $\lambda^{0-j}{}_k$ to $\lambda^{0+j}{}_k$, j and l are the extremal wavelengths of the line; (d) obtaining from a given line database the absorption coefficient, $\kappa_i(\lambda)$, for each wavelength of each line; (e) plugging the measured width $W_k$, the given absorption coefficient, $\kappa_i(\lambda)$, and the arbitrary width $\Delta_i$ of the given layers for each lambda within the line and for each layer, into the effective line-width equation, adjusted by us for the general case of non-homogenous planetary atmospheres having a vertical distribution of chemical species such that:

$$W_k = 2\sum_j \left(1 - e^{-\Sigma_0^i \kappa_i(\lambda) N_i \Delta_i}\right)$$

where j is the running index over all wavelengths in line k and i is the running index on all atmospheric layers; the sum in the exponent is an approximation valid for thin lines only; (f) calculating simultaneously the values of $W_k$ for all lines, by parameterizing an array of values for the concentrations of the chemical species $N_{i,j}$ for all wavelengths and atmospheric layers involved in the calculation of each line, and by iterating to convergence with a very high degree of accuracy, including about $10^{-9}$, to avoid local minima in the calculation; (g) drawing the curve of growth for all lines k, is described from the relationship log ($W_k/\Delta\nu_D$) vs log ($\Sigma_j \Sigma_i N_{i,j}$); $\Delta\nu_D$ is the Doppler broadening of the line and is a function of T(z), thus requiring the input of vertical temperature profile; this may be obtained from: (1) given measured vertical temperature profile T(z); or, (2) as a first approximation, deduced from an assumption of exponential decay of the pressure with height; or (3) calculated from the hydrostatic equation for the planet; or, (4) fully or partially parameterized during calculation of $W_k$ as a separate or a simultaneous iteration scheme, validated by the measured average temperature obtained from remote sensing data; (h) drawing the curve of growth from the $W_k$ and the $N_{i,j}$ array values for each line and from it, a best fit curve is obtained; (i) obtaining from the curve of growth, the profile of the line effective width, representative of the absorption, vs chemical species concentration in line of sight; for any spectral line of the chemical species at any height z provided it is only several angstroms wide; and (j) obtaining the real vertical chemical species distribution being consistent with the vertical layer widths $\Delta_i$, by using appropriate T, P values.

It is another object of the invention to disclose a method for deducing the vertical temperature and concentration profiles of chemical species in planetary atmospheres from the curve of growth based on an analysis of remote-sensing spectral data as defined above, wherein
(a) if the planetary atmosphere is homogeneous, then τ, the optical depth is uniform in volume and the standard equivalent width $W_k$ is calculated according to the following formula:

$$W_k = 2\int_0^\infty \left(1 - e^{-\tau(z,\lambda)}\right)d\lambda$$

(b) if the planetary atmosphere is not homogeneous and the gas concentration N(z) depends on height z, then τ is not uniform with height and is given by:

$$\tau(z, \lambda) = \int_{z=0}^z \kappa(\lambda) N(z) dz$$

where $\kappa(\lambda)$ is the wavelength dependent absorption coefficient; the equivalent width is given by:

$$W_k = 2\int_0^\infty \left(1 - e^{-\tau(z,\lambda)}\right)d\lambda = 2\int_0^\infty \left(1 - e^{-\int_{z=0}^z \kappa(\lambda) N(z) dz}\right)d\lambda$$

(c) for a finite planetary atmosphere, each layer is denoted with the index i, and the integrals can be written as finite sums so that:

$$\tau(z, \lambda) = \sum_0^i \kappa_i(\lambda) N_i \Delta_i$$

where $\Delta_i$ is the physical width of the atmospheric layer, $\kappa_i(\lambda)$ and $N_i$ are the wavelength dependent absorption coefficient and species' concentration for the i'th layer, respectively; then, the equivalent width W of a certain line k, where j is the index for the wavelengths, becomes:

$$W_k = 2\sum_j \left(1 - e^{-\Sigma_0^i \kappa_i(\lambda) N_i \Delta_i}\right)$$

the unknown is $N_i$, which appears in k equations for k parameters, and thus can be solved for;
(d) if the expression in the exponent is large, due to heavy absorption, high concentration or large layer height, $W_k$ will vanish and no contribution will be gained from this line; chosen lines should thus satisfy the condition $\kappa_i(\lambda) N_i \sim 1$ in narrow layers, for $W_k$ to be valuable.

It is another object of the invention to disclose a method for deducing the vertical temperature and concentration profiles of chemical species in planetary atmospheres from the curve of growth based on analysis of remote sensing spectral data, comprising steps of: (a) providing an absorption spectrum measured by remote-sensing for the planetary atmosphere; and (b) dividing the atmosphere into i layers of vertical height (z) denoted by $\Delta_i$, such that the temperature and concentration profiles of chemical species is calculated for each of the i layers within each of the n vertical columns.

It is another object of the invention to disclose a method for deducing the vertical temperature and concentration profiles of chemical species in planetary atmospheres from the curve of growth based on analysis of remote sensing spectral data as defined above, wherein the method additionally comprising steps of: (a) conducting an analysis of the absorption spectrum to identify atmospheric chemical species from comparison of data with spectral line database; (b) identifying a series of narrow lines of the chemical species of several angstroms wide each $\{\lambda^0_1, \ldots, \lambda^0_n\}$ where $\lambda^0$ denotes the central wavelength of the line; (c) calculating the equivalent width $W_k$ for each line k, from the integral of the area under the absorption line, for $\lambda^{0-j}_k$ to $\lambda^{0+j}_k$, j and l are the extremal wavelengths of the line; (d) obtaining from a given line database the absorption coefficient, $\kappa_i(\lambda)$ and $N_i$ for each wavelength of each line; (e) plugging the measured width $W_k$, the given absorption coefficient, $\kappa_i(\lambda)$ and the arbitrary width $\Delta_i$ of the given layers for each lambda within the line and for each layer, into the effective line-width equation, adjusted by us for the general case of non-homogenous planetary atmospheres having a vertical distribution of chemical species such that:

$$W_k = 2\sum_j \left(1 - e^{-\Sigma_0^i \kappa_i(\lambda) N_i \Delta_i}\right)$$

where j is the running index over all wavelengths in line k and i is the running index on all atmospheric layers; the sum in the exponent is an approximation valid for thin lines only; (f) calculating simultaneously the values of $W_k$ for all lines, by parameterizing an array of values for the concentrations of the chemical species $N_{i,j}$ for all wavelengths and atmospheric layers involved in the calculation of each line, and by iterating to convergence with a very high degree of accuracy, including about $10^{-9}$, to avoid local minima in the calculation; (g) drawing the curve of growth for all lines k, is described from the relationship log ($W_k/\Delta v_D$) vs log ($\Sigma_j \Sigma_i N_{i,j}$); $\Delta v_D$ is the Doppler broadening of the line and is a function of T(z), thus requiring the input of vertical temperature profile; this may be obtained from: (1) given measured vertical temperature profile T(z); or, (2) as a first approximation deduced from an assumption of exponential decay of the pressure with height; or (3) calculated from the hydrostatic equation for the planet; or, (4) fully or partially parameterized during calculation of $W_k$ as a separate or a simultaneous iteration scheme, validated by the measured average temperature obtained from remote sensing data; and (h) the curve of growth is drawn from the $W_k$ and the $N_{i,j}$ array values for each line and from it, a best fit curve is obtained. From the curve of growth, the profile of the line effective width, representative of the absorption vs chemical species concentration in line of sight, can be obtained for any spectral line of the chemical species at any height z provided it is only several angstroms wide; and, the real vertical chemical species distribution is then made consistent with the vertical layer widths $\Delta_i$, by using appropriate T, P values.

It is another object of the invention to disclose a method for deducing the vertical temperature and concentration profiles of chemical species in planetary atmospheres from the curve of growth based on analysis of remote sensing spectral data as defined above, wherein (a) standard equivalent width $W_k$ for homogeneous atmosphere is calculated according to the following formula:

$$W_k = 2\int_0^\infty (1 - e^{-\tau(z,\lambda)})d\lambda$$

(b) if the planetary atmosphere is not homogeneous and the gas concentration N(z) depends on height z, then $\tau$ is not uniform with height and is given by:

$$\tau(z, \lambda) = \int_{z=0}^z \kappa(\lambda)N(z)dz$$

where $\kappa(\lambda)$ is the wavelength dependent absorption coefficient; the equivalent width is given by:

$$W_k = 2\int_0^\infty (1 - e^{-\tau(z,\lambda)})d\lambda = 2\int_0^\infty (1 - e^{-\int_{z=0}^z \kappa(\lambda)N(z)dz})d\lambda$$

c. for a finite planetary atmosphere, each layer is denoted with the index i, and the integrals can be written as finite sums so that:

$$\tau(z, \lambda) = \sum_0^i \kappa_i(\lambda)N_i\Delta_i$$

is the physical width of the atmospheric layer, $W_k$ and the $N_{ij}$ are the wavelength dependent absorption coefficient and species' concentration for the i'th layer, respectively; then, the equivalent width W of a certain line k, where j is the index for the wavelengths, becomes:

$$W_k = 2\sum_j \left(1 - e^{-\sum_0^i \kappa_i(\lambda)N_i\Delta_i}\right)$$

the unknown is $N_i$, which appears in k equations for k parameters, and thus can be solved for;

d. if the expression in the exponent is large, due to heavy absorption, high concentration or large layer height, $W_k$ will vanish and no contribution will be gained from this line; chosen lines should thus satisfy the condition $\kappa_i(\lambda)N_i \sim 1$ in narrow layers, for $W_k$ to be valuable.

It is another object of the invention to disclose a method for accurate spectral analysis of semi-transparent transient sources comprising steps of: (a) identifying a semi-transparent transient source; (b) providing for a sequence of spectral measurements of the source from the same or from different viewing angles; (c) providing for the sequence of spectral measurements of the source within a timescale $\tau_{spectro}$ shorter than or equal to the rapid-change timescale $\tau_{source}$ ($\tau_{spectro} \leq \tau_{source}$); (d) acquiring the spectral measurements on a computerized platform; (e) fixing for the viewing angle and FOV by dedicated algorithms; (f) folding all members of the sequence by overlapping units on both axes (signal vs. energy); and (g) obtaining an accurate spectrum with reduced SNR.

It is another object of the invention to disclose a method as defined above, wherein at least one of the following is held true: (1) the semi-transparent transient source is selected from a group consisting of gas, vapor cloud, air current, plume, volcanic eruption, fire and a meteorite plume; (2) the semi-transparent transient source is phenomena in atmospheres of other solar system components selected from a group consisting of planet, solar prominence and atmosphere, gas clouds around smaller astronomical bodies and comet tails; (3) the semi-transparent transient source is phenomena in atmospheres of other solar system components selected from a group consisting of planets, including winds and clouds; (4) spectral measurements are conducted using a spectrometer selected from a group consisting of diffracting spectrometer and FTIR spectrometer; (5) shortest time limit of $\tau_{spectro}$ is determined by the spectral detector's integration time; (6) data collection capability is determined by the highest possible frequency of consequent spectral measurements; (7) data collection capability is determined by $\tau_{spectro}$ and by space limitations of the computerized platform; (8) signal-to-noise ratio (SNR) improvement is inversely proportional to the square root of the number of the measured spectra and is defined by the number of spectra collected within $\tau_{spectro}$; (9) on-board processing, comprising dedicated algorithms is configured for matching the viewing angles of different frames in the sequence; matching non-overlapping field-of-views of different frames; or folding spectra to reduce the amount of data; this is especially for space-based measurement where data is downlinked to ground station; (10) data folding is configured for determining distinct spectral features in the vicinity of semi-transparent transient sources, including clouds; (11) data folding is configured for determining distinct spectral features in the vicinity of semi-transparent transient sources, including distinction between cloudy and non-cloudy environments is made from the measured spectra; (12) spectral features of semi-transparent transient atmospheric source is measurable in parallel from one or more platforms, at one or more spectral domains, and at one or more spectral and imaging methods, and are configured to be analyze together to obtain at least one of a wider spectral coverage; a better SNR by collecting more data; a better 2D or 3D geometrical identification; and, an overlap of different imaging methods; (13) high-resolution spectral measurement is obtainable by a spectrometer having resolution above 200, including over 20,000; (14) high-resolution spectral measurement is obtainable by a method comprising steps of identifying a semi-transparent transient atmospheric or other source; acquiring the spectral measurements on a computerized platform; matching all members of the sequence by overlapping units on both axes (signal vs energy); obtaining accurate spectra of semi-transparent transient source and reference fields of view, with a reduced SNR; subtracting reference spectrum from measured semi-transparent transient source to obtain net absorption features of the source; extracting high resolution spectral features of source; and correlating spectral data with spatial resolution obtained from a second optical device; (15) high-resolution spectral measurement is obtainable by a method of providing for extraction of high-resolution spectral features, comprising at least one of the following analysis steps: comparing high resolution features with theoretical spectral databases to extract information about temperature and pressure conditions of atmospheric source; extracting the temporal and spatial change of the radiation source from Doppler analysis of the line width of high-resolution spectral features; and studying the internal structure of the semi-transparent transient source from the high-resolution spectral features, by using the curve of growth analysis for determining the vertical profile within the radiation source, up to an optical depth of about 1.

It is another object of the invention to disclose a system for spectral analysis of semi-transparent transient sources comprising a computer readable medium configured to process in methods as defined in any of the above.

It is another object of the invention to disclose a method system for accurate spectral analysis of semi-transparent transient sources and for high resolution spectral analysis of the time resolved, comprising a computer readable medium configured to process in methods as defined in any of the above.

Another object of the invention is to disclose a platform as defined in EXAMPLE I and schematically illustrated in FIG. 1.

Another object of the invention is to disclose a platform as defined in EXAMPLE II and schematically illustrated in FIG. 2.

Figure 3:
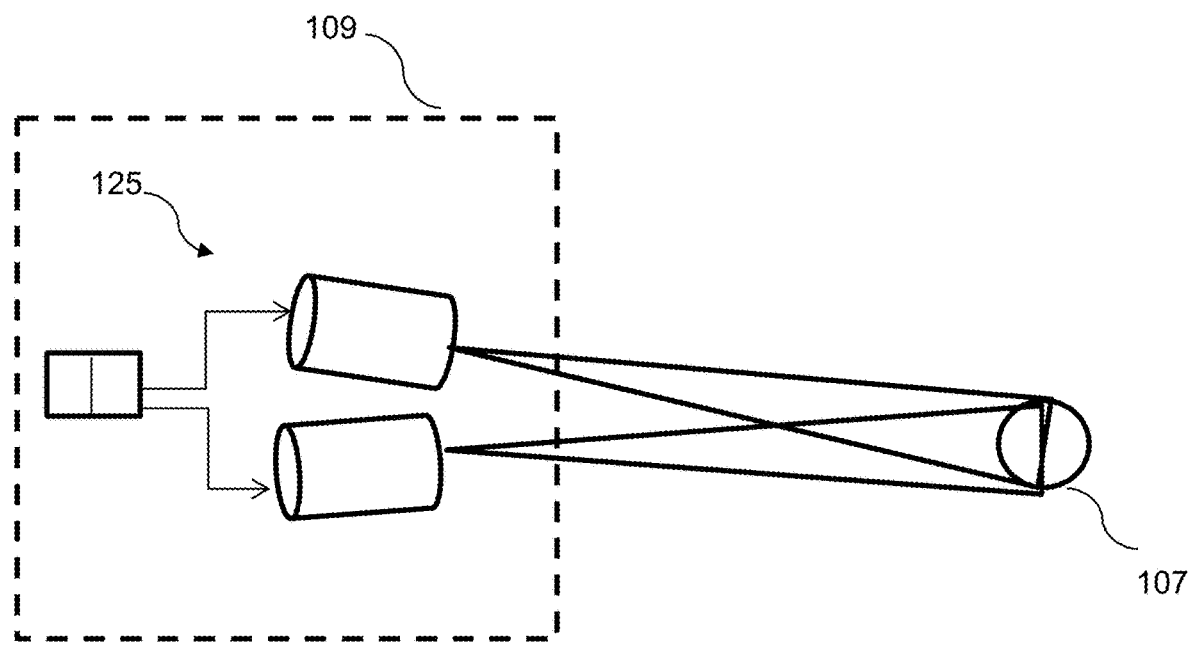
FIG. 3 is a schematic diagram of a bore-sighted pair of a spectrometer and of a second spectrometer or imager on a platform according to an embodiment of the invention.
Figure 3A:
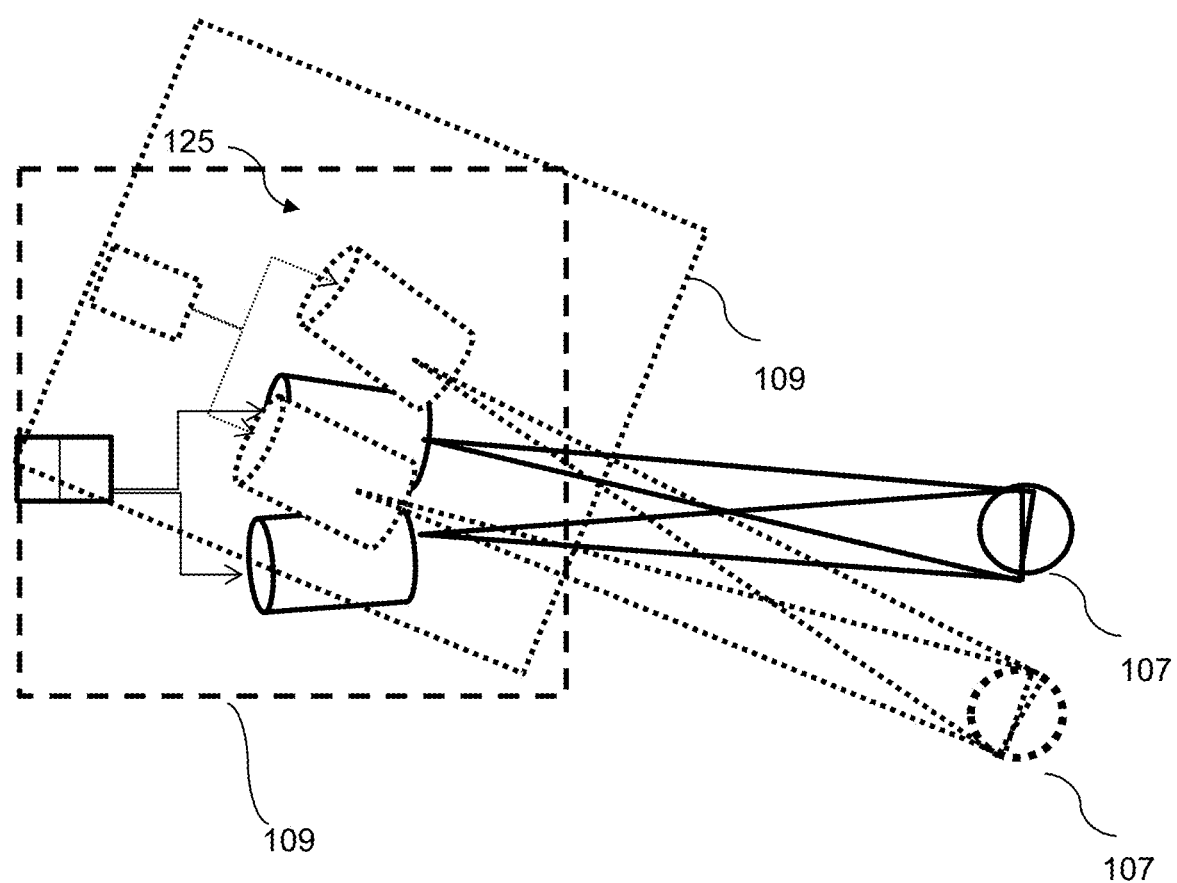
FIG. 3*a* is a schematic diagram of the platform with the bore-sighted pair, in two tilted configurations according to an embodiment of the invention.

Another object of the invention is to disclose a platform as defined in EXAMPLE III and schematically illustrated in FIG. 3.

Figure 4:
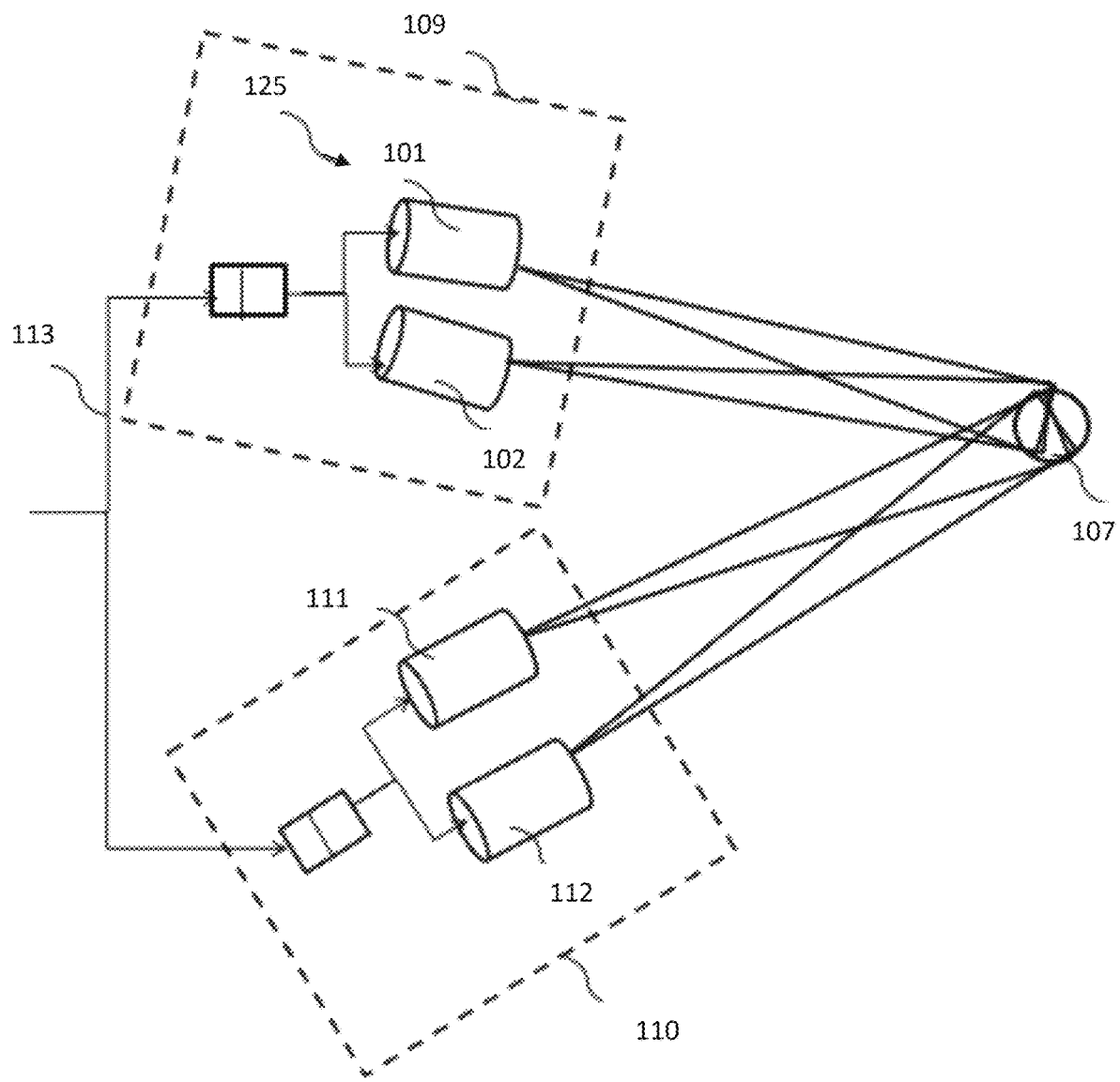
FIG. 4 is a schematic diagram of two bore-sighted pairs on two platforms for remote sensing according to an embodiment of the invention.

Another object of the invention is to disclose a platform as defined in EXAMPLE IV and schematically illustrated in FIG. 4.

Figure 5:
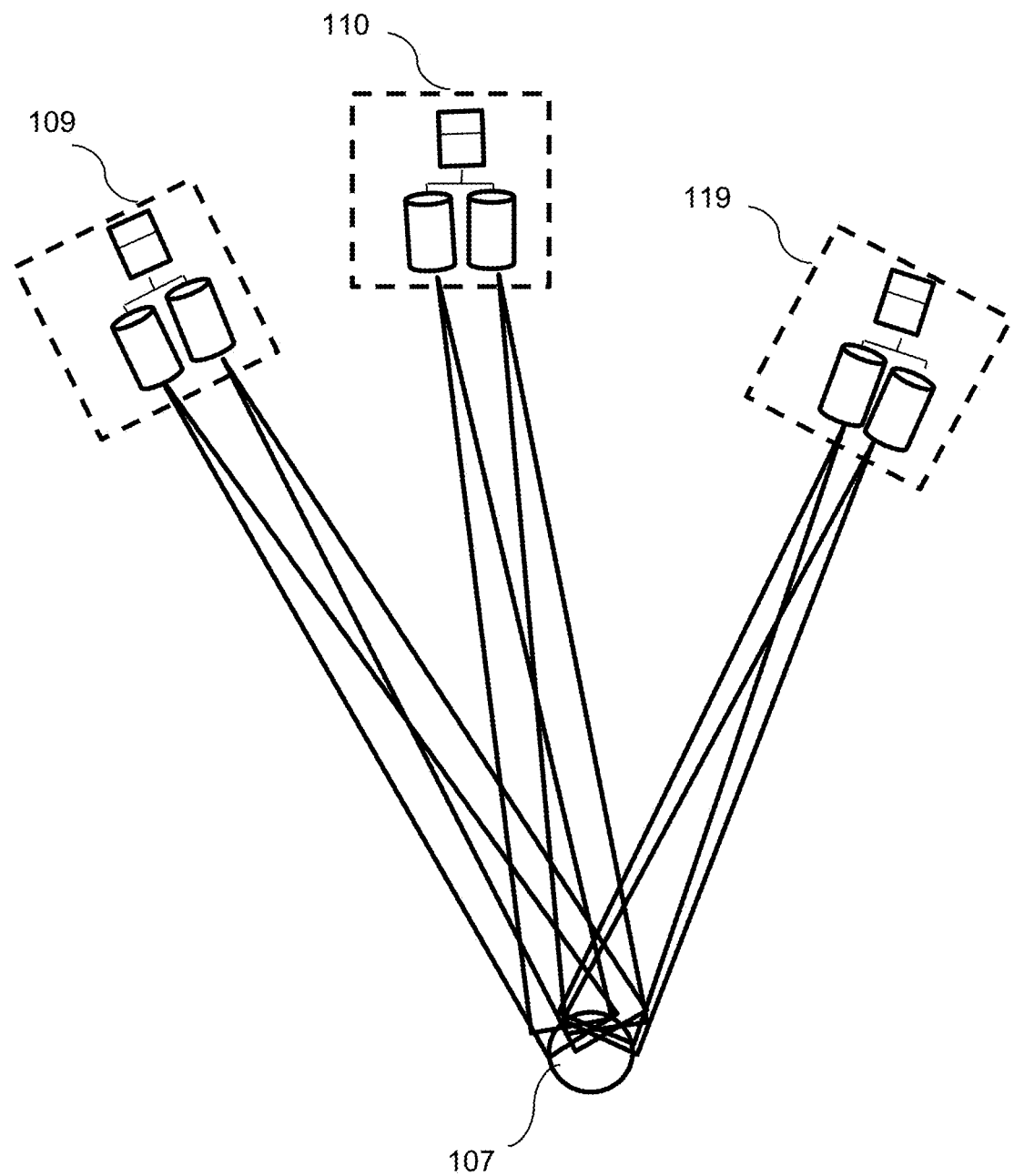
FIG. 5 is a schematic diagram of two bore-sighted pairs on three platforms for remote sensing according to an embodiment of the invention.

Another object of the invention is to disclose a platform as defined in EXAMPLE V and schematically illustrated in FIG. 5.

Figure 6:
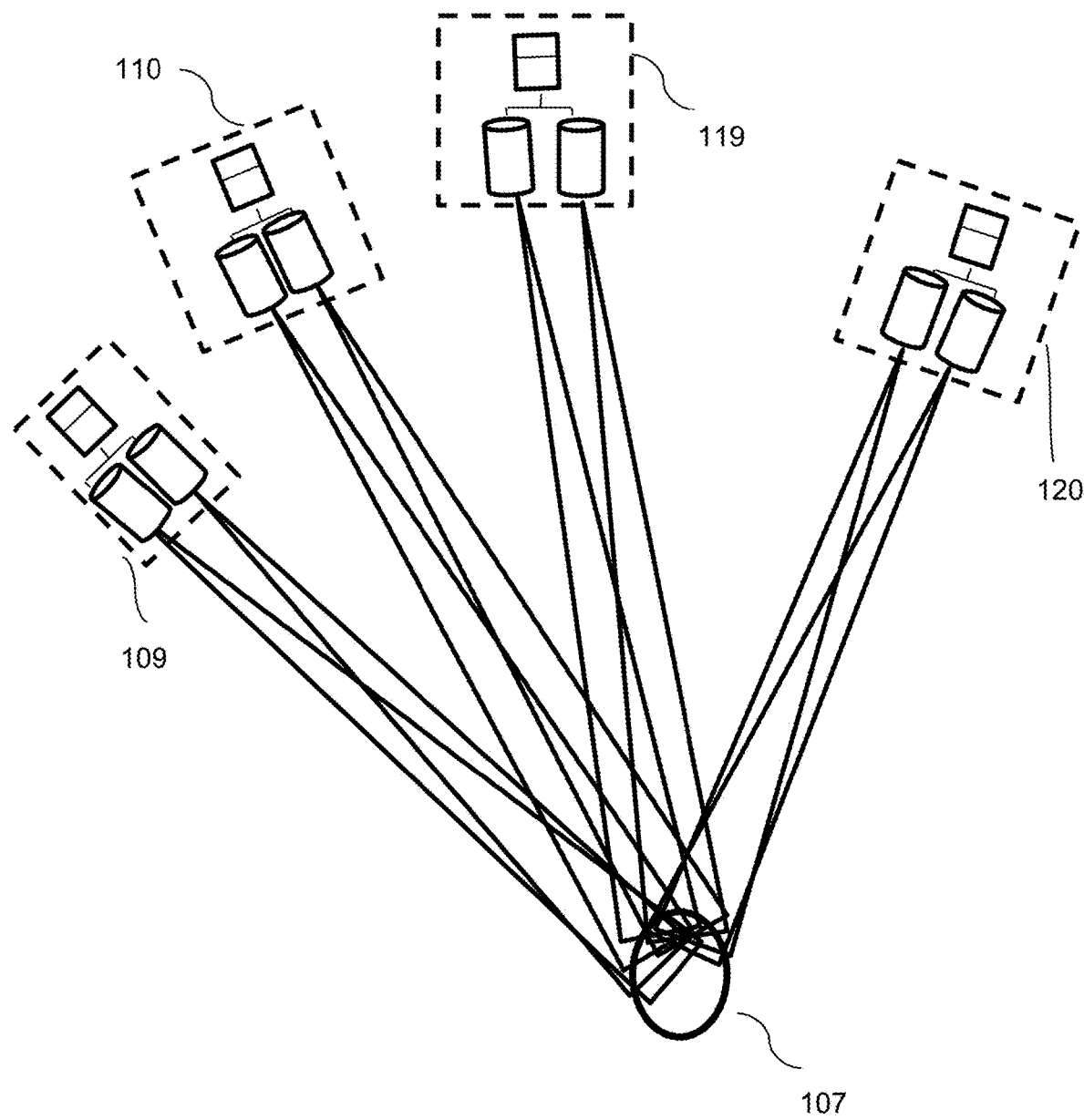
FIG. 6 is a schematic diagram of two bore-sighted pairs on four platforms for remote sensing according to an embodiment of the invention.

Another object of the invention is to disclose a platform as defined in EXAMPLE VI and schematically illustrated in FIG. 6.

Another object of the invention is to disclose a platform as defined in any of EXAMPLE I-VI, further comprising at least one member of a group consisting of means for combination of spectroscopy and imaging; means for combination of spectroscopy from two or more spectrometers and means for combination of spectroscopy and SAR.

Another object of the invention is to disclose a platform as defined in EXAMPLES I-XII and illustrated in FIGS. 1-9, respectively.

DETAILED DESCRIPTION OF THE PREFERRED EMBODIMENTS

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The term "remote sensing" refers herein after to conducting measurements at a distance from the measured source without physical contact with it.

The term "bore-sight" refers herein after to exact optic alignment of two or more instruments to the same field of view, as defined in this invention.

The term "bore-sighted pair" refers herein after to a spectrometer and another optic device, as defined in this invention, aligned optically to the same field of view.

The term "optic device" is selected from (i) one or more spectrometers, (ii) one or more imagers, and (iii) at least one spectrometer and at least one imager.

The term "spectral detectors" refers herein after to any suitable detectors, comprising at least one instrument with spectral capabilities, including inter alia diffracting, Fourier transform, prism spectrometers, hyperspectral spectrometer, etc. The term "imagers" includes the whole group of 'spectral detectors', and also sensors, cameras, CCDs, video, SAR, Focal plane arrays, imager including thermal imager, multi-spectral imaging instruments (e.g., cameras) and any combination thereof. The term "spectral domain(s)" refers herein after to any part of the electromagnetic spectrum which can be observed by the detectors, inter alia, UV, visible, SWIR, MWIR, FIR, Thermal IR, Far IR, microwaves, radio waves, etc.;

The term "transient sources" refers herein after to spectrally structured, continuously changing, diffuse radiation sources. The term "semi-transparent" refers herein after to sources for which optical depth of about 1. For the terminology of "optical depth", the term "about" specifically refers to a range between 0.05 to 5; or alternatively to a range between 0.5 to 2. The term "clouds" refers herein after to atmospheric-volume transient sources with distinct chemical and physical properties. The term "patches" refers herein after to surface-bound transient sources with distinct chemical and physical properties. The terms "same field of view" and "overlapping field of view" refer herein after to a known overlap field of view, such that the location of the field of view of one instrument with a smaller field of view diameter $D_0$ is well defined within the field of view of the instrument with the larger field of view diameter $D_1$ (see FIG. 2b).

The term "Source timescale" refers herein after to timescale for change in source geometric shape and is denoted by "$\tau_{source}$". The term "measurement timescale" refers herein after to timescale for measuring a frame by the spectrometer and spectrometer or imager, and is denoted by "$\tau_{spectro}$". The term "reference" refers herein after to reference measurement, which will serve in the analysis as the basis for comparison to the measurement of the source, thereby allowing one to isolate the unique spectral fingerprint of the source over its background, and to conduct radiative transfer calculations of radiative transfer in the source only.

The term "simultaneous" refers herein after to a concurrent observation separated in a short period of time, e.g., less than about 1 sec. The term "about" refers hereinafter, in a non-limiting manner, to a value being 50% greater or lower than the defined measure. The term "exact overlap" and interchangeably "overlapping" refers hereinafter to no more than about 0.1% change in the overlap of the FOVs measured from one or more platforms by one or detectors, nor during the time of observation.

The term "platform" refers in a non-limiting manner to any means for carrying, being attached to, containing, being in communication with or otherwise comprising at least one detector as herein defined. The term refers, in a non-limiting manner, to a carrying vehicle, such as a satellite, e.g., a miniature satellite; to a measuring or observing instrument, e.g., telescope, etc. Multiple detectors, e.g., each of which is different from the others, is utilizable in a single platform. As an example, both stationary (fixed) or movable (portable) platforms are utilizable. Platforms of the present invention are waterborne, airborne, and/or located in near and deeper space (atmosphere). Ground-based or ground-bound platforms, as well as vehicle-interconnected platforms are also utilizable. The size of such a platform is varied from several grams, to nanoscale (e.g., about 10 Kg or less), microscale (about 100 Kg or less), and over 100 Kg. the term also referring, still in a non-limiting manner, to multiple platforms, e.g., in one or more 2D or 3D configurations, arrays or clusters. As such, multiple platforms are utilizable in one (2D) or multiple (3D) geometrical planes. Still as an example, one first 2D or 3D cluster or array of platforms is utilizable in connection with at least one second 2D or 3D cluster or array of platforms.

The term "external light source" refers in a non-limiting manner to a light source which is not immersed within the semi-transparent transient source and its radiation, at any range of the electromagnetic spectrum, is transmitted through and/or absorbed within it.

The term "fluid" refers hereinafter to a flowing matter, including gas, liquids, solids particles, colloids, aggregates, being either inorganic, organic, living matter or a mixture the same, and any mixture and combination thereof.

The term "FOV" refers hereinafter to the field of view of an observation. The term "COG" refers hereinafter to the curve of growth analysis of spectral data. The term "SAR" refers here to synthetic aperture radar.

In the foregoing examples, the term "frame" refers herein after to a spectral measurement conducted by the spectrometer. The term "SNR" refers herein after to the signal to noise ratio of the spectral measurement. The term "data folding" refers herein after to averaging, with a complete overlap of axes, the data obtained from different spectral measurements, which may or may not be consecutive or of the same $\tau_{spectro}$. The term "simple average" refers herein after to the arithmetic average. The term "pointing knowledge" refers herein to the knowledge of the exact location of observation from at least two platforms.

Absorption & Emission Spectroscopy and Imaging of Clouds in Transit

The study of the chemistry of clouds is a key factor in understanding climate control by natural factors affecting cloud formation and evolution, such as marine aerosols, chemical cycles (e.g., the carbon cycle) etc. The common treatment of radiative transfer in clouds is currently provided useful by study of scattering, from which little information about their internal chemical structure can be obtained.

According to one embodiment of the invention, means and methods are disclosed to enable absorption, emission and transmission spectroscopy combined with imaging of clouds in transit. This technology is also useful for measuring other phenomena, including inter alia atmospheric plumes and wind currents, by observing them on a lightened background, i.e., the twilight skies; the sun, with a protecting cutoff filter; the moon; a ground light-source, etc.

Cloud observation requires an overlap between two spectral detectors or one spectral detector and one imager, because clouds are diffuse and constantly changing. Only exact overlap in field of view and possibly in magnification of simultaneous spectroscopic measurements and imaging (e.g. in visible light), will allow for an accurate analysis of the measured spectrum with respect to the cloud diffuse structure geometry. In this respect, the radiative transfer through a cloud's 'semi-transparent' layers, reveal the spectra of its components, leading to a better understanding of the cloud's inner structure and processes within.

Addition of an external light source to aforesaid configuration makes the spectroscopic measurement of the cloud ideal, because it allows for a source of blackbody radiation in the visible and other wavelengths and/or spectral domains to transmit through parts of a cloud, where its optical depth is about 1, to modulate the spectrum of the blackbody, and to reveal clouds' internal structure. Much similarly, the technology is further utilizable for observation through various atmospheric and/or astronomic phenomena, such as chimney plumes, wind currents, comet tails.

Wind Atmospheric and Space Motions: Emission Spectroscopy and Synthetic Aperture Radar Semi-transparent transient sources such as atmospheric wind currents and chimney plumes, comet tails and meteorites, display a gradient of chemical species, which is different from their surroundings and is rapidly changing in time. Fluid motions have spectral emissions at ambient or at higher temperatures than their environment, which can be used to characterize their chemical structures. According to yet another embodiment of the invention, fluid cloud motion, including wind atmospheric and space motions are enabled by methods of accurate temporal, spatial and spectral mapping of rapidly changing radiation sources with distinct spectral structure, in at least one spectral domain by exact spatial and temporal overlap of spectral; and other imaging methods from remote sensing on either fixed or on moving platforms. When spectral emission or blackbody radiation have a defined visible spectral range, such as for NOx, tracking of radiation source by aforesaid method described above for transiting phenomena, i.e. the combination of spectroscopic and visible imaging, will suffice.

According to another embodiment of the invention, applicable, inter alia, when there is no visible component to the emission, such as in wind currents, characterization of rapidly changing radiation source from an exact SAR train of images, simultaneous and on same FOV of the spectrometer, reveals details of the motion of the semi-transparent transient source, e.g., cloud, plume. In that respect, a characterization of the motions of fluids within semi-transparent transient source is obtained also from the Doppler shift of spectral lines, and contributes to the accuracy of the determination of rapidly changing radiation source.

A Cluster of Moving Platforms: Spectroscopy and Imaging in Either Same or Different Spectral Ranges As much as the combined measurement is provided by one or more fixed platforms, it is alternatively or additionally provided by one or more moving platforms. Each of which, part or all of aforesaid platforms are enabled to operate in a manner selected inter alia from a singular operation; multiple operations; concurrent operations; a concerted operation; a non-coordinated operation; a feedback operation; manual, semiautomatic, automatic, or otherwise computer-governed operation; a cascaded operations; at least one, either 2D or 3D array of two or more platforms, each of which is either online or offline operated, and any combination thereof.

It is acknowledged in this respect that singular platform, e.g., a nanosatellite, a Cube-Sat or an airborne drone, is configured and enabled to carry significantly less volume or weight than the accumulated weight or volume carried by multiple platforms.

It is hence according to another embodiment of the invention, where concerted operation is provided useful for measuring semi-transparent radiation source(s) by more spectroscopic and imaging instruments than a single platform can carry and can allow for a wider spectral and imaging characterization by exact temporal, spatial, overlap in FOV and possibly magnification, of the spectroscopic measurement and imaging, as described above for a single platform.

It is further acknowledged in this respect that such concerted operation provided for either an additive or a synergic concurrent measurement of said radiation source(s). Such a synergy is provided, inter alia and in a non-limited manner, by providing much more accurate measurement(s) with an increased resolution; much shorter operation-time; adding significantly more degrees of freedom in source(s) allocation, as well as providing for assembly, maneuver, operation, response time and accuracy of multiple platforms arranged, e.g., in one or more 2D or 3D configurations, arrays or clusters.

The complication of a fixed concerted system is the introduction of the viewing angle which should be corrected for. This can be done only by using dedicated algorithms, since the effect of different viewing angles cannot be overcome by hardware. The stabilization of the FOV in a moving system, measuring from either one or from several platforms, allow for no more than about 0.1% change in the overlap of the FOVs measured from the different platforms, nor during the time of observation. Additionally, or alternatively, it allows for simultaneous observation.

The following description is provided, so as to enable any person skilled in the art to make use of said invention and sets forth the best modes contemplated by the inventor of carrying out his invention. Various modifications, however, are adapted to remain apparent to those skilled in the art, since the generic principles of the present invention have been defined specifically to provide a device for time-resolved detection and characterization of semi-transparent weak spectrally structured, continuously changing, diffuse radiation sources from multiple platforms and method for doing the same.

It is in the scope of the present invention to disclose means and methods to characterize spectrally structured continuously changing diffuse radiation sources, such that a combination of imaging and spectroscopy allows to define a point of reference for the spectral measurement, so as to identify distinct locations on the diffuse source's surface and inner structure up to optical depth of about 1. The choice of spectral lines, their measurement method and analysis to reveal the inner structure of the semi-transparent transient source allows to study diffuse radiative sources such as clouds, etc.

Reference is now made to FIG. 1. FIG. 1a presents a schematic diagram of a telescope 103 to which a beam-splitter 104 is attached. The beam splitter divides the radiation arriving from the source 100, between a spectrometer 101 and a second spectrometer or imager, so that it allows for simultaneous viewing of the same field of view by spectral and by spectral and/or imaging methods. FIG. 1b presents an 8" telescope to which a bino-viewer is attached, with an astronomical camera in one eyepiece and the optic fiber of a vis/Nir spectrometer, held by e.g., an adaptor presented in FIG. 1d attached to the other. FIG. 1c presents a close-up view of the same.

Figure 2A:
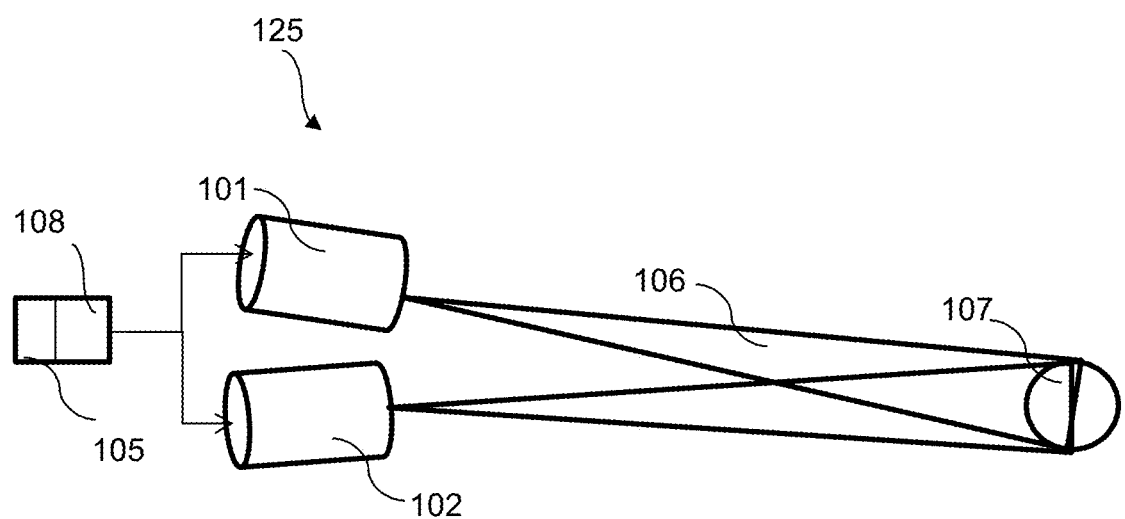
FIG. 2*a* is a schematic diagram of a bore-sighted pair of a spectrometer and of a second spectrometer or imager with alternate or simultaneous control.
Figure 2B:
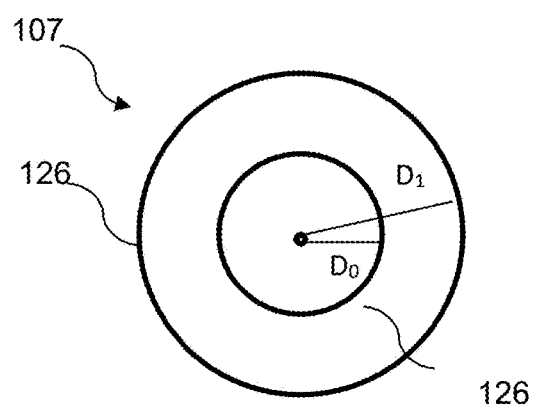
FIG. 2*b* is a schematic of the fields of view overlap at radius Do according to an embodiment of the invention.

Reference is now made to FIG. 2a, where instead of a single optic path, as presented in FIG. 1, there are two separate instruments, a spectrometer 101 and a second spectrometer or imager 102 forming a bore-sighted pair observing the same field of view. The optics required for such configuration is not described in this embodiment, only required is that the angles of viewing 106, converge onto the same field of view 107. The control of the units 101 and 102 is done by control unit 105, which operate alternately in timescales $\tau_{spectro}$ shorter than $\tau_{source}$, or by control unit 108, which operates simultaneously, both operate in timescale for which $\tau_{spectro}$ shorter than $\tau_{source}$. FIG. 2b depicts the importance of the overlap of the fields of view such that it is known where $D_0$, the radius of the field of view of one instrument, covers the radius $D_1$ of the field of view of the second instrument. It is well in the scope of the invention wherein the control unit 105 is optional module of the platform, namely the platform may be free of such a processing module.

Reference is now made to FIG. 3, presenting the bore-sighted pair 125 of spectrometer 101 and of second spectrometer or imager 102 on platform 109 for remote sensing, which is any of hand-held platform, ground vehicle, marine platform, airborne and space vehicle.

Reference is now made to FIG. 19, presenting at least two spatial configurations of platform 109 with bore-sighted pair 125, one drawn with continuous lines and one drawn with dashed lines. The separate configurations are obtained by tilting the platform into observing the same or different fields-of-view 107. Pointing knowledge is determined by control unit 108.

Reference is now made to FIG. 4, presenting two platforms 109 and 110 for remote sensing, each carrying a separate bore-sighted pair 125 of spectrometer 101 and of second spectrometer or imager 102 on platform 109, and a spectrometer 111 and a second spectrometer or imager 112 on platform 110 as presented in FIG. 3, or two instruments on the same optical path as presented in FIG. 1, pointed at the same field of view 107 and controlled by unit 113 to provide for concerted operation control, within a timescale where $\tau_{spectro}$ is shorter than $\tau_{source}$.

Reference is now made to FIG. 5, presenting three platforms 109, 110 and 119 for remote sensing, each carrying a separate bore-sighted pair 125 as presented in FIG. 3, or two instruments on the same optical path as presented in FIG. 1, pointed at the same field of view 107 and controlled by unit 113 to provide for concerted operation control, within a timescale where $\tau_{spectro}$ is shorter than $\tau_{source}$. The combination of three platforms allows for 2D location determination of said radiation source.

Reference is now made to FIG. 6, presenting four platforms 109, 110, 119 and 120 for remote sensing, each carrying a separate bore-sighted pair 125 as presented in FIG. 3, or two instruments on the same optical path as presented in FIG. 1, pointed at the same field of view 107 and controlled by unit 113 to provide for concerted operation control, within a timescale where $\tau_{spectro}$ is shorter than $\tau_{source}$. The combination of four platforms allows for 3D location determination of said radiation source.

Figure 7A:
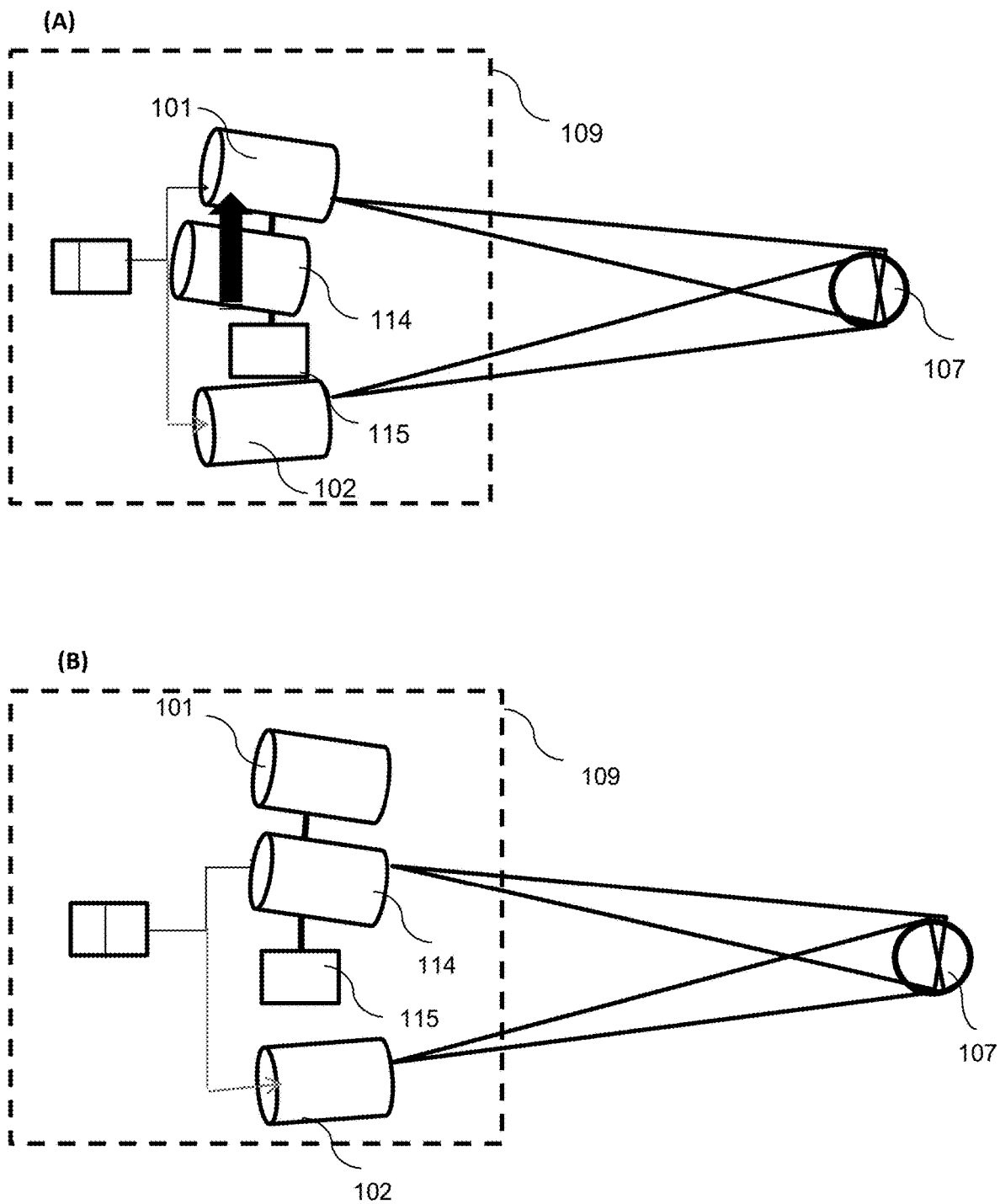
FIG. 7 is a schematic diagram of a backup system for the spectral detector according to an embodiment of the invention.
FIG. 7*b* is a schematic diagram of the measurement method to observe source and reference according to an embodiment of the invention.

Reference is now made to FIG. 7a, presenting the spectrometer 101 and the second spectrometer or imager 102 and the back-up spectrometer 114. FIG. 7a (upper illustration A) presents the situation where the back-up spectrometer 114 is outside the main optic path of the bore-sighted pair 125. FIG. 7a (lower illustration B) presents a situation where spectrometer 101 fails, and the back-up spectrometer 114 is pushed by motor 115 into the optical-path in place of spectrometer 101, now to be aligned with second spectrometer or imager 102.

Figure 7B:
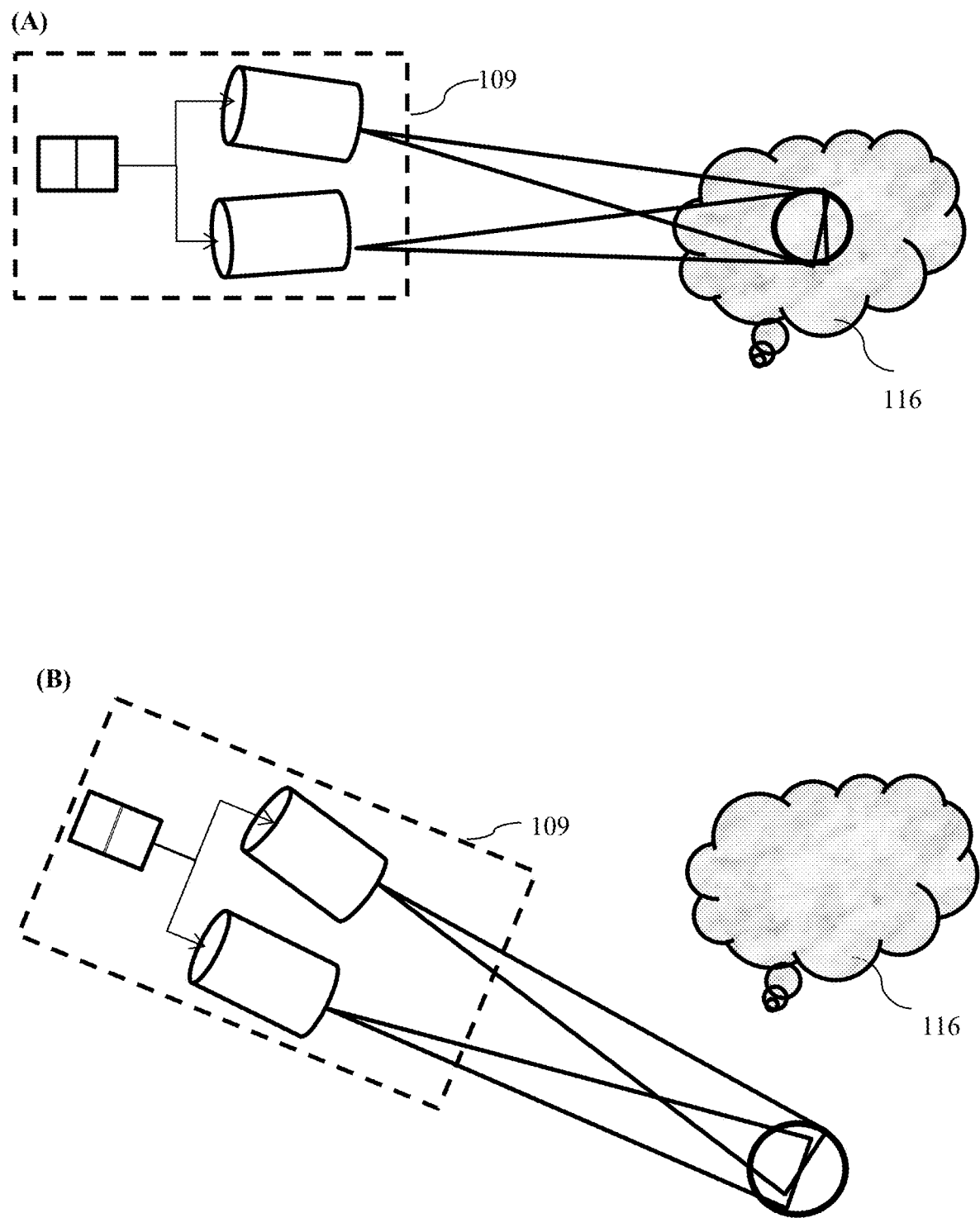
Figure 8:
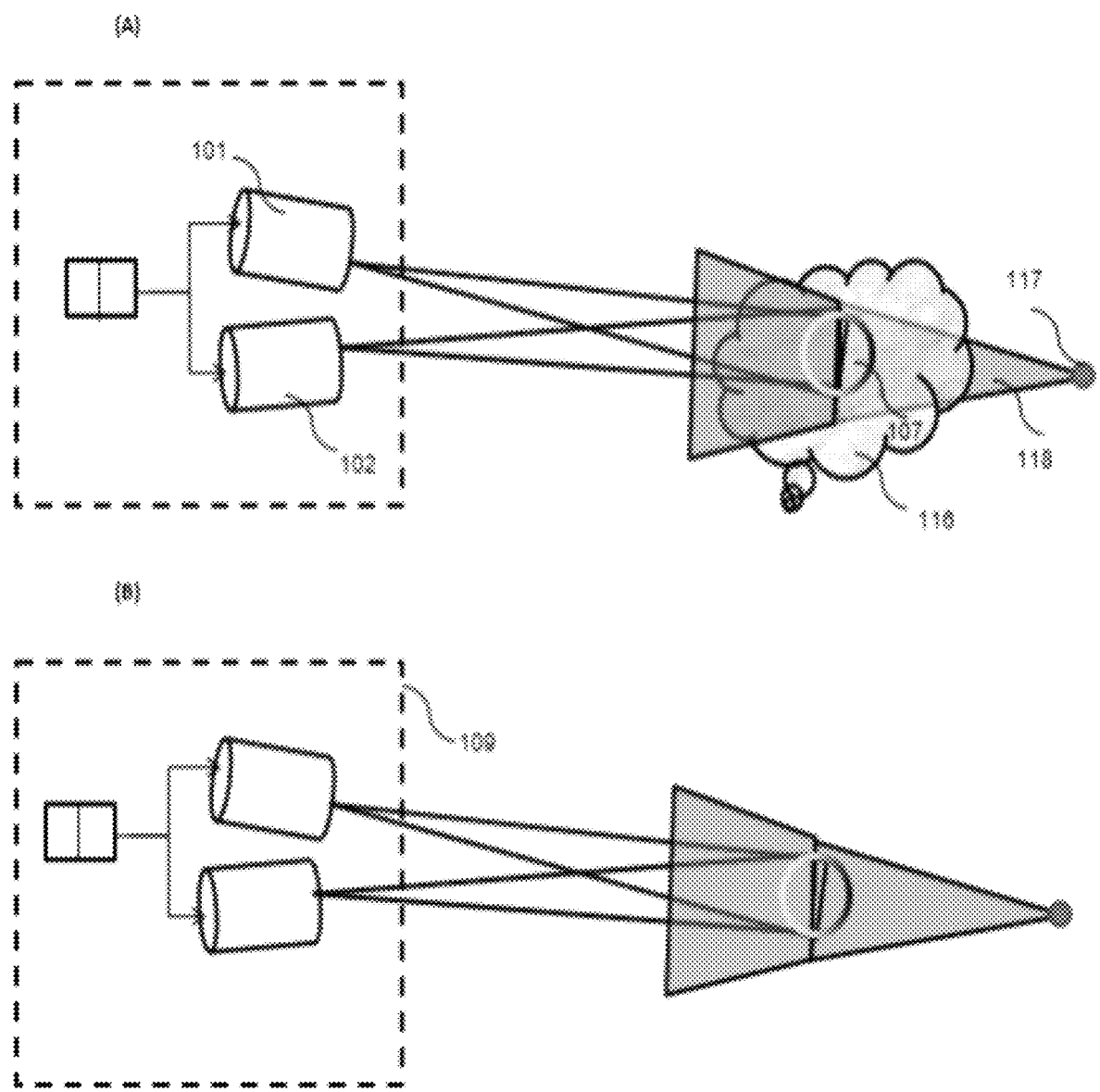
FIG. 8 is a schematic drawing of direct spectroscopy and imaging of the semi-transparent transient source and of a reference field-of-view towards an external radiation source according to an embodiment of the invention.

Reference is now made to FIG. 7b, presenting the bore-sighted pair 125 on a platform 109, pointed at a semi-transparent transient source 116. At least one measurement of the source 116 is taken from bore-sighted pair 125 within a timescale $\tau_{spectro}$ shorter than $\tau_{source}$, and at least one measurement of a reference field-of-view 128, for later processing on unit 105, or by downlinking to a ground station, subtracting the reference 128 from the folded measurement(s) of the source 116 for a radiative transfer calculation of the semi-transparent transient source 116. The overlap of the spectral and other spectral or imaging data in the processing unit 105 allows to study the radiative transfer through the source 116 and compare it to its spatial arrangement.

Reference is now made to FIG. 8a, presenting the bore-sighted pair 125 on platform 109 used for observing the semi-transparent transient source 116 when observing its contents by direct spectroscopy, using an electromagnetic light beam of an external source 118, natural or artificial, whose radiation penetrates through source 116 and arrives at spectrometer 101 and second spectrometer or imager 102. The transmitted electromagnetic radiation beam 118 allows for direct spectroscopy of semi-transparent volumes within the source 116. FIG. 8b presents the same, but pointing at external source 117 with no semi-transparent transient source 116 in between as a reference measurement for the source 116 measurement.

Figure 9:
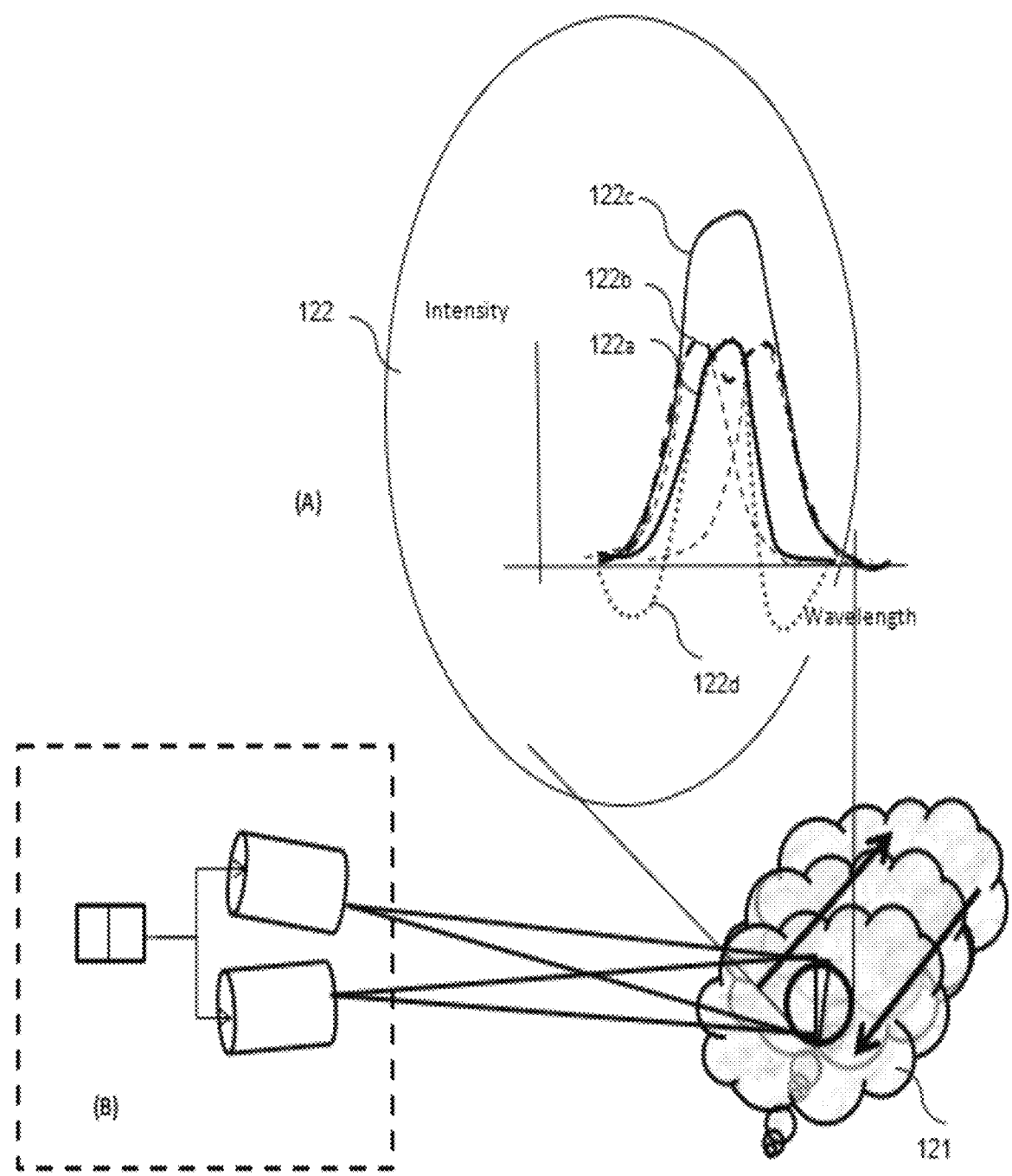
FIG. 9 is a schematic diagram of the method of observing the spectral structure and image of a semi-transparent transient source in motion, and possible spectral profiles of the measured spectral line in the inset according to an embodiment of the invention.

Reference is now made to FIG. 9, presenting the mode of observation of the motion 121 of a semi-transparent transient source 116 from bore-sighted pair 125 mounted on platform 109. Motions in the line of sight may be detected by the change in apparent line shape due to Doppler shift 122 of the line during motion inside source 116 and depends on the resolving power of the spectrometer. Possible configurations are selected inter-alia from: 122a single absorption line: no motion or motion to a single direction; 122b resolved absorption of forward and backward motion; 122c non-resolved absorption of forward and backward motion; 122d emission moving forward resulting in blue shift; non-resolved absorption; and emission moving backward resulting in redshift. Any of these or more than one mode may be observed. The overlap of the spectral and other spectral or imaging data in the processing unit 105 allows to study the radiative transfer through the source 116 and compare it to its spatial arrangement.

Reference is now made to FIG. 10, presenting the platform 109 and/or the bore sighted pair in a planetary orbiting configuration, which are tilted in at least one grazing angle to the planetary surface 123, such that a deeper slice of the planetary atmosphere 124 is observed, enhancing the absorption of the gaseous species involved. In FIG. 10a is presented the source 116 in the planetary atmosphere 124; in FIG. 10b the source 116 is lighted by an external source 117, thus allowing for direct spectroscopy and enhancing in more than one way the observed source 116. A plurality of tilt angles yields a profiling of the said species in the planetary atmosphere 124 and allows to measure also a reference field of view without the source 116.

Figure 10A:
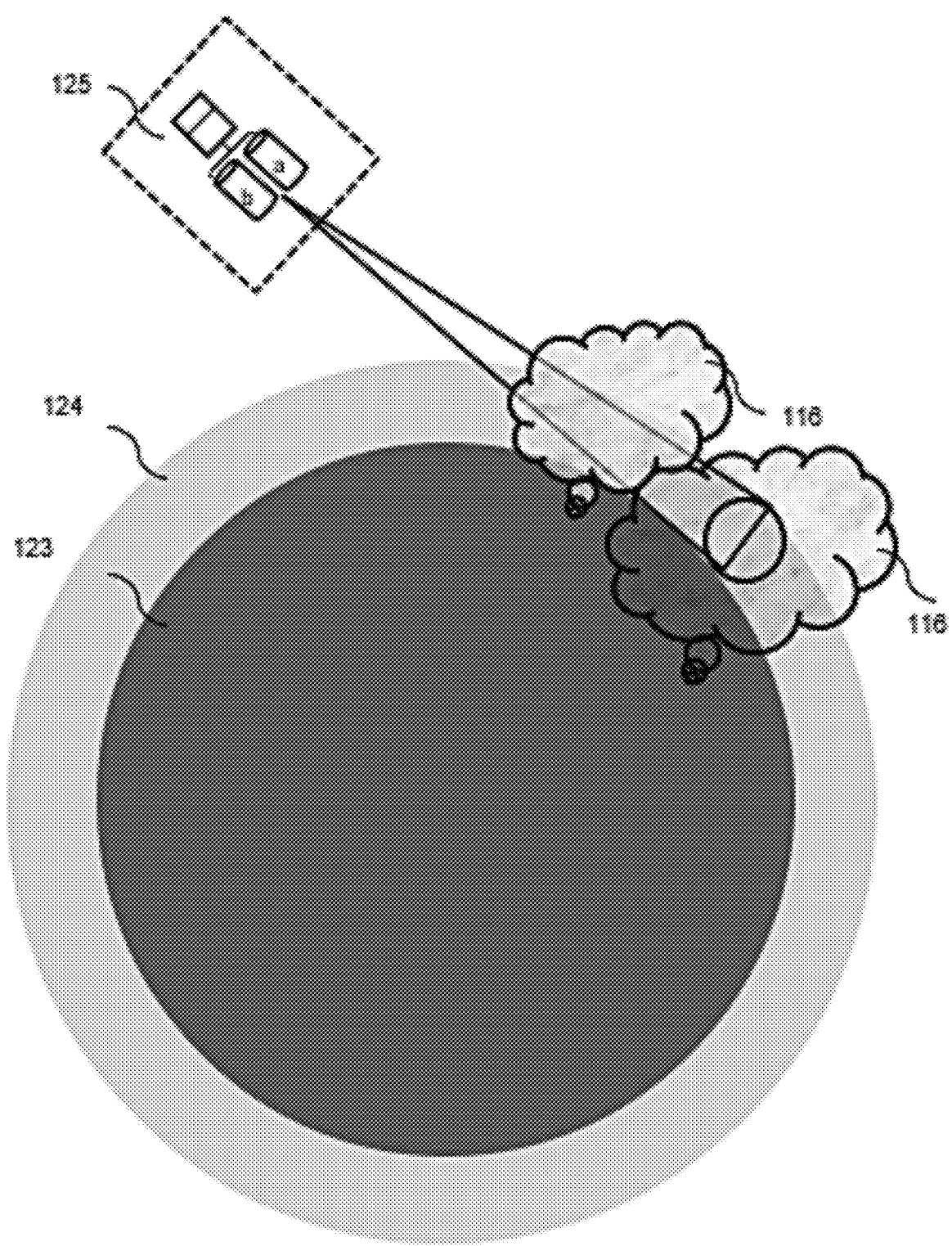
FIGS. 10a-10b are schematic diagrams of the method of observation of semi-transparent transient sources by tilting the platform or bore-sighted pair off of nadir according to an embodiment of the invention.
Figure 10B:
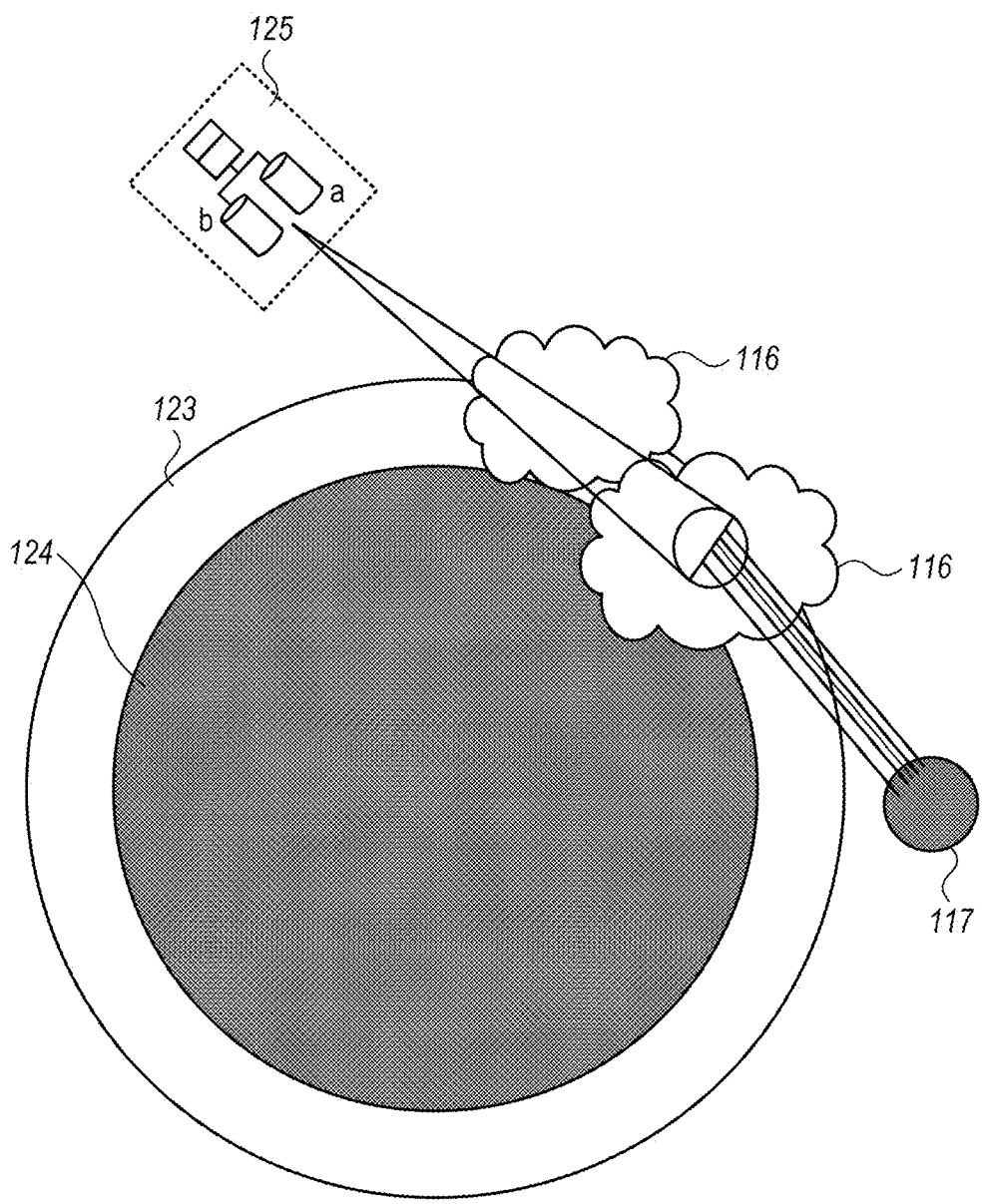
Figure 10C:
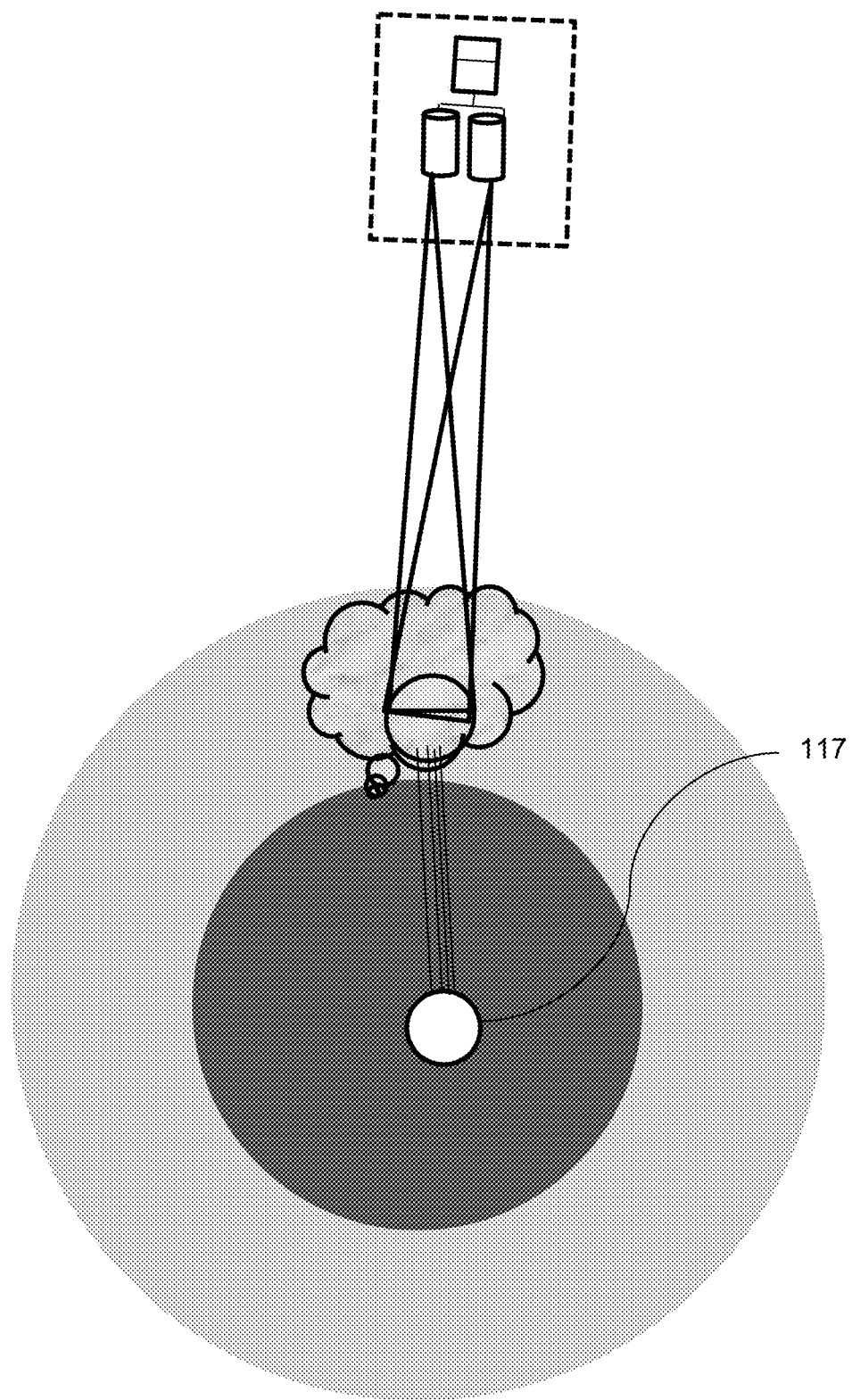
FIGS. 10c and 10d are schematic diagrams of the measurement method towards the planetary surface, with an external light source or towards another platform according to an embodiment of the invention.
Figure 10D:
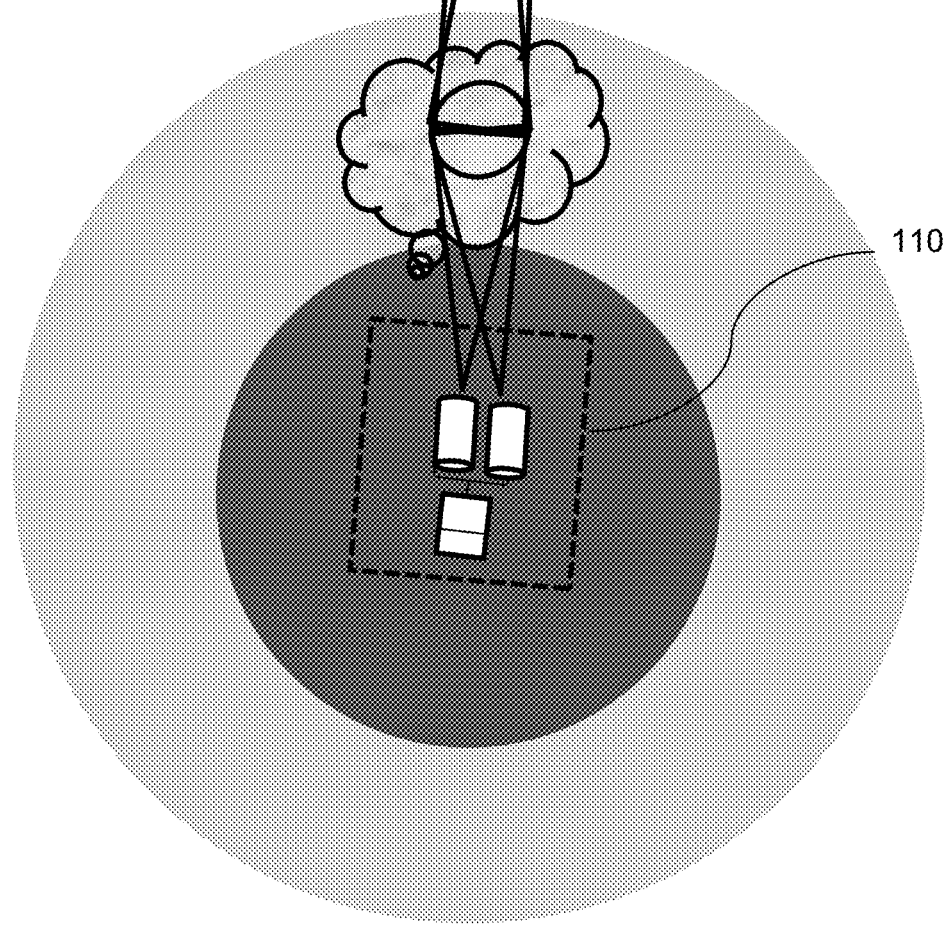

Reference is now made to FIG. 10c, presenting the platform 109 and/or the bore sighted pair in a planetary orbiting configuration pointed at the planetary surface 123, such that radiation originating in an external light source 117 penetrates through the semi-transparent transient source as to allow direct spectroscopy of said source in wavelength range of source in FIG. 10c. In FIG. 10d, on the planetary surface there is an identical bore-sighted pair which allows for measurement of chemical gradients about the semi-transparent transient source, by obtaining information from two opposite directions. The second platform can also be not attached to the surface, such that the observation is done from a different angle in space, as in the combination of FIG. 10b and FIG. 10d.

Figure 11:
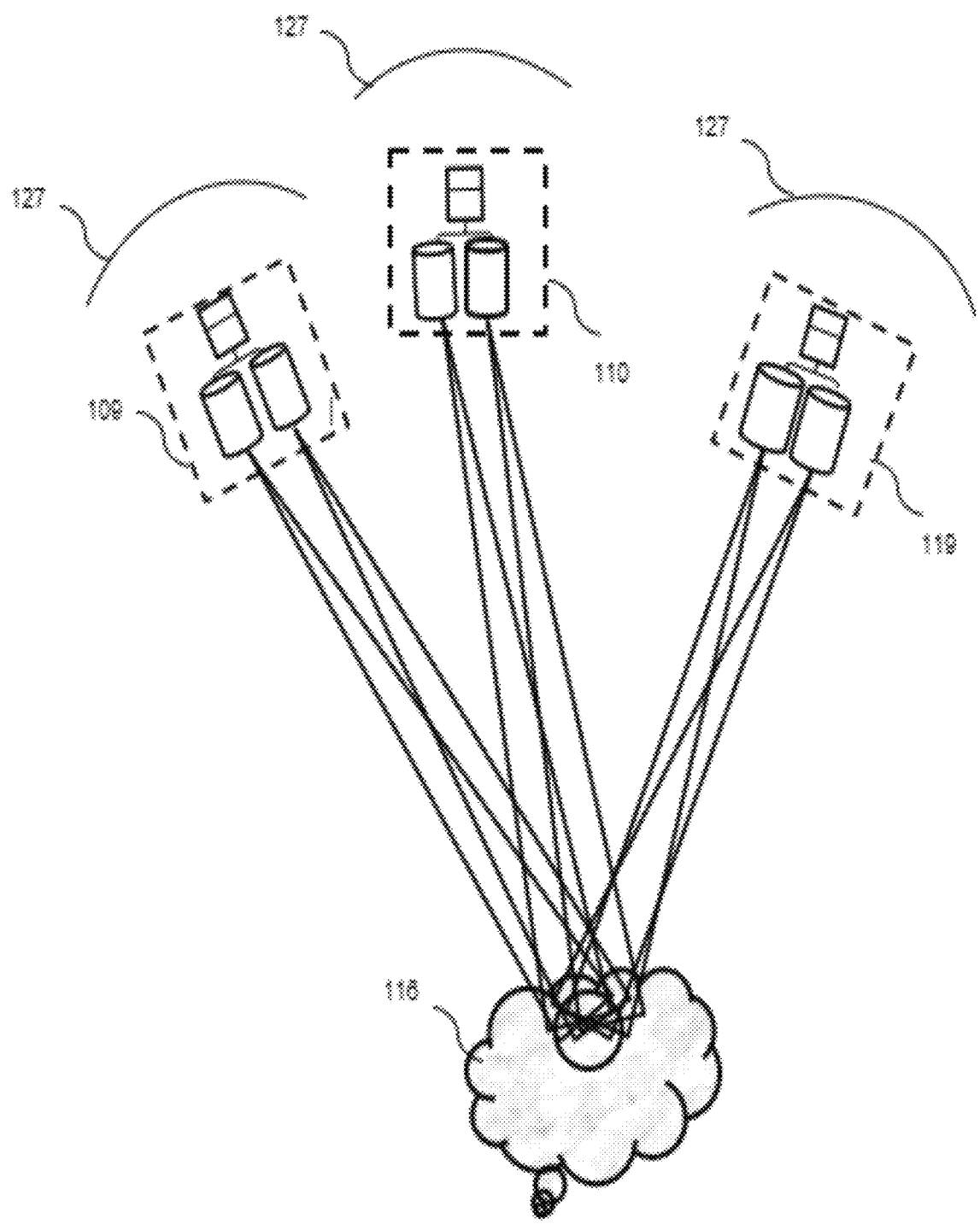
FIG. 11 is a schematic diagram of the pointing knowledge required for observing the semi-transparent transient source from multiple platforms.

Reference is now made to FIG. 11, presenting a three-platform formation, 109, 110 and 119, as an example for a multiple platform configuration. In order for the three bore-sighted pairs to act concertedly, the pointing knowledge 127 is crucial and allows for overlapping the spectral and the imaging data. This enables repeating each measurement as many times as there are platforms, thus acquiring more data in every measurement round. An addition of several measurements in a total time scale of $\tau_{spectro}$ shorter than $\tau_{source}$, allows for higher SNR.

Figure 12:
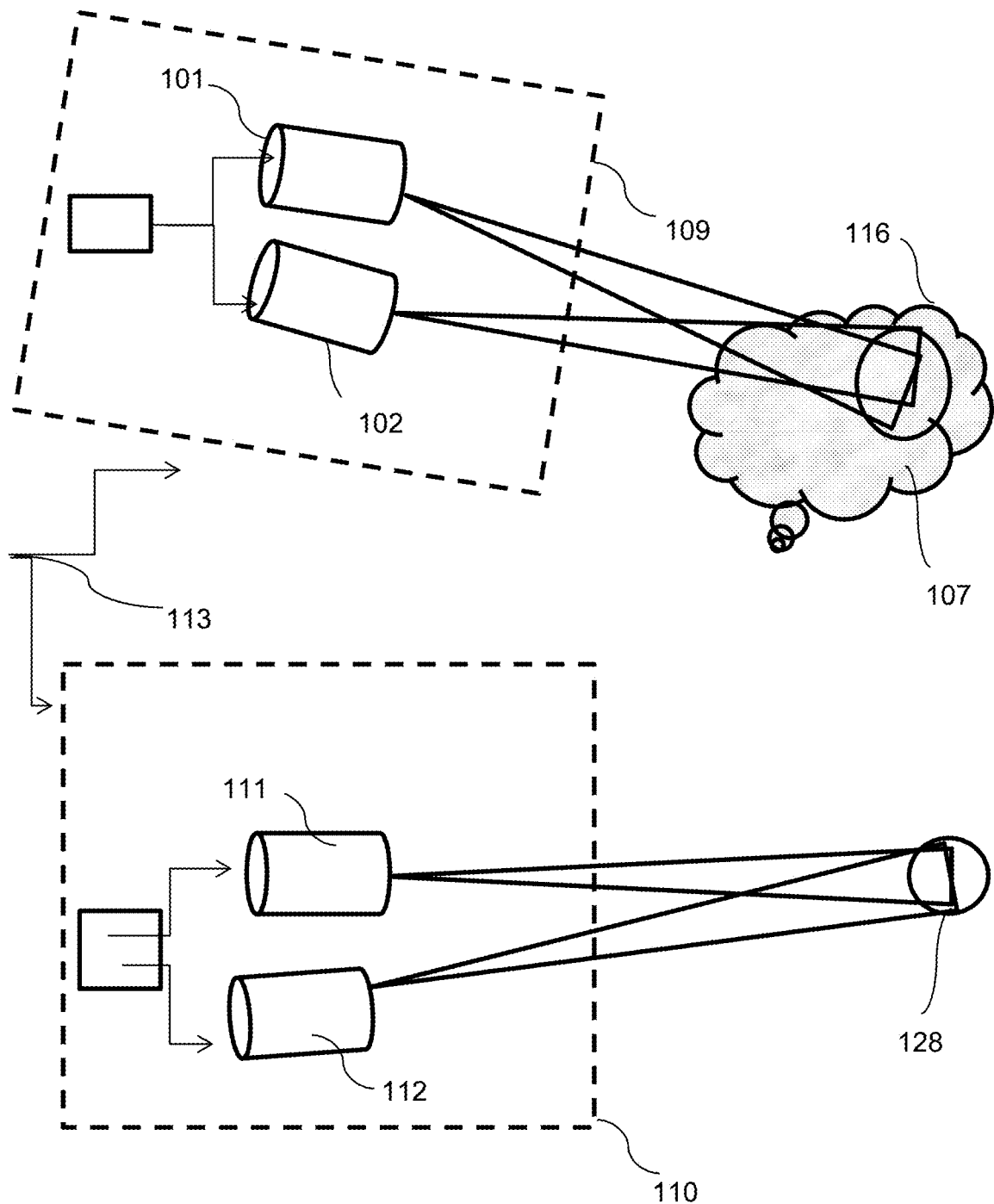
FIG. 12 is a schematic diagram of two platforms according to an embodiment of the invention.

Reference is now made to FIG. 12, presenting two platforms 109 and 110, measuring simultaneously the source 116 and the background 128 with no source using different tilt angles of platforms 109 and 110 or of the bore-sighted pairs mounted on them. In this configuration, less measurements of the source are taken at the same time but the reference is measured simultaneously and at the same place during the motion of the platforms.

Figure 13:
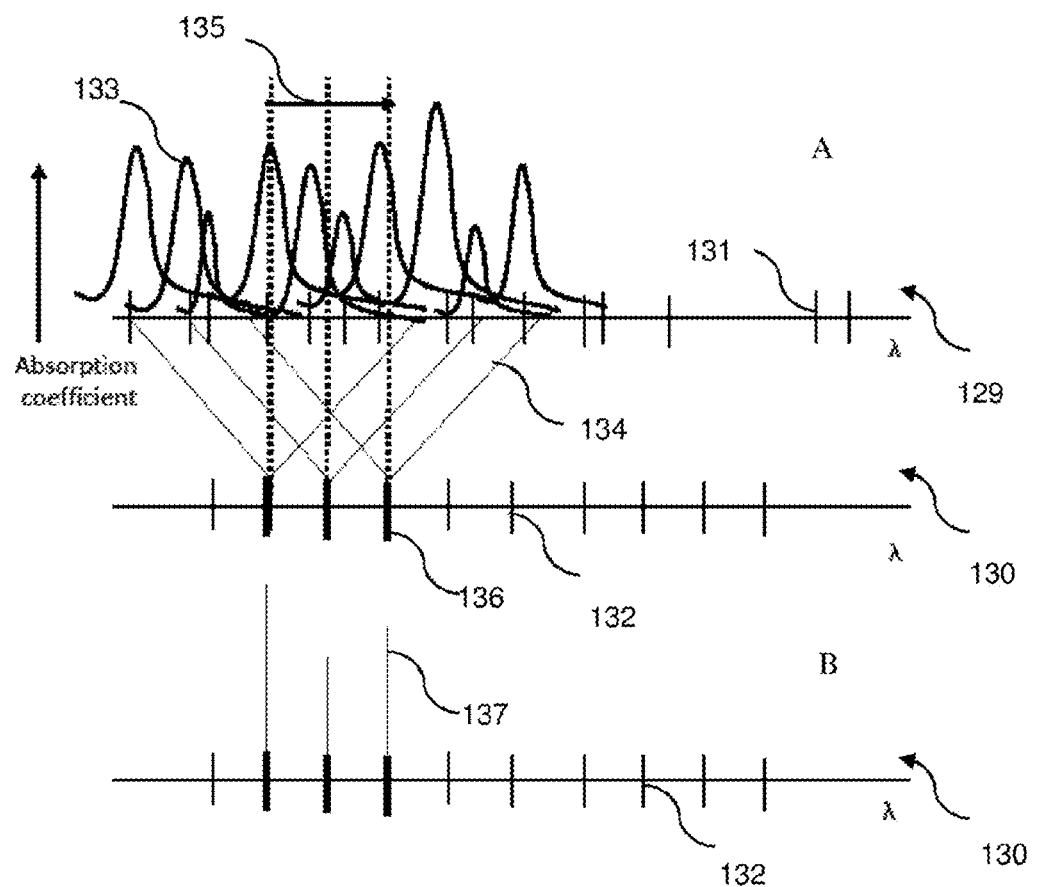
FIG. 13 is a schematic diagram of the window method to extract spectral data from databases such as HITRAN for accurate energy conserving radiative transfer calculations according to an embodiment of the invention.

Reference is now made to FIG. 13, presenting the method of the window extraction of spectral data from databases such as HITRAN for accurate energy conserving radiative transfer calculations. Two wavelength axes are important for this calculation: the wavelength list of the HITRAN (or any other) database 129, and the wavelength list of the calculation wavelength points, 130. In wavelength axis 129 appear the wavelengths for which there is spectral data in the database, 131. Those depend on referenced measurements that create the database (Rothman, L. S, 2013 *Journal of Quantitative Spectroscopy and Radiative Transfer*, Vol. 130, p. 4-50). On the calculation point axis 130, the wavelength points 132 are chosen equally every defined wavelength difference, and serve as 'wells' into which the spectral data is 'poured'. The database parameters are used to calculates the spectral line structure for the given P, T, C parameters of the calculation. Line profiles 133 are calculated and their wing contribution at the relevant calculation wavelength points 136 is determined. The contribution distance of the lines 134 is determined before the calculation, and thus the 'wells' 136 add up the contributions from all adjacent lines, which can be included in the calculation of the specific calculation points 136. The lines are read in order of their appearance in the database list 135. The total absorption 137 which is added up from all contributions to each wavelength point 136 is taken into consideration for the radiative transfer calculation and thus, reduces tremendously the amount of data treated in every calculation. Since the P, T, C condition is iterated for in each calculation of the radiative transfer, this process is repeated in every round, as the line profiles 133 change.

Figure 14:
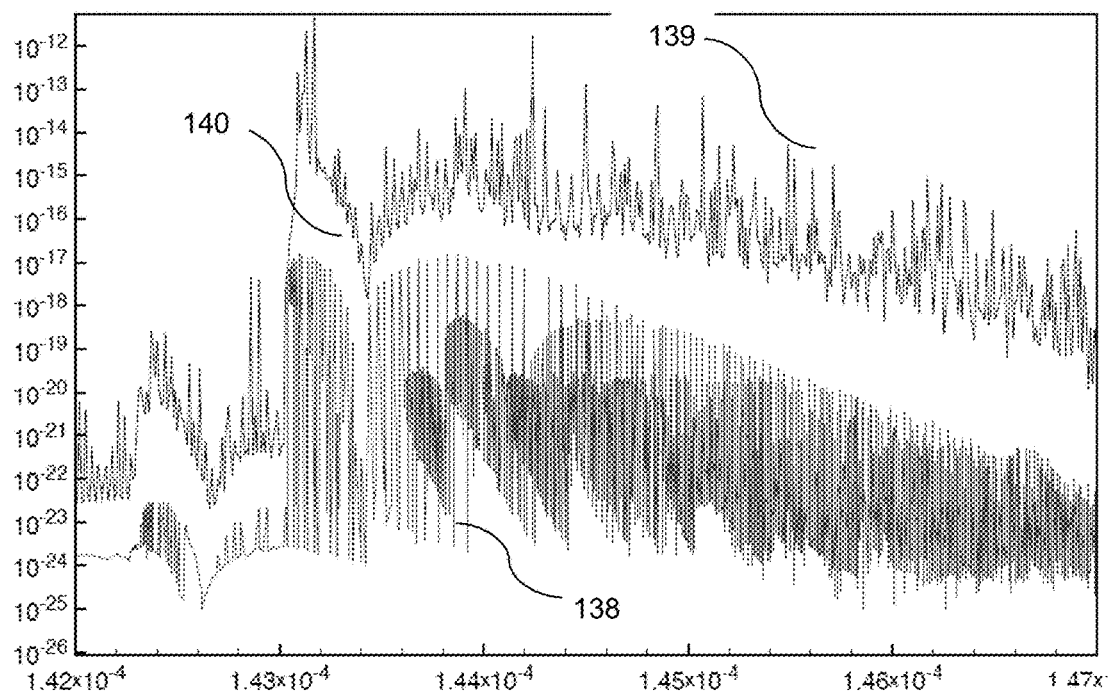
FIG. 14 is a window averaged absorption coefficient dependency on wavelengths, raw data and calculated with window as compared with reference transmission measurement, namely 'Absorption by CO2 between 6600 and 7125 $cm^{-1}$ (1.4-µm region) as disclosed below according to an embodiment of the invention.
Figure 14:
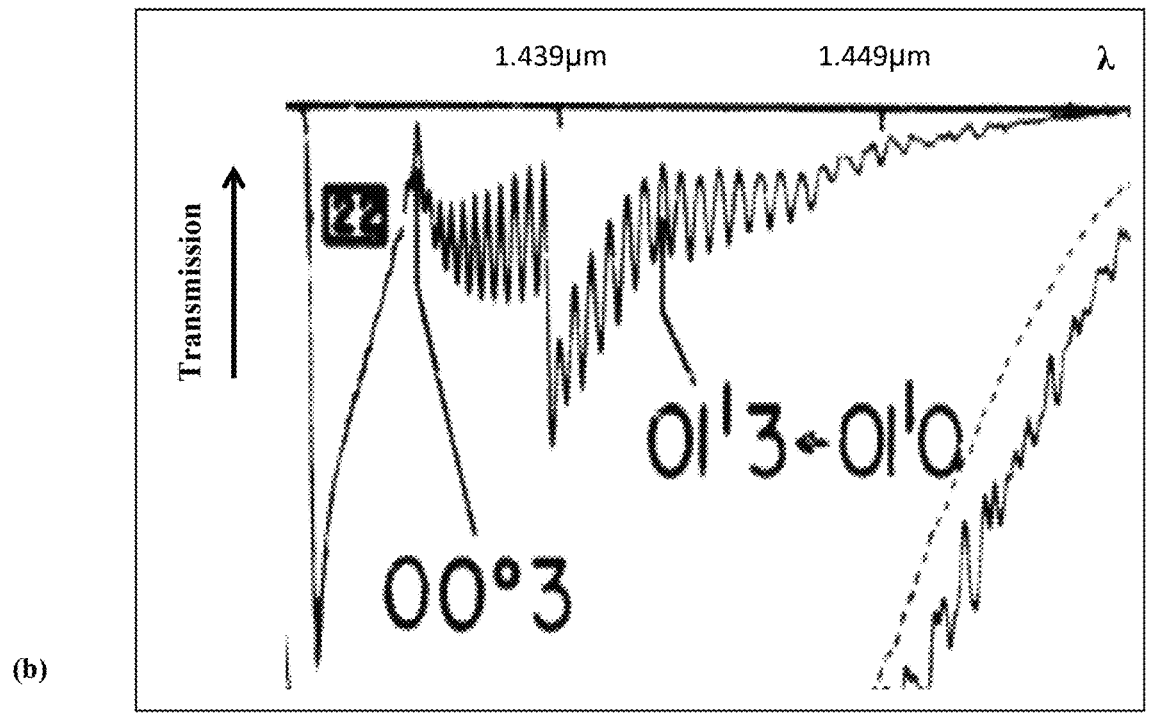

Reference is now made to FIG. 14a, presenting the calculation results for the 1.4 μm band of $CO_2$ 140, comparing the raw data as extracted from the HITRAN2012 database 138 and after the window calculation 139 (288K, 1 atm). The general trend of the band shape 140 is conserved, and the wing contributions of adjacent spectral lines form a continuum in the background. This shows the applicability and reproducibility of the real spectrum with the window method. FIG. 14b presents a transmission spectrum of the same band 140 measured at 296K and 1 atm as taken from a document published by Philco in 1965 concerning the 'absorption by $CO_2$ between 6600 and 7125 $cm^{-1}$ (1.4-μm region)' and shows the similarity of wavelength dependence.

Figure 15:
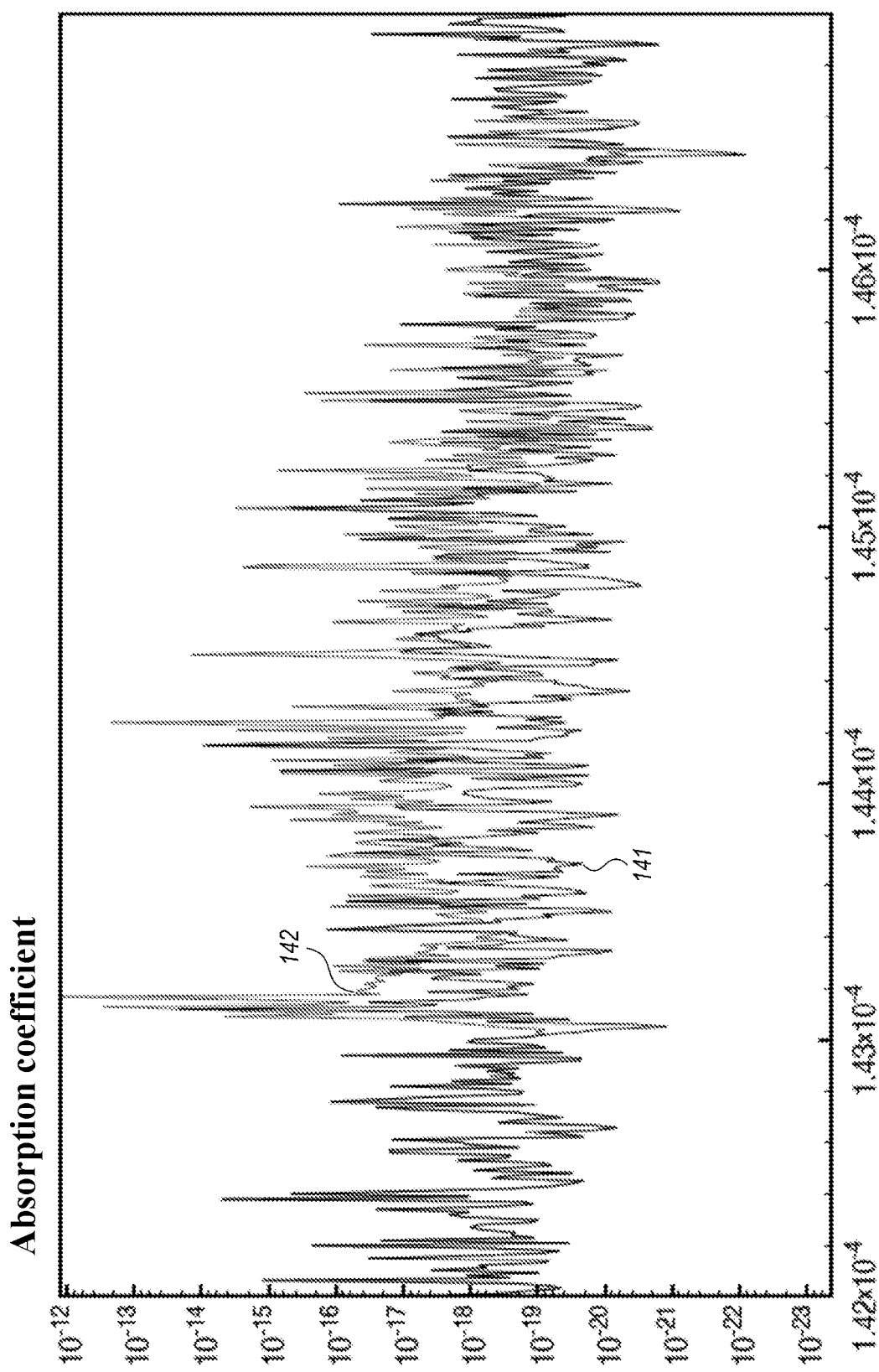
FIG. 15 is a window averaged absorption spectrum of carbon dioxide over water vapor in atmospheric P, T and concentrations identifying carbon dioxide band at 1.4 µm over the water vapor band at 1.38 µm according to an embodiment of the invention.

Reference is now made to FIG. 15, presenting the window averaged absorption coefficient for the 1.4 μm band of CO2 140 where absorption coefficient values of water vapor only 141 and of water vapour and of carbon dioxide combined 142 show the distinction of the $CO_2$ band at 1.4 μm over the 1.38 μm band of water. The concentrations are atmospheric with relative humidity of 15% and carbon dioxide concentration of 400 ppm.

Figure 16B:
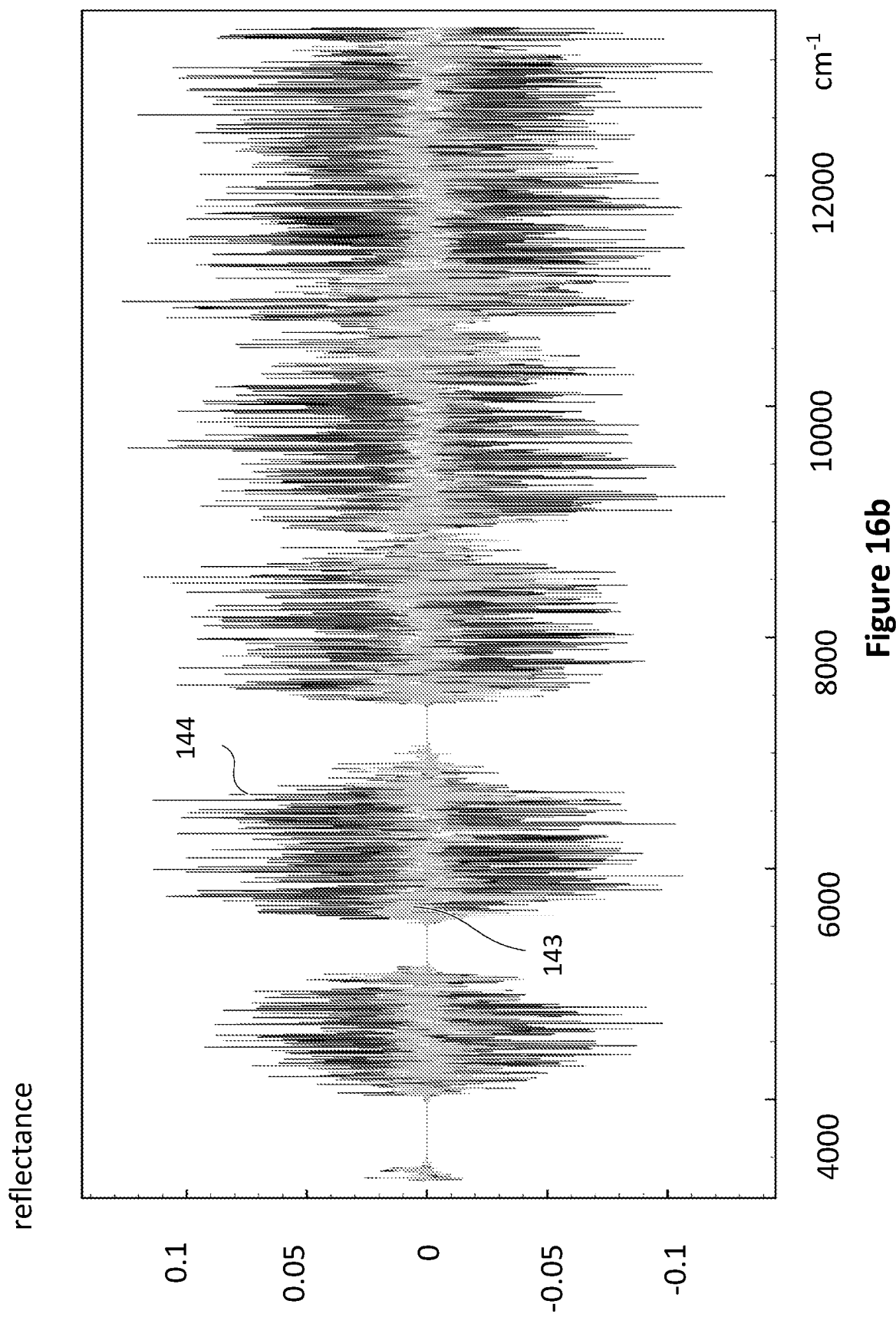

Reference is now made to FIG. 16, presenting the method of data folding for detecting weak signals. In FIG. 16a, a measured spectrum of reflectance vs wavelength in $cm^{-1}$ as obtained from *IASI METOP satellite, CNES,* 2018 designated as Wnum(I) for wavelength and Rad for the absorption was used. Random noise was added to the spectrum for each repeat, denoted as err(I), and averaging on all spectra, each time adding different numbers of spectra. In FIG. 16b the results of the calculation are shown, where the dark lines 143 present simple averaging on small number (Order of 1) of spectra with random noise and the lighter lines 144 present simple averaging on large number (Order of 2) of spectra with random noise added.

Figure 17A:
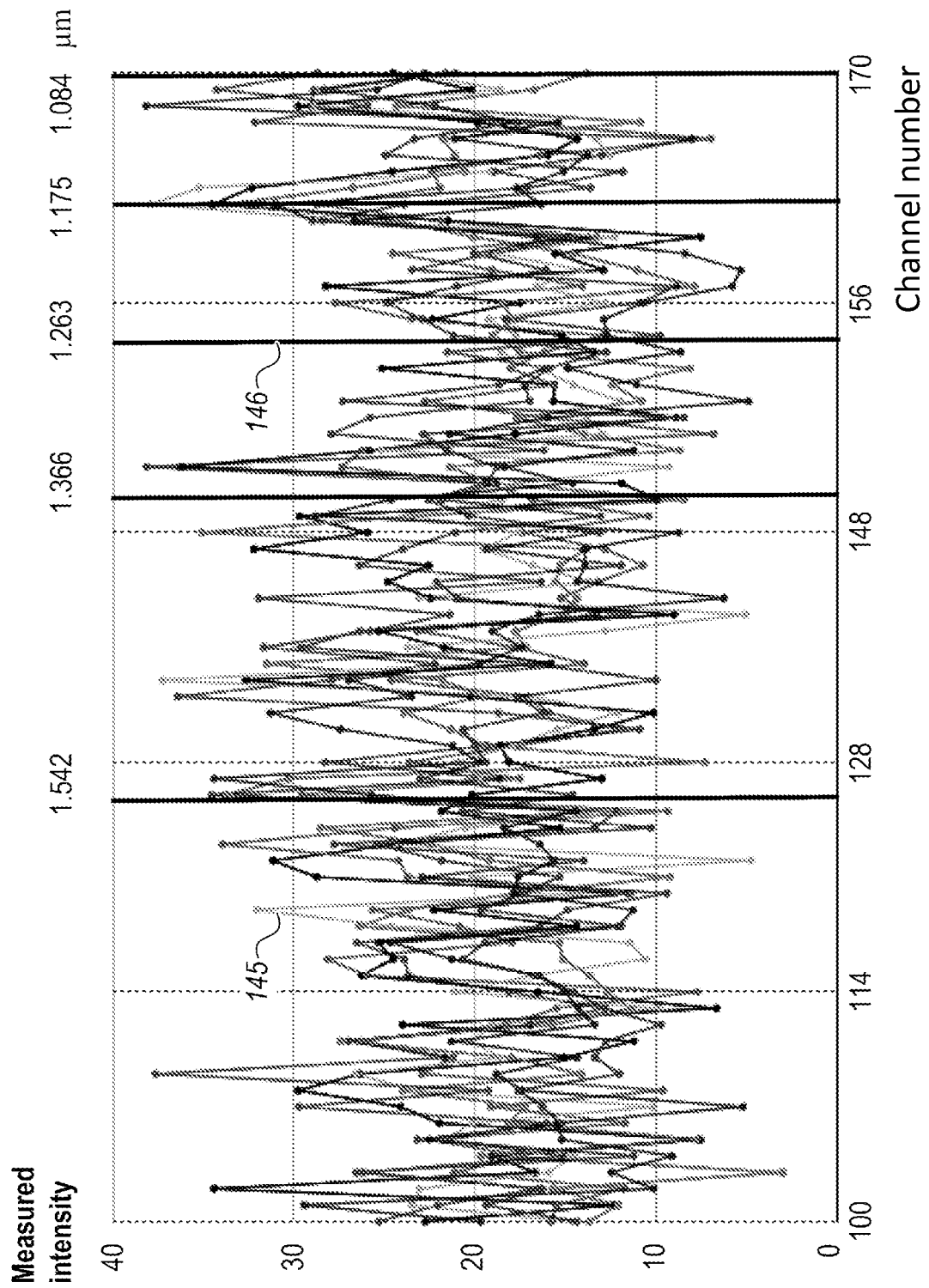
FIGS. 17a-b presents measured intensity vs channel number for many spectral measurements and for data folded average, with Xe-lamp reference lines according to an embodiment of the invention.
Figure 17B:
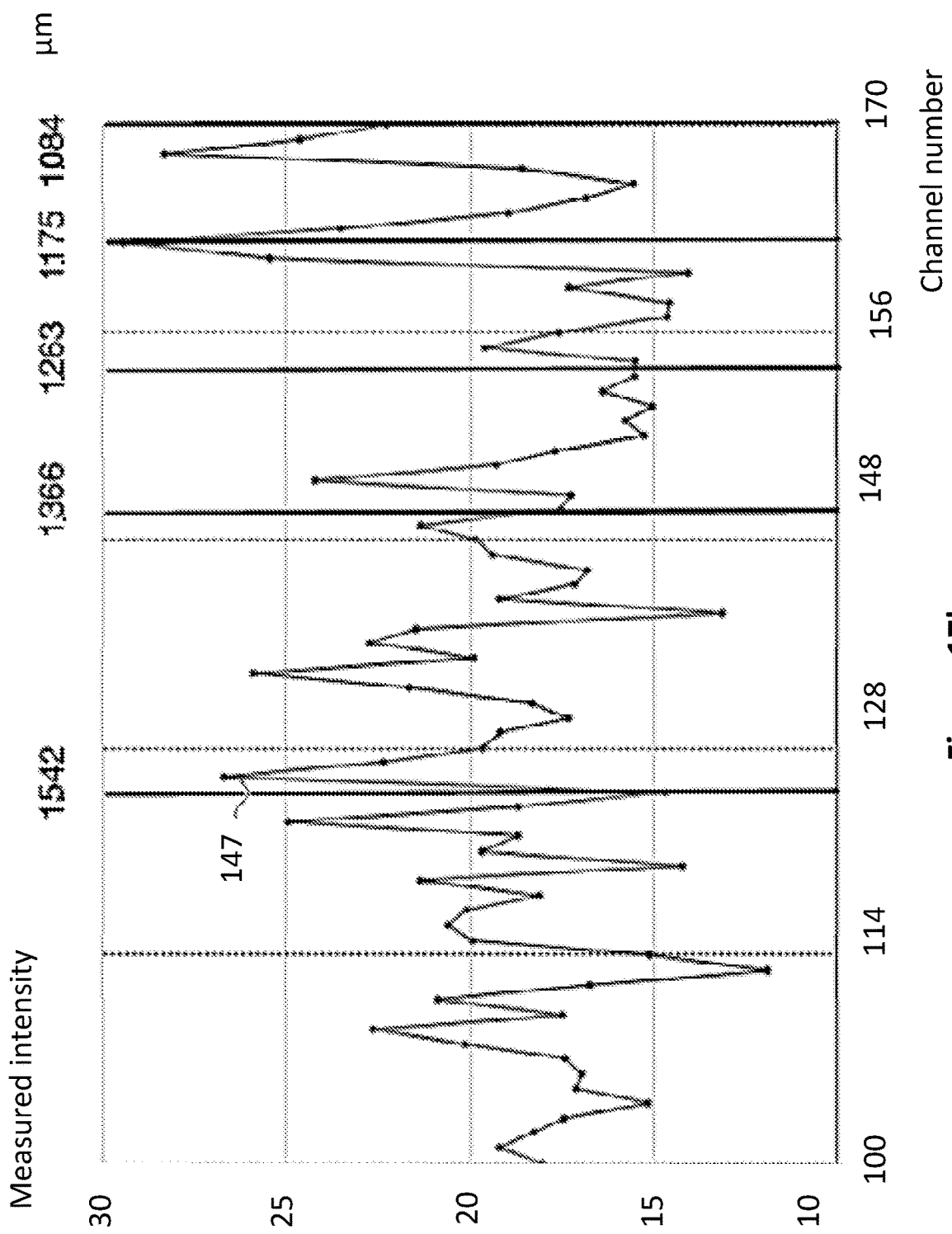

Reference is now made to FIGS. 17a-b, presenting repeated measurements 145 of the same atmospheric volume: 7 measurements within less than two minutes from two separate spectral detectors 101 separated by beam splitter 104, to a total of 14 measurements. The spectrometer as described in Erez N Ribak, 2018, Stationary Fourier Transform Spectrometer, presented in the meeting of the American Optical Society, September 2018, USA. FIG. 17a, presenting all measured spectra on the same figure, featuring measured intensity vs channel number. The numbers of the top of the FIG. 146 are Xe light reference spectral lines for wavelength values of channels. FIG. 17b, presenting the result of data folding 147 which yields a higher SNR, as compared with single consecutive spectra. Within the figure, spectral features at the water vapor 1.0, 1.1, 1.38 μm, and carbon dioxide absorption at 1.44 and 1.6 μm can be seen and where carbon dioxide and water vapor absorption are expected. The results are indicative that the acquiring of more measurements will improve even further the SNR.

Figure 18:
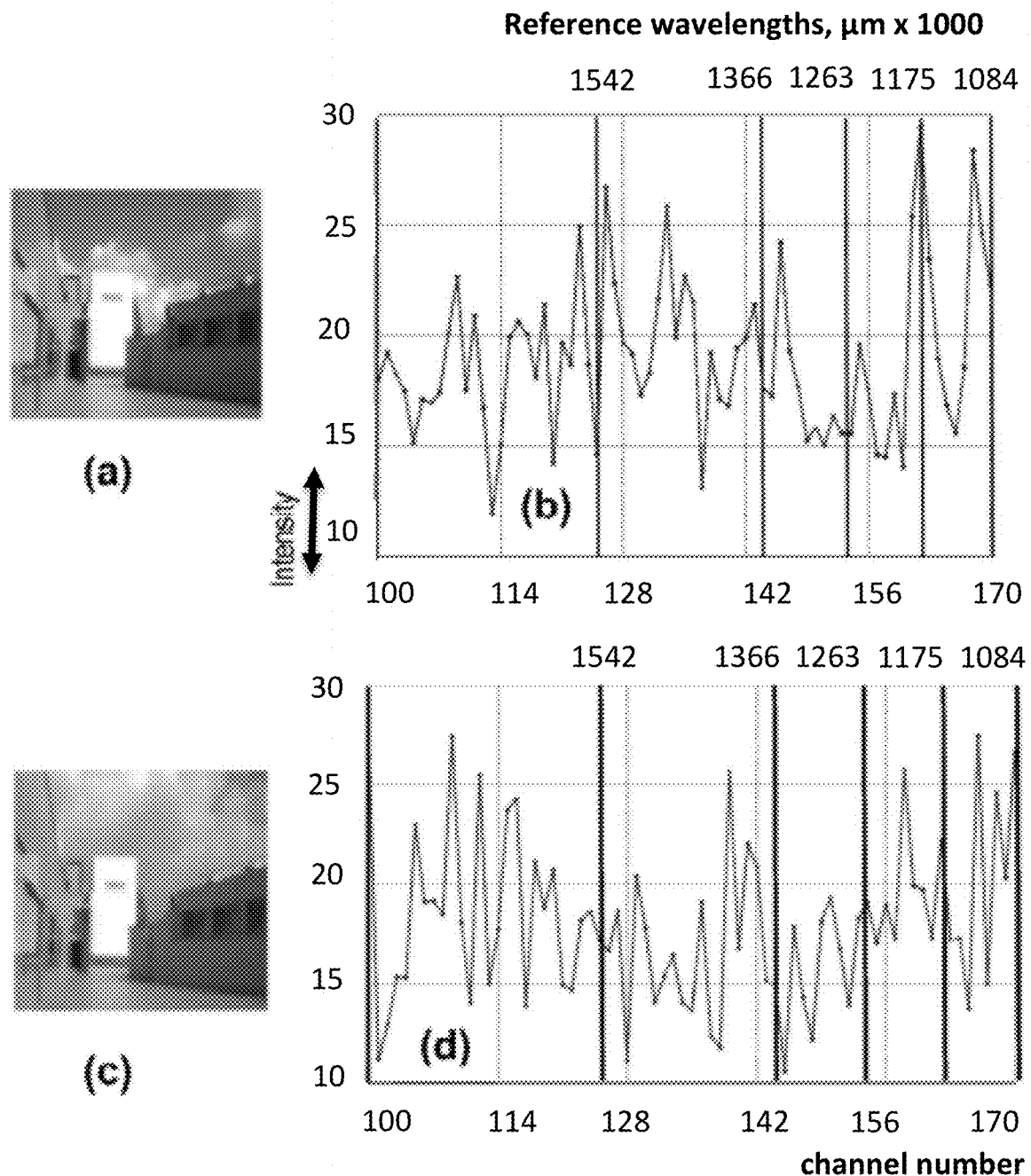
FIG. 18 is an average spectral and imaging simultaneous bore-sighted measurement of clear skies and of clouds according to an embodiment of the invention.

Reference is now made to FIG. 18, presenting a spectral and imaging simultaneous bore-sighted measurement of the semi-transparent transient source, a cloud, from a camera 102 as presented in FIG. 18c, and from a spectrometer 101 as described in FIG. 17a, and presented in FIG. 18d. In FIGS. 18a and 18b are presented similar measurement for reference clear skies. Both are presented on the same vertical scale of intensity vs horizontal channel scale; wavelengths are designated by reference wavelengths of Xenon lamp in μm×1000. Comparing both spectra shows the difference between a cloudy environment and a clear-skies environment. The features at 1.4-1.6 μm characteristic of carbon dioxide disappear in the cloudy skies' measurements 18d, whereas the water lines are of about the same magnitude in both, compare FIGS. 18b and 18d. This enables to differentiate between cloudy environments and non-cloudy environments, such that important spectral features are unveiled, and lines of specific chemical species are identified.

EXAMPLE I

Reference is now made to FIG. 1, which schematically depicts as a non-limiting example a first remote sensing system of the present invention. The system is provided useful for accurate one or more (i) temporal; (ii) spatial; and (iii) spectral mapping(s) of spectrally structured rapidly changing radiation sources. This system is enabled by simultaneous and overlapping measurement(s) from a remote sensing array of detectors, positioned on a fixed or on a moving platform.

The present invention is further provided useful for both (i) accurate characterization of radiation source by spectral, spatial and temporal mapping; and (ii) simultaneous accurate measurement of the same field of view and possibly for magnification from a remote sensing array of instruments, on a fixed or on a moving platform.

This system comprises at least one first member of a group containing spectrometers in one or more given spectral ranges. The system further comprises at least one second member of a group containing imagers and detectors as defined above, provided useful for being sensitive to a same and/or to complementary spectral domains, as aforesaid first member. These at least one first and the at least one second members defined above are positioned on a single optic path.

The members as defined above are separated by e.g., a beam-splitter, thereby enabling the system to measure (i) simultaneously; (ii) at same FOV; and (iii) possible similar magnification. The aforesaid members are operated simultaneously, to provide one or more trains of images, each of which consists of at least one first image, provided by said at least one first member, and at least one second image, provided by said at least one second member.

EXAMPLE II

Reference is now made to FIG. 2, which schematically depicts as a non-limiting example a second remote sensing system of the present invention. This second system is provided useful for accurate one or more (i) temporal; (ii) spatial; and (iii) spectral mapping(s) of spectrally structured rapidly changing radiation sources. This system is enabled by alternate or by simultaneous control to produce overlapping measurement(s) from a remote sensing array of detectors, positioned on a fixed or on a movable platform.

This system is further provided useful for both (i) accurate characterization of radiation source by spectral, spatial and temporal mapping; and (ii) simultaneous accurate measurement of the same field of view in a timescale shorter than the source timescale, and possibly for magnification from a remote sensing array of instruments, on a fixed or on a movable platform.

This system comprises at least one first member of a group containing spectrometers in one or more given spectral ranges. The system further comprises at least one second member of a group containing imagers and detectors as defined above, provided useful for being sensitive to a same and/or to complementary spectral domains, as aforesaid first member. These at least one first and the at least one second members defined above are positioned on a bore-sighted mutual optic path.

The members as defined above are co-aligned on a bore-sighted mutual optic path thereby enabling the system to measure (i) simultaneously; (ii) at same FOV; and (iii) possible similar magnification. The aforesaid members are operated alternately or simultaneously, within a short period of time shorter than the source timescale such that $\tau_{spectro} < \tau_{source}$. This system provides one or more trains of images, each of which consists of at least one first image, provided by said at least one first member, and at least one second image, provided by said at least one second member.

EXAMPLE III

Reference is now made to FIG. 3, which schematically depicts as a non-limiting example a third remote sensing system of the present invention. This third system is provided useful for accurate one or more (i) temporal; (ii) spatial; and (iii) spectral mapping(s) of spectrally structured rapidly changing radiation sources. This system is enabled by overlapping measurement(s) from a remote sensing array of detectors, positioned on a fixed or on a movable platform selected inter-alia from hand-held platform, ground vehicle, marine platform, airborne and space vehicle.

This system is further provided useful for both (i) accurate characterization of radiation source by spectral, spatial and temporal mapping; and (ii) simultaneous accurate measurement of the same field of view and possibly for magnification from a remote sensing array of instruments, on a fixed or on a movable platform.

This system comprises at least one first member of a group containing spectrometers in one or more given spectral ranges. The system further comprises at least one second member of a group containing imagers and detectors as defined above, provided useful for being sensitive to a same and/or to complementary spectral domains, as aforesaid first member. These at least one first and the at least one second members defined above are positioned on a bore-sighted mutual optic path.

The members as defined above are co-aligned on a bore-sighted mutual optic path thereby enabling the system to measure (i) simultaneously; (ii) at same FOV; and (iii) possible similar magnification. The aforesaid members are operated alternately or simultaneously, within a short period of time shorter than the source timescale such that $\tau_{spectro} < \tau_{source}$. This system provides one or more trains of images, each of which consists of at least one first image, provided by said at least one first member, and at least one second image, provided by aforesaid at least one second member.

EXAMPLE IV

Reference is now made to FIG. 4, which schematically depicts as an example a fourth remote sensing system of the present invention. This fourth system is provided useful for accurate one or more (i) temporal; (ii) spatial and (iii) spectral mapping(s) of spectrally structured rapidly changing radiation sources. This system is enabled by simultaneous and overlapping measurement(s) from a remote sensing array of detectors, positioned on two or more platforms, the platforms selected inter alia from hand-held platform, wearables, ground vehicle, marine platform, airborne and space vehicle.

This system comprising at least one first platform and at least one second platform, enabled to operate concertedly, alternately or simultaneously, within a short period of time shorter than the source timescale such that $\tau_{spectro} < \tau_{source}$.

This system is further provided useful for both (i) accurate characterization of radiation source by spectral, spatial and temporal mapping; and (ii) simultaneous accurate measurement of the same field of view and possibly for magnification from a remote sensing array of detectors on a platform.

Each of the platforms comprising detector(s) being at least one first member of a group containing spectrometers in one or more given spectral ranges; and/or at least one second member of a group containing imagers and detectors as defined above, provided useful for being sensitive to a same and/or to complementary spectral domains, as aforesaid first member. These at least one first and the at least one second members defined above are positioned on a bore-sighted mutual optic path in one platform, and point at an exactly overlapping FOV from at least two or more platforms.

The members as defined above are configured for accurate pointing thereby enabling the system to measure (i) simultaneously; (ii) at overlapping FOV; and (iii) possible similar magnification. This system provides one or more trains of images, each of which consists of at least one first image, provided by said at least one first member, and at least one second image, provided by said at least one second member. It is in the scope of the invention wherein alternatively or additionally, at least a portion of aforesaid members are spatially configured to converge towards at least one focal point, field of view or atmospheric volume.

EXAMPLE V

Reference is now made to FIG. 5, which schematically depicts as an example a fifth remote sensing system of the present invention. This fifth system is provided useful for accurate one or more (i) temporal; (ii) spatial; and (iii) spectral mapping(s) of spectrally structured rapidly changing radiation sources. This system is enabled by simultaneous and overlapping measurement(s) from a remote sensing array of detectors, positioned three or more platforms, the platforms selected inter alia from hand-held platform, ground vehicle, marine platform, airborne and space vehicle.

This system comprises at least one first platform, at least one second platform, and at least one third platform, enabled to operate concertedly, alternately or simultaneously, within a short period of time shorter than the source timescale such that $\tau_{spectro} < \tau_{source}$. This system is further provided useful for both (i) accurate characterization of radiation source by spectral, spatial and temporal mapping; and (ii) simultaneous accurate measurement of the same field of view and possibly for magnification from a remote sensing array of detectors on a platform.

At least a portion of the platforms comprising detector(s) being at least one first member of a group containing spectrometers in one or more given spectral ranges; and/or at least one second member of a group containing imagers and detectors as defined above, provided useful for being sensitive to a same and/or to complementary spectral domains, as aforesaid first member. These at least one first and the at least one second members defined above are positioned on a bore-sighted mutual optic path, and point at an exactly overlapping FOV from at least two or more platforms.

The members as defined above are configured for accurate pointing thereby enabling the system to measure (i) simultaneously; (ii) at overlapping FOV; and (iii) possible similar magnification, thereby providing at least 2D location determination of said radiation source. This system provides one or more trains of images, each of which consists of at least one first image, provided by said at least one first member, and at least one second image, provided by said at least one second member. It is in the scope of the invention wherein alternatively or additionally, at least a portion of aforesaid members are spatially configured to converge towards at least one focal point, field of view or atmospheric volume.

EXAMPLE VI

Reference is now made to FIG. 6, which schematically depicts as an example a sixth remote sensing system of the present invention. This sixth system is provided useful for accurate one or more (i) temporal; (ii) spatial; and (iii) spectral mapping(s) of spectrally structured rapidly changing radiation sources. This system is enabled by simultaneous and overlapping measurement(s) from a remote sensing array of detectors, positioned on four or more platforms, the platforms selected inter alia from hand-held platform, ground vehicle, marine platform, airborne and space vehicle.

This system comprises at least one first platform, at least one second platform, at least one third platform, and at least one fourth platform, enabled to operate concertedly, alternately or simultaneously, within a short period of time shorter than the source timescale such that $\tau_{spectro} < \tau_{source}$. This system is further provided useful for both (i) accurate characterization of radiation source by spectral, spatial and temporal mapping; and (ii) simultaneous accurate measurement of the same field of view and possibly for magnification from a remote sensing array of detectors on a platform.

At least a portion of the platforms comprising detector(s) being at least one first member of a group containing in one or more given spectral ranges; and/or at least one second member of a group containing imagers and detectors as defined above, provided useful for being sensitive to a same and/or to complementary spectral domains, as aforesaid first member. These at least one first and the at least one second members defined above are positioned on a bore-sighted mutual optic path, and point at an exactly overlapping FOV from at least two or more platforms.

The members as defined above are configured for accurate pointing thereby enabling the system to measure (i) simultaneously; (ii) at overlapping FOV; and (iii) possible similar magnification, thereby providing at least 3D location determination of said radiation source. This system provides one or more trains of images, each of which consists of at least one first image, provided by said at least one first member, and at least one second image, provided by said at least one second member. It is in the scope of the invention wherein alternatively or additionally, at least a portion of aforesaid members are spatially configured to converge towards at least one focal point, field of view or atmospheric volume.

EXAMPLE VII

Reference is now made to FIG. 11, which schematically depicts as an example a seventh remote sensing system of the present invention. According to another embodiment of the invention, means and methods are disclosed to enable measurement of semi-transparent transient sources by means as described in EXAMPLES I-VI, and methods pertaining to accurate temporal, spatial and spectral mapping of rapidly changing radiation sources with distinct spectral structure, in at least one spectral domain by exact spatial and temporal overlap of spectral and other imaging methods from remote sensing on either fixed or on moving platforms, operating as a cluster, to compensate for weight/volume limitations. Data are collected for knowledge of different viewing angles between platforms, and their stability.

The pointing knowledge is crucial and allows for overlapping the spectral and the imaging data. This enables repeating each measurement as many times as there are platforms, thus acquiring more data in every measurement round. An addition of several measurements in a total time scale of $\tau_{spectro}$ shorter than $\tau_{source}$, allows for higher SNR.

EXAMPLE VIII

Reference is now made to FIG. 7 which schematically depicts as an example an eighth remote sensing system of the present invention. According to another embodiment of the invention, means and methods are disclosed to enable measurement of semi-transparent transient sources by means as described in EXAMPLES I-VII, and methods pertaining to accurate temporal, spatial and spectral mapping of rapidly changing radiation sources with distinct spectral structure, in at least one spectral domain by exact spatial and temporal overlap of spectral and other imaging methods from remote sensing on either fixed or on moving platforms, in the case of failure of said spectrometer. A backup spectrometer is positioned off the optic axis, comprising a backup motor, intended to push the spectrometer out of the optic axis and the backup spectrometer into it by a single action. This ensures the continuation of the platform's operation at a similar or different wavelength domain upon failure of the main spectrometer.

EXAMPLE IX

Reference is now made to FIG. 9, which schematically depicts as an example a ninth remote sensing system of the present invention. According to another embodiment of the invention, means and methods are disclosed to enable measurement of semi-transparent transient sources by means as described in EXAMPLES I-VIII, and a method pertaining to accurate temporal, spatial and spectral mapping of rapidly changing radiation sources with distinct spectral structure, in at least one spectral domain by exact spatial and temporal overlap of spectral and other imaging methods from remote sensing on either fixed or on moving platforms. Characterization of the motion of the rapidly moving radiation source is done by, inter alia, at least one member of a group consisting the followings: (i) Combination of spectroscopy and visible imaging—when the spectral emission has a defined visible spectral range, such as for NOX; (ii) Combination of spectroscopic and IR or SAR imaging—when there is no visible component to the emission, such as in wind currents. Characterization of rapidly changing radiation sources from an exact SAR train of images, simultaneous with, and on same FOV of the spectrometer, reveals details of the motion of the cloud or semi-transparent transient sources; and (iii) Doppler shift of spectral lines—in the same or different spectral domains, to determine the expansion velocity, on the axis of observation, by studying the line shape, chosen from inter-alia: single non-shifted spectral line; sum of blue-shifted and redshifted lines as much as there is motion in both directions, at low resolution; resolved absorption spectra of separate blue shifted and/or red shifted lines if there are any; any combination of absorption and emission lines of the same spectral feature; any combination of absorption and emission lines interconnected with flow of material within semi-transparent transient source.

EXAMPLE X

Reference is now made to FIG. 10a, which schematically depicts as an example a tenth remote sensing system of the present invention. According to another embodiment of the invention, means and methods are disclosed to enable accurate characterization of clouds in transit, at similar or different spectral domains by simultaneous and overlapping spectroscopy (absorption and emission) and/or simultaneous and overlapping spectroscopy and imaging; The aforesaid means and method are also useful for measuring other semi-transparent transient sources Various means described in EXAMPLES I-IX, and methods pertaining to measurement from both stationary (fixed) or movable platform(s), of semi-transparent transient sources illuminated from the background by a source of blackbody radiation in the visible and/or other spectral domains, inter alia, the twilight skies; the sun, with a protecting cutoff filter, e.g., passes wavelength longer than 1.2 micrometer; the moon; a ground light-source, etc., which passes through parts of the cloud or semi-transparent transient sources, where its optical depth is about 1. The aforesaid cloud or semi-transparent transient sources modulates the spectrum of the blackbody source, and reveals its internal structure.

EXAMPLE XI

Reference is now made to FIG. 10b which schematically depicts a reference measurement as conducted for EXAMPLE X. The spectrum measured for e.g., clear skies, serves as a reference which should be subtracted from the semi-transparent transient source's spectra, in order to obtain a clean spectrum of the source itself, allowing to calculate a radiative transfer model for the source. This example assumes that there is only one platform involved with measuring the source, thus, the source and reference field-of-views should be measured alternately. The second frame can also be complementary to the first one to yield a wider field-of-view.

EXAMPLE XII

Reference is made now to FIG. 12 which schematically depicts a reference measurement as conducted for EXAMPLE X. The spectrum measured for e.g., clear skies, serves as a reference which should be subtracted from the semi-transparent transient source's spectra, in order to obtain a clean spectrum of the source itself, allowing to calculate a radiative transfer model for the source. This example assumes that there are at least two platforms which may be aimed at similar or different fields of view, either as for measuring a reference or as for measuring a complementary field of view. In both cases the reconstruction requires a software which accounts for the difference in viewing angle of the second field of view. If only one platform involved with measuring the source, the source and reference field-of-views should be measured alternately. In this configuration, less measurements of the source are taken at the same time but the reference is measured simultaneously and at the same location during the motion of the platforms.

EXAMPLE XIII

Reference is now made to FIG. 10a which schematically depicts as an example a method to study very weakly absorbing species (in concentration or in absorption coefficient), by tilting said platform so as to measure at different angles to nadir into the atmosphere in a grazing angle towards the limb. The enhanced thickness of the atmosphere when measuring at an angle, allows to discover species which are generally too weak to detect by regular remote sensing. The different angles serve as reference to each other, and subtracting them in a row allows to track down the species' profile throughout the atmosphere. Thus, a plurality of tilt angles yields a profiling of species in the planetary atmosphere, and allows to measure also a reference field of view without the semi-transparent transient source in a large angle off nadir or pointing towards another direction.

EXAMPLE XIV

Reference is now made to FIG. 16 which schematically depicts as a non-limiting example a method to extract data from measurements made by said spectrometer. Spectrometers as described in EXAMPLES I-IX, on the optic path of, specifically, a small-aperture telescope, may yield low signal-to-noise ratios. Since the spectral line parameters of most detected chemical species are well-known, the signal-to-noise ratio can be much improved by way of 'data folding', as described in Shaviv G. et al, (1972) *Statistical Analysis of Multiple Absorption Spectra in QSO*, Astrophysics and Space Science, 19(1), pp. 159-163 incorporated herein as a reference. The described mode of analysis, allows to improve the signal-to-noise ratio of the spectrum obtained, by collecting a large number of spectra of the rapidly changing radiation source during a short period of time relative to the time of change, and averaging them to improve the signal to noise ratio. If the timescale of one measurement is e.g., 100 msec, then in 1 second, ten measurements of the same object can be obtained, which can be folded to reduce the noise by $(1/\sqrt{10})$. The accuracy of the measurement is thus a function of the timescale of change of the radiation source, and of the stabilization of pointing to the same FOV during the time of measurement.

FIG. 16a-b presents the logic of our data folding method for detecting weak signals. In FIG. 16a, a measured spectrum of reflectance vs wavelength in $cm^{-1}$ as obtained from *IASI METOP satellite, CNES,* 2018 incorporated herein as a reference, and designated as Wnum(I) for wavelength and Rad for the absorption was utilized. The current invention by this embodiment, adds random noise to the spectrum for each repeat, denoted as err(I), and averaging on all spectra, each time adding different numbers of spectra. In FIG. 16b the results of the calculation are shown, presenting simple averaging on small number (Order of 1) of spectra with random noise (dark lines) and presenting simple averaging on large number (Order of 2) of spectra with random noise added (light lines). A distinct difference is observed for the different number of lines averaged, showing the method applicable for extracting weak lines out of the noisy background.

EXAMPLE XV

According to one embodiment of the present invention, a method for the identification of optimal wavelengths for observation is provided by steps as follows: obtaining from remote sensing an atmospheric profile for a given planet: composition in total column density, and temperature and pressure as a function of the height, z; obtaining an absorption spectrum for said planetary atmosphere; choosing a chemical species to be detected; calculating the absorption spectra for the composition for all given lines; identify largest signal-to-noise ratio for characteristic chemical species with line-width of 2-6 Å; and creating a list of these wavelengths $\{\lambda_1, \ldots, \lambda_n\}$ and their related optical depth.

EXAMPLES XVI

According to another embodiment of the present invention method for calculating curve of growth for aforesaid temperature vertical profile at specified wavelengths is provided for atmospheres of well-mixed composition, by steps as follows: inputting of vertical temperature profile; calculating $A_0$ (the line central depth) and $\Delta v_D$, (the Doppler broadening) from measured absorption spectra for said temperature profile and composition for all given lines; using the linear approximation equation for the effective line-width (W) of non-saturated spectral lines as a function of $n_0$, the number of species' molecules in the line of sight or the column density, see e.g., Dimitri Mihalas, *Stellar Atmospheres*, 1970, pp: 335, W.H. Freeman and Co., San Francisco incorporated herein as a reference, to calculate the linear coefficient of $\eta_0$ for each wavelength in the list:

$$W_\lambda = 2A_{(0,\lambda)} \Delta v_{D,\lambda} \sqrt{\pi/2} \eta_{(0,\lambda)};$$

a new list of $\{\lambda_1, \ldots, \lambda_n\}$ and their related linear coefficient, $S_\lambda$ is calculated.

Then, $S_\lambda$ will be used for determining $\eta_{(0, \lambda)}$ for any given value of $W_\lambda$ by calculating effective width of lines using the above equation by analyzing spectral data. The number of equations for the solution are chosen according to the number of parameters in the problem, thus enabling a linear solution, that is, by the inversion of a matrix. This method is unique in that the number of parameters is equal to the number of equations, and there is no need to fit any parameters.

The following step is now executed: drawing curve of growth to relate line width $W_\lambda$ to $\eta_{0, \lambda}$ the concentration within line of sight

EXAMPLES XVII

The method of the present invention consists, inter alia, of reading line after line from the molecular data of each species and calculating its contribution to the absorption at wavelengths $\lambda 1$ to $\lambda 2$ where the range $\lambda 1$-$\lambda 2$ is a free parameter. So, each data line contributes absorption over a given wavelength range. The computer then goes over all lines in the range of wavelength needed for the particular calculation. In the most demanding case, that of calculating the temperature of the gas, about 2 million computer-lines are needed. Thus, in the case of water vapor for example, the program passes over the 114 million lines and calculates the contribution to the 2 million calculation points.

The current invention now discloses a method for data reduction from spectral databases such as HITRAN, whose advantage is that it can be done without losing information. That is crucial for radiative transfer (RT) calculations, because it accounts for the line-by-line absorption of all spectral lines of all species involved. A wavelength window is used, spanning a symmetric, but can be also non-symmetric, wavelength range about a chosen wavelength. The chosen wavelengths, or calculation points, are the wavelengths for which the RT analysis will be finally carried out, and their periodicity is chosen as a function of the total wavelength range for which the RT is done (thousand to million Angstroms for the Earth); of the required resolution of the calculation vis-a-vis the wavelength range of the window; of the density of the spectral lines with that wavelength range, etc. The window wavelength range is chosen so as to include the contribution of adjacent lines to the calculation wavelengths, such that widening the window additionally, does not change significantly the absorption at the chosen calculation points The above sweep is carried out over all molecules in the atmosphere and the only stored data are the absorptions at the calculation points. One can assume that the contribution of the different molecules is additive.

Since this hereto disclosed technology has to iterate for the gas temperature this process must be repeated after each iteration for the temperature. The method of calculation is easily parallelized.

The advantage of this embodiment of the invention is that the HITRAN catalogue is never stored in the program which calculates the radiation field. The calculation points contain the total contribution of all molecules. Since the temperature is iterated for, this process is repeated after each iteration and in this way the absorption coefficients agree with the gas temperature, pressure and temperature broadening and of course composition. The continuum generated by the lines is properly evaluated.

The radiative transfer program does not include the complication of the derivation of the absorption coefficients. The current embodiment of the invention applies the Van Wleck-Weiskopf method to calculate the contribution of the tails of the many lines to obtain the effective continuum. However, should the need arise; it is trivial to replace the algorithm for the contribution of the line's wings.

EXAMPLE XVIII

In one example of the current invention, a wavelength dependency of the absorption coefficients of $CO_2$ is required at 288K, 1 atmosphere and 395 ppm at a wavelength range of 7000-50,000 Angstroms. Line data taken from HITEMP2010 for $CO_2$ lines is treated by the described method. User-defined distinct wavelengths are defined every 0.5 Angstroms and data from the HITEMP2010 list is read, where the contribution of each entry in the HITRAN database is applied to within a window of 50 Angstroms on each side of the user-defined distinct wavelength; above 44,900 Angstroms, the user-defined wavelength difference is enlarged to 1 Angstrom and the window to 100 Angstroms on each side.

To define the contribution of the HITRAN data to the user-defined wavelengths, the data is used to calculate the absorption coefficients for the given $CO_2$ concentration, temperature and pressure and the disclosed technology applies the Van Wleck-Weiskopf method to calculate the contribution of the tails of the many lines to obtain the effective continuum at each chosen wavelength. The result is a new wavelength dependency of the absorption coefficients of $CO_2$, which may be stored in the computer for further use, for radiative transfer calculations or any other use.

EXAMPLE XIX

Reference is now made to FIG. 13, disclosing a method of the window extraction of spectral data from databases such as HITRAN2012 for accurate energy conserving radiative transfer calculations. Two wavelength axes are important for this calculation: the wavelength list of HITRAN or any other database, and the wavelength list of the calculation wavelength points. The spectral data, depends on referenced measurements that create the database; See Rothman, L. S, 2013 *Journal of Quantitative Spectroscopy and Radiative Transfer*, Vol. 130, p. 4-50 incorporated herein as a reference. The calculation wavelength points are chosen equally every defined wavelength difference, and serve as 'wells' into which the spectral data is 'poured'. The database parameters are used to calculate the spectral line structure for the given P, T, C parameters of the calculation. The line profiles are calculated and their wing contribution at the relevant calculation wavelength points is determined. The contribution distance of the lines is determined before the calculation by the width of the window, and thus the 'wells' add up the contributions from all adjacent lines, such that they can be included in the calculation of the specific calculation points. The lines are read in order of their appearance in the database list. The total absorption which is added up from all contributions to each wavelength point is taken into consideration for the radiative transfer calculation and thus, reduces tremendously the amount of data treated in every calculation. Since the P, T, C condition is iterated for in each calculation of the radiative transfer, this process is repeated in every round, as the line profiles changes.

EXAMPLE XX

Reference is now made to FIG. 14*a*, presenting the calculation results for the 1.4 μm band of CO2, comparing the raw data as extracted from the HITRAN2012 database and after the window calculation (288K, 1 atm). The general trend of the band shape is conserved, and the wing contributions of adjacent spectral lines form a continuum in the background. This shows the applicability and reproducibility of the real spectrum with the window method. FIG. 14*b* presents a transmission spectrum of the same band measured at 296K and 1 atm as taken from a document published by Philco in 1965 concerning the '*Absorption by CO2 between 6600 and 7125 $cm^{-1}$ (1.4-micron region)*' incorporated herein as a reference and shows the similarity of wavelength dependence.

Reference is now made to FIG. 15, presenting the window averaged absorption coefficient for the 1.4 μm band of CO2 where absorption coefficient values of water vapor only (bottom) and of water vapor and of carbon dioxide combined (top) show the distinction of the CO2 band at 1.4 μm over the 1.38 μm band of water. The concentrations are atmospheric with relative humidity of 15% and carbon dioxide concentration of 400 ppm.

EXAMPLE XXI

Studying cloud chemistry As stated before, clouds are a major uncertainty factor in the study of climate. Clouds are volumes of condensed water droplets in equilibrium with water vapor and ice crystals. These volumes, which are observable to the naked eye by scattering of visible light from their volume structures, are islands of unique chemical processes within the bulk of the atmosphere. Clouds are known to form by interaction of water vapor with aerosol particles composed of sulfur-based molecules of marine origin, and of carbon-based molecules over land, see Yinon Rudich (2003) *Chem. Rev.* 103 5097-5124, incorporated herein as a reference. Clouds are also involved in chemical interaction with their environment, the kinetics of which are influenced by the state of the atmosphere around them. During this process, clouds must exchange with their environment different chemical species, including water vapor, aerosol particles and other solvated molecules. The change of concentration of these chemical species with time, is the focus of this embodiment.

The chemical environment of clouds, as well as the cloud's inside structure, where the optical path of the cloud is order of 1, can be studied by a spectrometer, to learn about chemical processes which are involved with cloud formation and evolution. The spectral features expected from such a diffuse environment, are relatively weak, and require special treatment, in order to extract from them the relevant information. This ability depends for one on the resolution of the spectrometer, but also on the theoretical basis available to extract the knowledge out of the measured spectrum. High resolution spectral measurements, allow to treat the spectral features in detail. But to study about the concentration change of the chemical species involved, and about their motion within the cloud and outside its volume, data folding, as defined in this invention, is essential to extract valuable information. The basis for data folding is the understanding that the spectral features repeat themselves throughout the measurements, and thus averaging consecutive measurements should reduce considerably the signal to noise ratio and enhance the observed features. Additionally, the measurement of a reference of the environment is crucial for this method, because the chemical structure of the optical path to the semi-transparent transient source must be subtracted.

EXAMPLE XXII

Reference is now made to FIGS. 17-18, which schematically depicts as an example a measurement of clouds and of clear skies from the field, by a spectrometer as described in Erez N Ribak, 2018, Stationary Fourier Transform Spectrometer, presented in the meeting of the American Optical Society, September 2018, USA, incorporated herein as a reference. Another example for a spectrometer capable of doing this is that of the Infrared Atmospheric Sounding Interferometer (IASI) instrument of the European MetOp satellite. The method of data folding, as defined in this invention, is provided useful for obtaining a higher SNR, as compared with single consecutive frames.

Reference is made again to FIGS. 17*a-b*, presenting repeated measurements of the same atmospheric volume: 7 measurements within less than two minutes from two separate spectral detectors separated by beam splitter, to a total of 14 measurements. The spectrometer as described in Erez N Ribak, 2018, Stationary Fourier Transform Spectrometer, presented in the meeting of the American Optical Society, September 2018, USA incorporated herein as a reference. FIG. 17*a*, presents all measured spectra on the same figure, featuring measured intensity vs channel number. The number axis on the top of the figure are Xe light reference spectral lines for wavelength values of channels. FIG. 17*b*, presents the result of data folding, as defined in this invention, which yields a higher SNR, as compared with single consecutive spectra. Within the figure, spectral features at the water vapor 1.0, 1.1, 1.38, and carbon dioxide absorption at 1.44 and 1.6 µm can be seen and where carbon dioxide and water vapor absorption are expected. The results are indicative that the acquiring of more measurements will improve even further the SNR.

Reference is made again to FIG. 18, presenting a spectral and imaging simultaneous bore-sighted measurement of the semi-transparent transient source, a cloud, from a camera as presented in FIG. 18c, and from a spectrometer as described in FIG. 17a, and presented in FIG. 18d. In FIGS. 18a and 18b are presented similar measurement for reference clear skies. Both are presented on the same vertical scale of intensity vs horizontal channel scale; wavelengths are designated by reference wavelengths of Xenon lamp in µm×1000. Comparing both spectra shows the difference between a cloudy environment and a clear-skies environment. The features at 1.4 to 1.6 µm characteristic of carbon dioxide disappear in the cloudy skies' measurements 18d, whereas the water lines are of about the same magnitude in both, compare FIGS. 18b and 18d.

This enables to differentiate between cloudy environments and non-cloudy environments, such that important spectral features are unveiled, and lines of specific chemical species-identified.

EXAMPLE XXIII

Reference is now made to FIGS. 10c-d, presenting the platform 109 and/or the bore sighted pair in a planetary orbiting configuration pointed at the planetary surface, such that radiation originating in an external light source is transmitted through the semi-transparent transient source as to allow direct spectroscopy of said source in wavelength range of source in FIG. 10c. In FIG. 10d, on the planetary surface there is an identical bore-sighted pair which allows for measurement of chemical gradients about the semi-transparent transient source, by obtaining information from two opposite directions. The second platform can also be not attached to the surface, such that the observation is done from a different angle in space, as in the combination of FIG. 10b and FIG. 10d.

The invention claimed is:

1. A method for measuring and analyzing an internal structure of a semi-transparent transitory source (STTS) by remote sensing, said method comprising
   i. bore-sighting at least one spectrometer and at least one optic device selected from a group consisting of one or more spectrometers; one or more imagers; and at least one spectrometer and at least one imager, wherein bore-sighting is configured to align and synchronize multiple sensing instruments;
   ii. mounting at least one bore-sighted pair on at least one platform;
   iii. pointing simultaneously all of said at least one platform towards at least one field of view;
   iv. acquiring spectral data in a manner selected from the group consisting of:
      a. simultaneously by said at least one spectrometer and said at least one optic device, from at least one platform of semi-transparent transient source; or
      b. simultaneously or alternately by said at least one spectrometer and by said at least one optic device from at least one platform of semi-transparent transient source; and a reference field of view for semi-transparent transient source; or
      c. simultaneously or alternately by said at least one spectrometer and by said at least one optic device from at least one platform of at least two complementary fields of view of the source; and
      d. any combination thereof
   v. repeating at least one of step (a) to (c), from at least one platform, for a total timescale which is shorter than a source timescale;
   vi. adjusting data measured for different solid angles of different platforms;
   vii. relating spectral data from a first spectrometer with data from said at least one optic device as a reference point for spatial resolution in observed properties of the semi-transparent transient source, by corresponding the overlapping fields of view;
   viii. using a window to extract absorption coefficients from database without losing spectral data information, thereby enabling calculation of exact spectral line profiles from data measured from STTS by said spectrometer; said exact spectral line profiles are tool to study STTS and its environment; and
   ix. evaluating vertical chemical profile within the STTS, by building a curve of growth (COG) from weakly absorbing chemical species characterized by an optical depth of about 1, thereby measuring and analyzing STTS;
   wherein said extracting absorption coefficients comprising
   a. providing absorption coefficients of at least one molecular species from an up-to-date database list of all molecular absorption parameters of said species, as a function of wavelength;
   b. creating a user defined list of distinct equally-spaced or arbitrarily chosen wavelengths to provide for which the absorption coefficients are used for the radiative transfer analysis so that their periodicity is chosen as a function:
      I. of the total wavelength range for which the RT is done, including range of $10^3$ to $10^6$ Å for Earth;
      II. of the required resolution of the calculation vis-a-vis the wavelength range of the window; and
      III. of the density of the spectral lines with that wavelength range;
   c. defining a chosen window wavelength range symmetrically, or non-symmetrically, about the defined wavelengths of the list, chosen so as to include the contribution of adjacent lines to the calculation wavelengths, such that widening the window additionally, does not change significantly the absorption at the chosen calculation points;
   d. reading the molecular absorption parameters of said at least one molecular substance at a first data wavelength in the database list;
   e. if first database wavelength does not fall within the chosen wavelength range of at least one distinct user-defined wavelength, reading the next database wavelength until it overlaps with the chosen wavelength window range of the first user defined distinct wavelength;
   f. calculating from said molecular absorption data a line profile for said database wavelength, given the pressure, temperature, concentration (P,T,C) conditions for the chemical species and atmospheric layer such that the contribution of each line of every species is a function of the species' concentration in the atmosphere, its statistical weight and its calculated profile at high or at low pressure by steps of:

I. preparing the partition function;
II. calculating the Voigt function;
III. choosing, according to the pressure shift, the function for the line shape; at low pressures, pressure shift <200 cm$^{-1}$, use Van-Vleck Weisskopf line shape; at higher pressures, taper the wing effect by reducing the distant effect; and,
IV. calculating the statistical weight of the lower level times the transition probability;

g. extracting the contribution from said line profile to the absorption coefficients at each wavelength in the wavelength window range about the user-defined distinct wavelength, as the line profile extends throughout many wavelengths, their contribution to the different calculation points is collected throughout the window range;

h. repeating steps (d) to (g) for each database wavelength until it exceeds the wavelength window range about the last user-defined distinct wavelength; for each calculation point, the window is moved one calculation unit further, thus the initial window wavelength is adjusted accordingly; and i. obtaining a list of the user defined distinct wavelengths and the respective absorption coefficients which may be stored in the computer for further use for radiative transfer or other calculations or any other use, further comprising a step for enhancing signal to noise ratio (SNR), selected from the group consisting of:

a. tilting said platform towards said source and said reference field of view (FOV); said reference field of view comprises a field of view other than the measured field of view;

b. observing through the source via a longer path, resulting in a larger optical depth of a weakly absorbing chemical species; said method comprising step (s) of tilting said either platform or said bore sighted pair towards an optical path being longer than the vertical line;

c. observing through an STTS within a planetary atmosphere via a longer path than the vertical; comprising step(s) of tilting said either platform or said bore sighted pair towards the limb off the Nadir;

d. observing through an STTS illuminated from the background by an external radiation source in the visible and/or other spectral domain, resulting in direct spectroscopy of a weakly absorbing species; said method comprising step(s) of tilting said either platform or said bore sighted pair towards an external radiation source occulted by the STTS;

e. observing the STTS through a planetary atmosphere illuminated from the background by an external radiation source in the visible and/or other spectral domain, resulting in direct spectroscopy of the weakly absorbing species in the STTS; said method comprising step(s) of tilting said either platform or said bore sighted pair towards the limb of the planetary surface in angle to the Nadir f. providing a background reference measurement with no source from bore-sighted pair;

g. providing a reference measurement of said external radiation source from bore-sighted pair, providing for isolating the STTS's spectrum from that of the external source;

h. providing a reference point for spatial resolution of the spectral measurement with the other optic device;

i. acquiring many repeated measurements within a timescale of the measurement shorter than source timescale;

j. tilting at least one platform to any solid angle for measuring from said bore-sighted pair;

k. correcting for measuring solid angle;

l. Correcting for solar angle; or m. any combination thereof.

2. The method of claim 1 wherein at least one of the following is true:

a. said single chemical substance is replaceable by a mixture of a plurality of substances;

b. steps (d) to (g) are repeated for every chemical substance, for the same user defined distinct wavelengths;

c. said absorption coefficients of each chosen chemical substance are added at every user-defined distinct wavelength, thereby creating an additive absorption coefficient wavelength dependency for all substances;

d. said single layer is replaceable by a plurality of adjacent layers of either similar or different chemical composition at either similar or different P, T profiles;

e. steps (d) to (h) are repeated for every chemical substance for the same user defined distinct wavelength list and steps (h) and (i) are repeated for every layer and saved in a separated dimension;

f. an array of computerized processing units are used for processing individual data streams in parallel during the extraction of absorption coefficients of at least one molecular species, in at least one atmospheric layer, defined by given P,T,C parameters, at user-defined distinct wavelengths from molecular absorption databases, thereby obtaining a list of the user defined distinct wavelengths and the respective absorption coefficients which may be stored in the computer for further use for radiative transfer or for other calculations.

3. The method of claim 1, further comprising deducing the vertical temperature and concentration profiles of chemical species from the curve of growth based on an analysis of remote-sensing spectral data.

4. The method of claim 3, wherein said deducing vertical temperature and concentration profiles of chemical species comprises steps of a. obtaining an average temperature value for the planetary surface and/or atmosphere;

b. obtaining a vertical temperature profile, if available;

c. conducting an analysis of said absorption spectrum to identify atmospheric chemical species from comparison of data with spectral line database;

d. identifying a series of narrow lines of said chemical species of several angstroms wide each $\{\lambda^o_1, \ldots, \lambda^o_n\}$ where $\lambda^o$ denotes the central wavelength of the line;

e. calculating the equivalent width $W_k$ each line k, from the integral of the area under the absorption line, for $\lambda^{o-j}_k$ to $\lambda^{o+l}_k$, j and l are the extremal wavelengths of said line;

f. dividing the atmosphere arbitrarily into i layers of vertical height (z) denoted by $\Delta i$;

g. obtaining from a given line database the absorption coefficient, $\kappa_i(\lambda)$, for each wavelength of each line;

h. plugging the measured width $W_k$, the given absorption coefficient, $\kappa_i(\lambda)$ and the arbitrary width $\Delta i$ of the given layers for each lambda within the line and for each layer, into the effective line-width equation, adjusted by us for the general case of non-homogenous planetary atmospheres having a vertical distribution of chemical species such that:

$$W_k = 2\sum_j \left(1 - e^{-\sum_0^i \kappa_i(\lambda) N_i \Delta_i}\right)$$

where j is the running index over all wavelengths in line k and i is the running index on all atmospheric layers; the sum in the exponent is an approximation valid for thin lines only, i. calculating simultaneously the values of $W_k$ for all lines, by parameterizing an array of values for the concentrations of said chemical species $N_{i,j}$ for all wavelengths and atmospheric layers involved in the calculation of each line, and by iterating to convergence with a very high degree of accuracy, including about $10^{-9}$, to avoid local minima in the calculation;

j. defining curve of growth for all lines k, as described from the relationship log(Wk/$\Delta v_D$) vs log ($\Sigma_j$ $\Sigma_j N_{i,j}$); $\Delta v_D$ is the Doppler broadening of the line and is a function of T(z), thus requiring the input of vertical temperature profile by obtaining the same from:
 i. given measured vertical temperature profile T(z); or,
 ii. as a first approximation deduced from an assumption of exponential decay of the pressure with height; or
 iv. calculated from the hydrostatic equation for said planet; or,
 v. fully or partially parameterized during calculation of $W_k$ as a separate or a simultaneous iteration scheme, validated by the measured average temperature obtained from remote sensing data;

k. drawing the curve of growth from the $W_k$ and the $N_{i,j}$ array values for each line and from it, and obtaining a best fit curve;

l. Obtaining from the curve of growth the profile of the line effective width, representative of the absorption vs chemical species concentration in line of sight, for any spectral line of said chemical species at any height z provided it is only several angstroms wide; and m. providing the real vertical chemical species distribution consistent with the vertical layer widths $\Delta_i$, by using appropriate T, P values.

5. The method according to claim 4, wherein said method is formalized by processing by the following equations:
 a. if planetary atmosphere is homogeneous, then $\tau$, the optical depth is uniform in volume and the standard equivalent width Wk of a spectral line k is calculated according to the following formula:

$$W_k = 2\int_0^\infty \left(1 - e^{-\tau(z,\lambda)}\right) d\lambda$$

b. if the planetary atmosphere is not homogeneous and the gas concentration N(z) depends on height z, then $\tau$ is not uniform with height and is given by:

$$\tau(z, \lambda) = \int_{z=0}^Z \kappa(\lambda) N(z) dz$$

were $\kappa(\lambda)$ is the wavelength dependent absorption coefficient; the equivalent width is given by $$W_k = 2\int_0^\infty \left(1 - e^{-\tau(z,\lambda)}\right) d\lambda = 2\int_0^\infty \left(1 - e^{-\int_{z=0}^Z \kappa(\lambda) N(z) dz}\right) d\lambda$$

c. for a finite planetary atmosphere, each layer is denoted with the index i, and the integrals is written as finite sums so that:

$$\tau(z, \lambda) = \sum_0^i \kappa_i(\lambda) N_i \Delta_i$$

is the physical width of the atmospheric layer, $\kappa_i(\lambda)$ and $N_i$ are the wavelength dependent absorption coefficient and species' concentration for the i'th layer, respectively, then, the equivalent width W of a certain line k, where j is the index for the wavelengths, becomes:

$$W_k = 2\sum_j \left(1 - e^{-\sum_0^i \kappa_i(\lambda) N_i \Delta_i}\right)$$

the unknown is $N_i$, which appears in k equations for k parameters, and thus can be solved for; and d. if the expression in the exponent is large, due to heavy absorption, high concentration or large layer height, $W_k$ will vanish and no contribution will be gained from this line, chosen lines should thus satisfy the condition $\kappa_i(\lambda) N_i \sim 1$ in narrow layers, for $W_k$ to be valuable.

6. The method according to claim 4, further comprising steps of:
 a. conducting an analysis of said absorption spectrum to identify atmospheric chemical species from comparison of data with spectral line database;
 b. identifying a series of narrow lines of said chemical species of several angstroms wide each $\{\lambda^0_1, \ldots, \lambda^0_n\}$ where $\lambda^0$ denotes the central wavelength of the line;
 c. calculating the equivalent width Wk for each line k, from the integral of the area under the absorption line, for $\lambda^0 - jk$ to $\lambda^{0+l}$ k, j and l are the extremal wavelengths of said line;
 d. obtaining from a given line database the absorption coefficient, $\kappa i(\lambda)$, for each wavelength of each line;
 e. plugging said measured width $W_k$, the given absorption coefficient, $\kappa_i(\lambda)$, and the arbitrary width $\Delta_i$ of the given layers for each lambda within the line and for each layer, into the effective line-width equation, adjusted by us for the general case of non-homogenous planetary atmospheres having a vertical distribution of chemical species such that:

$$W_k = 2\sum_j \left(1 - e^{-\sum_0^i \kappa_i(\lambda) N_i \Delta_i}\right)$$

where j is the running index over all wavelengths in line k and i is the running index on all atmospheric layers; the sum in the exponent is an approximation valid for thin lines only;

f. calculating simultaneously the values of Wk for all lines, by parameterizing an array of values for the concentrations of said chemical species Ni,j for all wavelengths and atmospheric layers involved in the calculation of each line, and by iterating to convergence with a very high degree of accuracy, including about 10-9, to avoid local minima in the calculation;

g. drawing the curve of growth for all lines k, is described from the relationship log ($W_k/\Delta v_D$) vs log ($\Sigma_i \Sigma_j N_{i,j}$); $\Delta v_D$ is the Doppler broadening of the line and is a function of T(z), thus requiring the input of vertical temperature profile; this may be obtained from:
  i. given measured vertical temperature profile T(z); or,
  ii. as a first approximation, deduced from an assumption of exponential decay of the pressure with height; or
  iii. calculated from the hydrostatic equation for said planet; or,
  iv. fully or partially parameterized during calculation of $W_k$ as a separate or a simultaneous iteration scheme, validated by the measured average temperature obtained from remote sensing data;
h. drawing the curve of growth from the Wk and the Ni,j array values for each line and from it, a best fit curve is obtained;
i. obtaining from the curve of growth, the profile of the line effective width, representative of the absorption, vs chemical species concentration in line of sight;
for any spectral line of said chemical species at any height z provided it is only several angstroms wide; and
j. obtaining the real vertical chemical species distribution being consistent with the vertical layer widths $\Delta i$, by using appropriate T, P values.

7. The method according to claim 4, further comprising
a. if the planetary atmosphere is homogeneous, then T, the optical depth is uniform in volume and the standard equivalent width $W_k$ is calculated according to the following formula:

$$W_k = 2\int_0^\infty \left(1 - e^{-\tau(z,\lambda)}\right) d\lambda$$

b. if the planetary atmosphere is not homogeneous and the gas concentration N(z) depends on height z, then $\tau$ is not uniform with height and is given by:

$$\tau(z, \lambda) = \int_{z=0}^{z} \kappa(\lambda) N(z) dz$$

where $\kappa(\lambda)$ is the wavelength dependent absorption coefficient; the equivalent width is given by:

$$W_k = 2\int_0^\infty \left(1 - e^{-\tau(z,\lambda)}\right) d\lambda = 2\int_0^\infty \left(1 - e^{-\int_{z=0}^{z} \kappa(\lambda) N(z) dz}\right) d\lambda$$

c. for a finite planetary atmosphere, each layer is denoted with the index i, and the integrals can be written as finite sums so that:

$$\tau(z, \lambda) = \sum_0^i \kappa_i(\lambda) N_i \Delta_i$$

where $\Delta_i$ is the physical width of the atmospheric layer, $\kappa_i(\lambda)$ and $N_i$ are the wavelength dependent absorption coefficient and species' concentration for the i'th layer, respectively; then, the equivalent width W of a certain line k, where j is the index for the wavelengths, becomes:

$$W_k = 2\sum_j \left(1 - e^{-\Sigma_0^i \kappa_i(\lambda) N_i \Delta_i}\right)$$

the unknown is $N_i$, which appears in k equations for k parameters, and thus can be solved for;
if the expression in the exponent is large, due to heavy absorption, high concentration or large layer height, $W_k$ will vanish and no contribution will be gained from this line; chosen lines should thus satisfy the condition $\kappa_i(\lambda) N_i \sim 1$ in narrow layers, for $W_k$ to be valuable.

8. The method of claim 3, wherein said deducing the vertical temperature and concentration profiles of chemical species comprises steps of
  a. providing an absorption spectrum measured by remote-sensing for said planetary atmosphere; and
  b. dividing the atmosphere into i layers of vertical height (z) denoted by $\Delta_i$, such that said temperature and concentration profiles of chemical species is calculated for each of said i layers within each of said n vertical columns.

9. The method of claim 8, additionally comprising steps of:
  a. conducting an analysis of said absorption spectrum to identify atmospheric chemical species from comparison of data with spectral line database;
  b. identifying a series of narrow lines of said chemical species of several angstroms wide each $\{\lambda^0_1, \ldots, \lambda^0_n\}$ where $\lambda^0$ denotes the central wavelength of the line;
  c. calculating the equivalent width $W_k$ for each line k, from the integral of the area under the absorption line, for $\lambda^{0-j}_k$ to $\lambda^{0+l}_k$, j and l are the extremal wavelengths of said line;
  d. obtaining from a given line database the absorption coefficient, $\kappa_i(\lambda)$ and $N_i$ for each wavelength of each line;
  e. plugging said measured width $W_k$, the given absorption coefficient, $\kappa_i(\lambda)$ and the arbitrary width $\Delta_i$ of the given layers for each lambda within the line and for each layer, into the effective line-width equation, adjusted by us for the general case of non-homogenous planetary atmospheres having a vertical distribution of chemical species such that:

$$W_k = 2\sum_j \left(1 - e^{-\Sigma_0^i \kappa_i(\lambda) N_i \Delta_i}\right)$$

where j is the running index over all wavelengths in line k and i is the running index on all atmospheric layers; the sum in the exponent is an approximation valid for thin lines only;
  f. calculating simultaneously the values of $W_k$ for all lines, by parameterizing an array of values for the concentrations of said chemical species $N_{ij}$ for all wavelengths and atmospheric layers involved in the calculation of each line, and by iterating to convergence with a very high degree of accuracy, including about $10^{-9}$, to avoid local minima in the calculation;
  g. drawing the curve of growth for all lines k, is described from the relationship $\log(W_k/\Delta\nu_D)$ vs $\log(\Sigma_j \Sigma_j N_{i,j})$; $\Delta\nu_D$ is the Doppler broadening of the line and is a function of T(z), thus requiring the input of vertical temperature profile; this may be obtained from:

i. given measured vertical temperature profile T(z); or,
ii. as a first approximation deduced from an assumption of exponential decay of the pressure with height; or
iii. calculated from the hydrostatic equation for said planet; or,
iv. fully or partially parameterized during calculation of $W_k$ as a separate or a simultaneous iteration scheme, validated by the measured average temperature obtained from remote sensing data; and
h. the curve of growth should be drawn from the $W_k$ and the $N_{i,j}$ array values for each line and from it, a best fit curve is obtained, From the curve of growth, the profile of the line effective width, representative of the absorption vs chemical species concentration in line of sight, can be obtained for any spectral line of said chemical species at any height z provided it is only several angstroms wide; and,
i. the real vertical chemical species distribution is then made consistent with the vertical layer widths $\Delta_i$, by using appropriate T, P values.

10. The method of claim 8, wherein:
a. standard equivalent width Wk for homogeneous atmosphere is calculated according to the following formula:

$$W_k = 2\int_0^\infty \left(1 - e^{-\tau(z,\lambda)}\right)d\lambda$$

b. if the planetary atmosphere is not homogeneous and the gas concentration N(z) depends on height z, then $\tau$ is not uniform with height and is given by:

$$\tau(z, \lambda) = \int_{z=0}^{Z} \kappa(\lambda)N(z)dz$$

where $\kappa(\lambda)$ is the wavelength dependent absorption coefficient; the equivalent width is given by:

$$W_k = 2\int_0^\infty \left(1 - e^{-\tau(z,\lambda)}\right)d\lambda = 2\int_0^\infty \left(1 - e^{-\int_{z=0}^{Z}\kappa(\lambda)N(z)dz}\right)d\lambda$$

c. for a finite planetary atmosphere, each layer is denoted with the index i, and the integrals can be written as finite sums so that:

$$\tau(z, \lambda) = \sum_0^i \kappa_i(\lambda)N_i\Delta_i$$

where $\Delta_i$ is the physical width of the atmospheric layer, $W_k$ and the $N_{ij}$ are the wavelength dependent absorption coefficient and species' concentration for the i'th layer, respectively; then, the equivalent width W of a certain line k, where j is the index for the wavelengths, becomes:

$$W_k = 2\sum_j \left(1 - e^{-\Sigma_0^i \kappa_i(\lambda)N_i\Delta_i}\right)$$

the unknown is $N_i$, which appears in k equations for k parameters, and thus can be solved for;

if the expression m the exponent is large, due to heavy absorption, high concentration or large layer height, $W_k$ will vanish and no contribution will be gained from this line; chosen lines should thus satisfy the condition $\kappa_i(\lambda)N_i \sim 1$ in narrow layers, for $W_k$ to be valuable.

11. The method of claim 1, wherein said platform comprises at least one third backup spectrometer configurable to any of said first and/or second wavelength domains; said backup spectrometer is positioned off the optic axis and is optionally interconnected with a backup motor configured to move the main spectrometer out of the optic axis in case of failure of either said first or second spectrometer, thereby providing a continuous platform's operation; at least one remote sensor useful for accurate temporal, spatial and/or spectral mapping of spectrally structured rapidly changing radiation sources; a member of a cluster of three or more platforms providing for a better 2D or 3D geometrical identification; or any combination thereof.

12. The method of claim 1, further comprising steps of:
a. providing one two or more platforms for remote sensing of semi-transparent transitory source, each of which comprising at least one first spectrometer in a first wavelength range; at least one optic device selected from a group consisting of (i) one or more spectrometers, (ii) one or more imagers, and (iii) at least one spectrometer and at least one imager; each of which is sensitive either in said first wavelength range or in any second wavelength range; at least one platform; wherein said at least one first spectrometer and said at least one optic device are mounted on said platform and bore-sighted to observe the same or at least overlapping field of view;
b. bore sighting said pair of (i) said at least one first spectrometer and (ii) said optic device;
c. pointing said bore-sighted pair towards a semi-transparent transitory source;
d. taking at least one measurement of said source from said bore-sighted pair within a timescale 'τspectro shorter than τsource, and at least one measurement of a reference field-of-view; online or offline processing the same;
e. subtracting said reference from folded data of measurement(s) of said source;
f. calculating radiative transfer of the semi-transparent transitory source; and
g. overlapping of the spectral and other spectral or imaging data in the processing unit, studying the radiative transfer through said source, and comparing it to its spatial arrangement.

13. The method of claim 1, further comprising steps of:
a. using said window, extracting absorption coefficients from database without losing spectral data information;
b. bore-sighting at least one spectrometer with at least one spectrometer or imager;
c. mounting at least one bore-sighted pair on at least one platform;
d. pointing simultaneously all platforms towards at least one field of view;
e. acquiring data simultaneously by spectrometer, and optic device, from at least one platform of semi-transparent transitory source;
f. acquiring data simultaneously or alternately by spectrometer, and by spectrometer or imager from at least one platform of semi-transparent transitory source; and reference field of view for semi-transparent transitory source;

g. acquiring data simultaneously or alternately by spectrometer, and by optic device from at least one platform of at least two complementary fields of view of said source if required;

h. repeating at least one of step (e) to (g), from at least one platform, for a total timescale which is shorter than said source timescale;

i. adjusting data measured for different solid angles of different platforms;

j. relating spectral data from first spectrometer with data from optic device as a reference point for spatial resolution in observed properties of the semi transparent transitory source, by corresponding the overlapping field of views;

k. folding data acquired for each measurement period, for determining distinct spectral features in the vicinity of STTS;

l. Subtracting reference measurement from said measurement of semi-transparent transitory sources for each measuring method;

m. building a COG from the spectral line-widths to obtain the concentration profile through the layers; and n. using the concentration profile obtained by the COG and an energy conserving radiative code to conclude the structure of the inner radiative field of the semi transparent transitory source for different time resolved stages, thus to follow its change with time.

14. The method of claim 13, wherein said spectral features are measurable in parallel from one or more platforms, at one or more spectral domains, and at one or more spectral and imaging methods, and are configured to be analyzed together to obtain at least one of wider spectral coverage; SNR enhancement; better 2D/3D geometrical identification; and overlap different imaging methods.

15. The method of claim 1, further comprising step selected from the group consisting of:
   a. measuring a plurality of tilt angles thereby yielding a vertical profile of said species' concentration in STTS through planetary atmospheres;
   b. obtaining pointing knowledge from two or more platforms and providing for overlapping the spectral and the imaging data of said platforms;
   c. characterizing external/internal fluid motion of a rapidly changing diffused radiation source by providing one member of a group consisting the followings:
      i. combining spectroscopy and visible imaging, when emission is characterizable by a defined visible spectral range;
      ii. combining of spectroscopic and either IR or SAR imaging, when emission can be characterized by no visible components; and
      iii. providing a Doppler shift of spectral lines;
   d. characterizing external/internal fluid motion of a rapidly changing diffused radiation source by providing a Doppler shift of spectral lines in the same or different spectral domains, comprising steps of
      i. studying the line shape selected from a members of a group consisting of single non-shifted spectral line; sum of blue-shifted and redshifted lines indicative of motion in both directions, at low spectral resolution; resolved absorption spectra of separate blue shifted and/or red shifted lines if there are any; any combination of absorption and emission lines of the same spectral feature; any combination of absorption and emission lines interconnected with flow of material within semitransparent transitory source;
      ii. determining external/internal fluid motion of a rapidly changing diffused radiation source on one or more axes of observation; and
      iii. comparing with data from bore-sighted optic device to obtain a point of reference of spatial resolution for the motion in the semi-transparent transitory source;
   e. pointing either said platform and/or the bore sighted pair towards an external radiation source occulted by the semitransparent transitory source; thereby providing for illumination of the semitransparent transitory source by radiation originating in the external radiation source as to allow for direct spectroscopy of said source in wavelength range of external radiation source;
   f. providing for measuring chemical gradients in the environment of the semi-transparent transitory source by observing the semi-transparent transitory source from at least two opposite directions; or
   g. any combination thereof.

16. The method of claim 1, further comprising steps of:
   a. identifying a semi-transparent transitory source;
   b. providing for a sequence of spectral measurements of said source from the same or from different viewing angles;
   c. providing for said sequence of spectral measurements of said source within a timescale τspectro shorter than or equal to the rapid-change timescale τsource (τspectro≤τsource);
   d. acquiring said spectral measurements on a computerized platform;
   e. fixing for the viewing angle and FOV by dedicated algorithms;
   f. folding all members of said sequence by overlapping units on both axes; and
   g. obtaining an accurate spectrum with reduced SNR;
   said steps are configured to increase analysis accuracy.

17. The method of claim 15, wherein said FOV is selected from the group consisting of clear skies; clear aqueous or marine environment; FOV is provided by measuring an STTS from a different angle; and measuring a same field of view at a different solar angle or at night.

18. The method of claim 1, further comprising reducing spectral data volume while maintaining all of spectral data.

* * * * *